United States Patent [19]
Wedeven

[11] Patent Number: 5,679,883
[45] Date of Patent: Oct. 21, 1997

[54] METHOD AND APPARATUS FOR COMPREHENSIVE EVALUATION OF TRIBOLOGICAL MATERIALS

[76] Inventor: Lavern D. Wedeven, One Old Covered Bridge Rd., Newtown Square, Pa. 19073

[21] Appl. No.: 485,365

[22] Filed: Jun. 7, 1995

Related U.S. Application Data

[63] Continuation-in-part of Ser. No. 301,651, Sep. 6, 1994, abandoned, which is a continuation-in-part of Ser. No. 963,456, Oct. 19, 1992, abandoned.

[51] Int. Cl.$^6$ .............................. G01N 3/56; G01N 19/02
[52] U.S. Cl. .............................................. 73/10; 73/53.65
[58] Field of Search ................................ 73/9, 10, 53.05, 73/53.06, 53.07

[56] References Cited

FOREIGN PATENT DOCUMENTS

| | | | |
|---|---|---|---|
| 2277342 | 3/1976 | France | 73/10 |
| 46459 | 4/1981 | Japan | 73/10 |
| 242486 | 9/1969 | U.S.S.R. | 73/10 |
| 564579 | 7/1977 | U.S.S.R. | 73/10 |
| 796729 | 1/1981 | U.S.S.R. | 73/10 |
| 1587415 | 8/1990 | U.S.S.R. | 73/10 |
| 1633343 | 3/1991 | U.S.S.R. | 73/9 |

OTHER PUBLICATIONS

"Boundary Lubrication –An Appraisal of World Literature", The American Society of Mechanical Engineers, 1969, pp. 241–292.

Azzam, "Friction and Wear Testing Machines to Evaluate Tomorrow's Lubricants", American Society of Lubrication Engineers, 1969, pp., 172–181.

Dalmaz et al., "An Apparatus For the Simultaneous Measurement of Load, Traction and Film Thickness in Lubricated Sliding Point Contacts", Tribiology, vol. 5, No. 3, Jun. 1972, pp. 111–117.

Dyson et al., "Assessment of Lubricated Contacts–Mechanisms of Scuffing and Scoring", NASA Technical Memorandum 83074, Feb. 1983, pp. 2–19.

Gonin et al., "Lubricant Testing: A New Type of Machine", Tribiology, vol. 13, No. 1, Feb. 1980, pp. 25–29.

Kitchen et al., "Realistic Friction Testing", Machine Design, 16 Mar. 1967, pp. 1–8.

Primary Examiner—Hezron E. Williams
Assistant Examiner—Daniel S. Larkin
Attorney, Agent, or Firm—Robert Charles Beam, Esq.

[57] ABSTRACT

The present invention relates to a process and apparatus that allows a comprehensive evaluation of tribological materials. Such materials include lubricants (liquid, solid and gaseous materials) and load bearing surfaces (bulk materials, surface treatments and coatings). The process and apparatus enable a meaningful characterization of these materials in a way that connects basic lubrication, wear and failure mechanisms with machine hardware in its operational setting.

13 Claims, 42 Drawing Sheets

Figure 7  Traction Coefficient vs slip for two oils.

Figure 10 Method of differential rolling and sliding (DRS)

DRS Rolling & Sliding
Forward Ball Rotation $U_B$ = Ball Velocity Vector $U_D$ = Disc Velocity Vector S = Sliding Velocity Vector R = Rolling Velocity Vector $\gamma$ = Z * 90, (degrees)

$S = \sqrt{U_B^2 + U_D^2 - 2 U_B U_D \cos(\gamma)}$ $A = \sin^{-1}(\sin(\gamma)*(U_B/S))$ $B = \sin^{-1}(\sin(A)*(U_D/U_B))$ $A+B = 180 - \gamma$ $R = (1/2)\sqrt{U_B^2 + U_D^2 - 2 U_B U_D \cos(180-\gamma)}$ Figure 14 Anti-wear additive (TCP) reduces wear, but does not increase scuff capacity Figure 15 Anti-wear and "EP" characteristics of DOD-L-85734

Transition in ball temperature vs μs at 140 C seems to reflect a thermal response caused by chemical reactions to form surface films with oil PE-5-1761.

STARTING POINT

INCREASED SLIDING
CONSTANT ENTRAINING

CONSTANT SLIDING
DECREASED ENTRAINING

Figure 29

NA653.dat  10-17-94  9:45:55
PE-5-L-1850
0.8125   balldia    ball number: HG662-9
3.8      trackdia   disk number: 9-93a
ENGLISH  UNITS      90.0000  z

| RUN_TIME | TRACT | V_LOAD | Disk_TEMP | ball_temp | FLASH_TP |
|---|---|---|---|---|---|
| 0.0000 | 0.0000 | -2.1765 | 38.6000 | 38.6000 | 0.0000 |
| 4.0000 | 0.0000 | -0.0138 | 34.3000 | 38.0000 | 0.0000 |
| 8.0000 | -0.0382 | 1.1167 | 31.3000 | 33.3000 | 239.2144 |
| 12.0000 | -0.0376 | 3.9875 | 30.4000 | 33.8000 | 445.9946 |
| 16.0000 | -0.0361 | 4.0754 | 30.3000 | 34.0000 | 432.8391 |
| 20.0000 | -0.0346 | 3.9804 | 30.3000 | 34.4000 | 409.5912 |
| 24.0000 | -0.0323 | 3.9106 | 31.1000 | 35.3000 | 378.7687 |
| 28.0000 | -0.0342 | 4.0023 | 31.0000 | 34.9000 | 405.4319 |
| 32.0000 | -0.0315 | 4.1045 | 30.6000 | 35.1000 | 378.8311 |
| 36.0000 | -0.0313 | 3.9368 | 30.5000 | 35.3000 | 368.9214 |
| 40.0000 | -0.0331 | 3.9319 | 30.5000 | 35.4000 | 389.7536 |
| 44.0000 | -0.0319 | 3.8747 | 30.5000 | 36.0000 | 372.0699 |
| 48.0000 | -0.0331 | 3.7180 | 31.1000 | 36.5000 | 378.2440 |
| 52.0000 | -0.0310 | 3.8291 | 31.1000 | 36.0000 | 359.9388 |
| 56.0000 | -0.0311 | 4.0660 | 31.0000 | 36.2000 | 371.9821 |
| 60.0000 | -0.0339 | 4.0814 | 31.1000 | 36.4000 | 406.7342 |
| 64.0000 | -0.0358 | 7.7088 | 30.9000 | 37.5000 | 589.8398 |
| 68.0000 | -0.0359 | 8.0291 | 31.0000 | 38.5000 | 603.5292 |
| 72.0000 | -0.0346 | 7.8807 | 31.1000 | 38.9000 | 575.5953 |
| 76.0000 | -0.0334 | 8.0233 | 31.2000 | 39.2000 | 560.8347 |
| 80.0000 | -0.0337 | 7.9487 | 31.4000 | 39.7000 | 563.4721 |
| 84.0000 | -0.0332 | 8.0793 | 31.5000 | 40.2000 | 560.1710 |
| 88.0000 | -0.0334 | 7.8830 | 31.6000 | 40.4000 | 556.4841 |
| 92.0000 | -0.0328 | 7.9884 | 31.4000 | 40.5000 | 549.2629 |
| 96.0000 | -0.0329 | 7.9782 | 31.3000 | 40.4000 | 551.3738 |
| 100.0000 | -0.0324 | 8.0011 | 31.8000 | 40.7000 | 543.8929 |
| 104.0000 | 0.0326 | 8.0442 | 31.8000 | 41.2000 | 548.0959 |
| 108.0000 | 0.0332 | 8.1474 | 31.8000 | 41.4000 | 562.9559 |
| 112.0000 | 0.0328 | 8.0238 | 32.1000 | 41.9000 | 551.5176 |
| 116.0000 | 0.0333 | 8.0815 | 32.1000 | 42.1000 | 560.8535 |
| 120.0000 | 0.0335 | 7.9639 | 32.3000 | 42.6000 | 561.6888 |
| 124.0000 | 0.0365 | 11.6413 | 32.6000 | 44.1000 | 739.7724 |
| 128.0000 | 0.0371 | 11.9859 | 32.3000 | 44.7000 | 761.1167 |
| 132.0000 | 0.0364 | 12.0063 | 32.7000 | 45.7000 | 749.1272 |
| 136.0000 | 0.0352 | 12.0016 | 32.8000 | 46.3000 | 723.0289 |
| 140.0000 | 0.0353 | 12.0363 | 32.8000 | 46.5000 | 726.0654 |
| 144.0000 | 0.0352 | 12.1152 | 32.7000 | 47.2000 | 726.9247 |
| 148.0000 | 0.0345 | 12.0977 | 33.1000 | 47.7000 | 710.9625 |
| 152.0000 | 0.0344 | 12.0029 | 33.1000 | 47.8000 | 706.4723 |
| 156.0000 | 0.0341 | 11.9929 | 33.1000 | 47.9000 | 700.5190 |
| 160.0000 | 0.0346 | 11.9163 | 32.8000 | 47.9000 | 708.0755 |
| 164.0000 | 0.0338 | 11.9351 | 32.9000 | 48.2000 | 691.9674 |
| 168.0000 | 0.0343 | 12.0343 | 33.3000 | 48.8000 | 706.9609 |
| 172.0000 | 0.0343 | 12.0050 | 33.4000 | 49.4000 | 705.7131 |
| 176.0000 | 0.0341 | 12.0150 | 33.5000 | 49.7000 | 700.6653 |
| 180.0000 | 0.0347 | 12.0291 | 33.7000 | 50.3000 | 713.8642 |
| 184.0000 | 0.0379 | 15.7087 | 33.8000 | 52.4000 | 891.3083 |
| 188.0000 | 0.0387 | 15.9880 | 33.8000 | 52.7000 | 918.2897 |
| 192.0000 | 0.0376 | 16.1722 | 34.0000 | 53.9000 | 897.9112 |
| 196.0000 | 0.0370 | 15.8385 | 34.3000 | 55.7000 | 873.7448 |

Figure 30

Figure 34 Schematic drawing showing characteristic inlet dimensions

Figure 35 Load capacity traction behavior for various roughness combinations with gas turbine oil

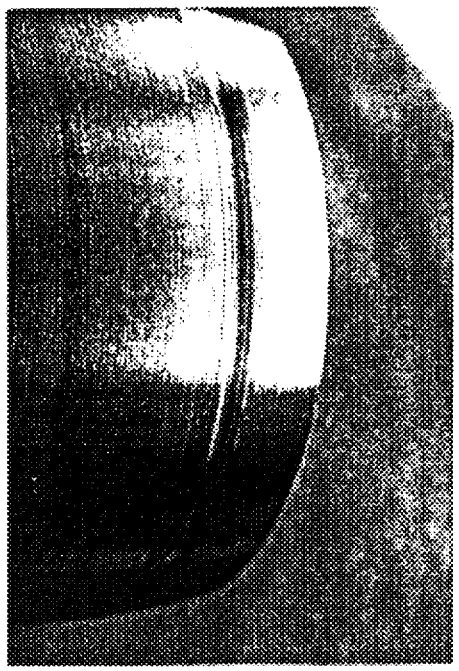
Figure 41

METHOD AND APPARATUS FOR COMPREHENSIVE EVALUATION OF TRIBOLOGICAL MATERIALS

This application is a Continuation-in-Part of U.S. patent application Ser. No. 08/301,651, filed Sep. 6, 1994, now abandoned, which was a Continuation-in-Part of U.S. patent application Ser. No. 07/963,456, filed Oct. 19, 1993, now abandoned.

BACKGROUND OF THE INVENTION

1. Field of the Invention

The present invention relates to a process and apparatus that allows a comprehensive evaluation of tribological materials. These materials include lubricants (liquid, solid and gaseous materials), and load bearing surfaces (bulk materials, surface treatments and coatings). The apparatus and associated methodologies enable a meaningful characterization of these materials in terms of basic lubrication, wear and failure mechanisms. The materials are evaluated in a rolling/sliding contact system (tribo-contact system) in a way that provides a connective link to operating hardware and its performance.

The invention focuses on the evaluation and development of lubricants and materials for bearings, gears and similar components where contacting bodies in relative motion are in intimate contact. Current test devices and associated test methods are limited in their ability to extrapolate data to hardware performance. Their use is most often limited to ranking materials over a narrow range of operating conditions. The test data has limited value for design purposes and performance prediction. This limitation is associated with the complexity of the tribo-contact system, particularly with regard to the contributions of the physical properties of the lubricant and the chemical interaction between the lubricant, materials and environment. This complexity has resulted in a host of test methods and devices that tell only part of the story. Different test rigs, for example, are used to evaluate anti-wear performance, load capacity and rolling contact fatigue. But, these performance attributes are intimately connected in operational hardware and it is difficult to evaluate these connections when the performance attributes have to be evaluated independently with different test machines and disconnected lubrication and failure mechanisms.

The process disclosed by the invention is able to separate the physical properties that affect performance from the chemical interactions of boundary film lubrication and material failure processes. The process is based on the isolation of lubrication mechanisms such as hydrodynamic, and specifically elastohydrodynamic (ehd), lubrication from the boundary film mechanisms and failure processes. Hydrodynamic or ehd mechanisms are dependent on three characteristic features: (1) convergent surfaces, (2) relative motion and (3) a viscous fluid media. Boundary film lubrication mechanisms and failure processes are derived from surfaces in intimate contact, or at least, close encounter. The physical locations of these phenomena within the tribo-contact are not exactly the same. The apparatus of the invention provides the ability to independently control the operation parameters of these locations, thus separating the hydrodynamic and boundary lubricating mechanisms within a tribo-contact system.

The test methodologies derived from the process and associated apparatus characterize the multi-dimensional attributes of the materials in the tribo-contact system. The methodology views the tribological contact as a multiple parameter problem which is dependent on lubricant, rolling velocity, sliding velocity, temperature, contact stress, surface materials, finishes, and surface treatments. The test methodology and apparatus closely match parameters to the field conditions of an application, while providing additional instrumentation and the ability to explore changes to any of the parameters independently in a controlled manner. Results are shown in real time, in terms of coefficient of friction and lubricant film thickness. Scuffing, wear, pitting, and corrosion can also be monitored. Data is available both in raw form and in tribological terms. Test data can be saved to a permanent storage device. The data can be post test processed to allow broader views of the contact tribology and the effects of changes on the system. The views of the data, like the inputs, are multiple-dimensional and can be matched to the user's needs. The combination of the methodology and the apparatus allows a user to characterize a tribological system over a range of operating conditions and predict performance for real world applications. The attributes can be identified on a performance map which illustrates the breadth, or range, of potential performance. Performance maps can be directly related to mechanical component operating conditions for in-service performance prediction. Within the performance map, the tribo-contact system is further characterized in terms of lubricating film forming properties and traditional attributes associated with anti-wear, load carrying capacity, EP performance, friction (traction) and contact fatigue.

2. Description of Prior Art

Characterization of lubricants and materials is performed by a variety of test devices and test methods.

Current standard test devices for oils are used to reflect selected attributes of oil performance. The ASTM D 4172 four-ball test evaluates "anti-wear" performance using bearing materials with smooth surfaces. Another four-ball test (ASTM D 2783) evaluates "EP" performance. Gear tests, such as ASTM D 1947 (which includes a Ryder Gear Machine, Erdco Universal Tester and the WADD Gear Machine) and IP-166 reflect the oil's "load capacity" (scuff) performance on gear materials with surface features much different than four-ball tests.

The Ryder Gear Test (ASTM D 1947) is used to determine an oil's lubricating ability as judged by its sensitivity to gear tooth "scuffing" (or scoring) resulting from the application of a step-wise loading protocol.

In addition to these commonly used standard test devices their are other related devices found in the patent literature. These include:

1. Method and Device for Testing Lubricating Properties of Lubricating Means (U.S. Pat. No. 4,311,036)
2. Apparatus for Measuring Anti-Wear Properties of Pressurized Liquids (U.S. Pat. No. 4,228,674)
3. Apparatus for Testing Lubrication and Material Properties (U.S. Pat. No. 4,466271)
4. Bearing and Lubricating Film Test Method and Apparatus (U.S. Pat. No. 3,952,566)
5. Friction Testing Machine for Lubricants (U.S. Pat. No. 3,913,377)
6. Means for Determining the State of Lubrication in Surfaces Lubricated by a Lubricant and Rolling or Sliding with Respect to one Another (U.S. Pat. No. 4,728,943)
7. "Method and Device for Examining the Wear and Friction Properties of Surface Materials Exposed to Sliding Friction" U.S. Pat. No. 4,939,922.

8. "Apparatus for Testing Lubricants" U.S. Pat. No. 3,041,868, "Test device for liquid or solid lubricants—measures frictional forces between rotating disc and second piece with lubricant between" FR. 2277-342,
9. "Testing of Antifriction, Antiabrasion & Antiseizure Properties of Lubricants" SU 242-486.
10. "Materials Friction and Wear Test Machine" SU 1633-343-A
11. "Ball-sphere Surface Pair with Lubricant Friction Test Machine" SU 1587-415-A
12. "Friction and Wear Testing of Disc-Pin Pairs" SU 1490-593-A
13. "Materials Friction Test Rig" SU 197707
14. Ductile Steel and Corresp. Lubricant Wear Test Stand" SU 1462-162-A
15. "Evaluation Test Method for Lubricating Property of Rolling Oil Emulsion" JA 56-46459
16. "Measuring Method Using Hertz Contact Regions" U.S. Pat. No. 3,106,837

It is recognized that the above inventions and standard test methods, which reflect selected attributes of oil performance, frequently do not have correlation with field experience. The standard four-ball test documentation even provides the warning: "The user of this test method should determine to his own satisfaction whether results of the test procedure correlate with field performance or other bench test machines."

The limited applicability of these tests is due to the narrow scope of evaluation, which does not reflect the true multi-functional attributes that lubricants and materials possess. For example, a single wear scar diameter or load rating number simply does not adequately reflect the oil's functionality in terms of its attributes relating to the combined effects of hydrodynamic and ehd film forming properties; traction (friction) and associated heat generation; anti-wear and scuffing propensity. The limited scope of these test machines and methodologies makes it difficult to make a direct connective link between test results and hardware performance such as one would find in rolling element bearings, gears and other mechanical components with load bearing contacts in motion. It is important that a test device and associated test methodologies are sufficiently flexible to simulate the lubrication and failure modes that are encountered in service.

Current test methods and devices are limited because they do not invoke all the relevant lubrication and failure mechanisms the real hardware encounters.

Current test methods and devices are limited because they do not follow the same lubrication and failure pathways that real hardware encounters.

Conventional test machines do not have the ability to cover the range of kinematics, materials, and environment found in real world applications. The conditions at which these tests are run are normally quite different from the "real world" application. The motion of the test specimens might be entirely sliding while the actual application involves rolling velocity. If the tests are able to replicate the actual conditions of sliding velocity, rolling velocity, contact stress, temperature, materials, surface finishes and lubricants, the test would be applicable for only those specific conditions. The results would only indicate passing or failing to operate at those conditions as opposed to determining an operating range. It is difficult to match the results of a test apparatus to the needs of a specific application and the type of data needed for a specific application. The type of data taken depends on the machine, rather than what is desired by the user. It is generally not possible to vary rolling velocity, sliding velocity, temperature, material properties and load all independently. It is generally not possible to plot results of any dependent variable in terms of any of these independent variables. The described invention overcomes these limitations while providing additional features which allow increased ease and flexibility in the testing of lubricants.

SUMMARY OF THE INVENTION

The objective of the present device and test methodology is to provide a tool for the comprehensive evaluation of tribological materials that can provide both fundamental property data and in-service performance prediction.

The comprehensive approach is based on the need for a process and test apparatus that can simulate the in-service lubrication and failure mechanisms encountered in applications and also the need to quantify the physical and chemical attributes of the contacting materials that contribute to in-service performance. Further, there is a need for simulation of standard test methods to provide a connective link with existing data bases and a need to provide fundamental or empirical data for component design.

The invention is based on dynamic and kinematic control of contacting bodies with preferred specimen geometry of a single "point" contact. In the preferred embodiment, this "point" contact is generated between ball and disc test specimens.

The evaluation process is based on the premise that the performance of a tribo-contact system, and its simulation of practical mechanical components, can be achieved by the precise application of a normal stress (load), tangential strain (kinematics) and environment (e.g. temperature) over a wide range of conditions. In this way, all the major lubrication and failure mechanisms that control in-service performance can be invoked. One of the important features of this invention is the control of not only the surface velocities of the test specimens but also their angular relationship. This allows the entraining velocity in the inlet region to the contact to be de-coupled from the sliding velocity within the contact region. By so doing, the lubrication mechanisms which depend on the entraining velocity in the inlet region can be controlled independently from the complex tribo-chemical processes and failure processes in the contact region. The latter are controlled primarily by the sliding velocity.

The evaluation process is directly connected to lubrication theory (hydrodynamic, elastohydrodynamic, boundary film). The testing process can follow the tribological pathways of lubricated contacts found in component hardware, such as gears and rolling element bearings. The process and apparatus go well beyond the singular perspectives offered by standard test methods and machines.

It is now possible, for example, to capture the total breadth of lubricating attributes of an oil inherent in its service performance. The approach can involve a two-step process: (1) the development of a performance map which identifies lubrication and failure regimes (e.g. ehd, mixed film lubrication and scuffing) and (2) the quantification of viscous film-forming and chemical boundary film attributes. These relate to customary concepts of anti-wear and load-carrying performance, along with full-film elastohydrodynamic (ehd) lubrication.

If properly done, the performance maps can be directly related to bearing and gear applications through the identification of the relevant entraining velocities and sliding velocities along with contact stress, material, surface finish and temperature. The device and methodologies provide the opportunity for: (1) hardware simulation, (2) comprehensive oil and material evaluation, (3) fundamental and empirical design data, (4) R&D testing, (5) standard test method simulation and (6) qualification testing.

BRIEF DESCRIPTION OF THE DRAWINGS

FIG. 29 is an image of the screen prior to the start of data collection.

FIG. 30 is part of an ASCII data file created by the apparatus.

FIGS. 41A and 41B show micro-pitting which has been accelerated due to previous micro-scuffs encountered along the testing pathway.

DETAILED DESCRIPTION OF THE PREFERRED EMBODIMENT

The description of the preferred embodiment is given for the process and apparatus of the invention.

Preferred Embodiment of Process

Background

The present invention provides a process and apparatus to perform a comprehensive evaluation of tribological materials. The invention provides useful information to the formulators and fabricators of tribological materials and also critical data to the designer, developer and user of mechanical components for performance prediction.

The topic of lubrication and the failure of lubricated surfaces is quite complex. The performance of the lubricant, with its physical and chemical properties, in most cases cannot be formulated into simple and reliable equations to predict the role of lubricant properties in the failure process. Failure in the form of wear, scuffing or contact fatigue is not an intrinsic property of a bearing or gear material. In addition, the performance of an oil or grease is not an intrinsic property of the oil alone; but, it is the result of the physical and chemical interactions within an entire lubricated contact (tribo-contact) system. Consequently, the evaluation of tribological materials with simple test devices and test methodologies frequently has little correlation with experience. The design or selection of a lubricant is both science and experience based. The rationale is derived from both lubrication and failure mechanisms and their interactions within a lubricated contact system.

The lubricant prevents failure through the formation of lubricating films by hydrodynamic lubrication, elastohydrodynamic (ehd) lubrication and boundary lubrication. The criteria for failure is judged by the user. If the deterioration of the surfaces or level of friction has progressed to the degree that it threatens the essential function of the component, it can be considered to have failed.

Figure 1:
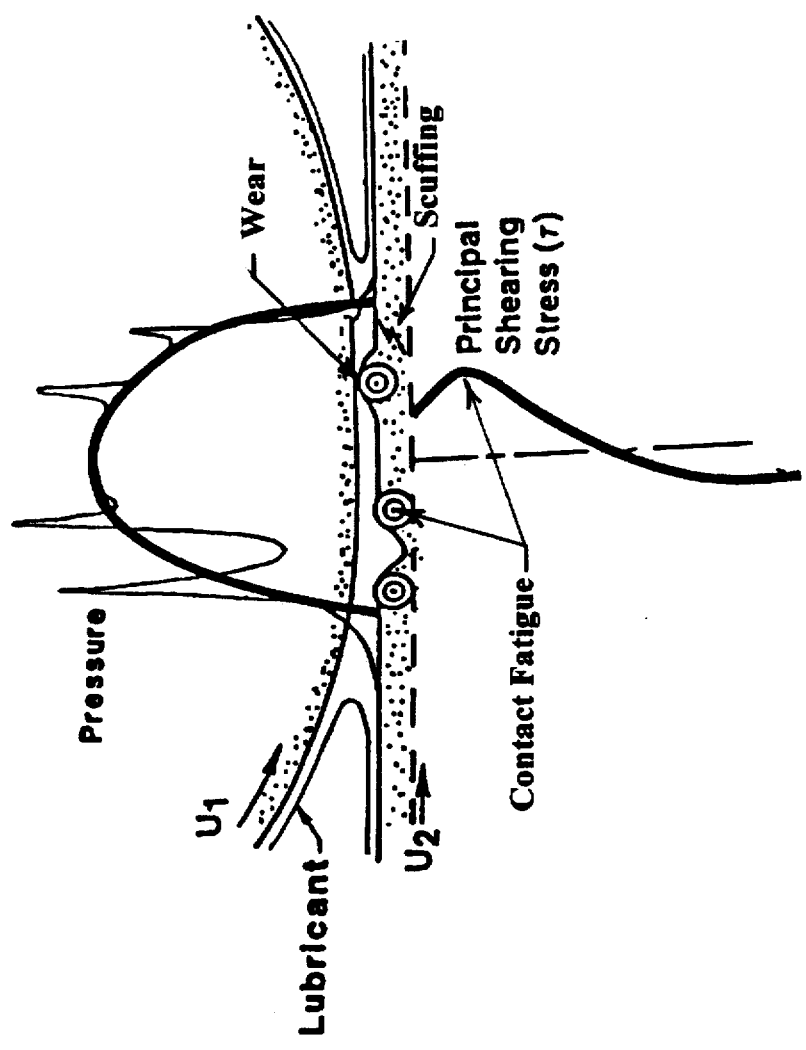
FIG. 1 shows schematically the general modes of failure and their initiating sites within a concentrated contact that may represent a lubricated contact interface between gear teeth and bearing elements.

Through experience, distinct classes of failure have become recognized. The general failure classifications are wear, scuffing and contact fatigue. They are shown schematically in FIG. 1. These failure classes are defined without presupposing the exact mechanism by which they occur. They are defined in engineering terms based on a description of observations. The observations and their classifications reflect the remaining evidence of a complicated sequence of events involving many physical and chemical processes that preceded it. Associated with the physical and chemical interactions on the surfaces are several mechanistic wear processes which generally fall under the basic mechanisms of:

Adhesion
Chemical reaction
Plastic flow
Fatigue

During the service life of a component, the lubricant must provide the lubrication mechanisms required to prevent or control these basic wear processes. The development of a process and apparatus for a comprehensive evaluation must be able to control the lubrication mechanisms and invoke the mechanistic wear processes in a manner meaningful to anticipated service. The process of the present invention is based on viewpoints of the tribo-contact system involving: (1) the locations of failure initiation, (2) the structural elements of a tribo-contact and (3) the identification of mechanistic operating regions.

The Locations of Failure Initiation

From a practical viewpoint, the performance limits of contacting surfaces which carry loads and transmit power are characterized by general failure processes described as wear, scuffing and contact fatigue. There are many descriptive terms that characterize subsets of the general failure process. The locations of the failure process are shown schematically in FIG. 1. There are other failure processes that may not fit under these categories, such as the growth of surface oxides which have high friction. This may not be wear by a strict definition, but it is a form of surface deterioration. The process of the invention is based on the recognition that the major failure modes are initiated at specific locations within the tribo-contact. Wear is a gradual removal, displacement or deterioration of surface material. Scuffing is a sudden catastrophic loss of surface integrity which destroys the surface and near-surface material. It is usually accompanied by a sudden rise in friction or traction. Contact fatigue is the loss of material from the surface due to the initiation of a crack and its propagation which leaves a pit or spall on the surface. The crack may initiate at or near the surface due to local stress concentrations or imperfections in the material, or it may initiate below the surface near the location of the maximum principal shearing stress.

Wear, scuffing and contact fatigue differ in terms of their mechanistic processes, as well as the locations within the tribo-contact where they initiate. The initiation and progression of the various failure modes can occur simultaneously. In this regard, they can be thought of as competitive modes of failure. They can also be interactive due to their proximity.

The simultaneous and interactive nature of failure modes is one of the major reasons for the difficulty of predicting performance and evaluating materials for improved performance. The pathways to performance limits can be easily altered by slight operational changes in stress, temperature and lubricating films. The testing of materials and lubricants is very machine and method dependent. The test machines are limited in the failure modes that can be invoked and the test methods are limited in the interconnections that can be made among the failure modes. In addition, the data for performance prediction is limited and the results are restricted to relative ranking over a narrow range of operating conditions. The limitation of test machines and methodologies has resulted in the development of materials with improved properties for one failure mode such as contact fatigue, but a loss of performance in another failure mode such as wear.

Structural Elements of a Tribo-Contact

Figure 2:
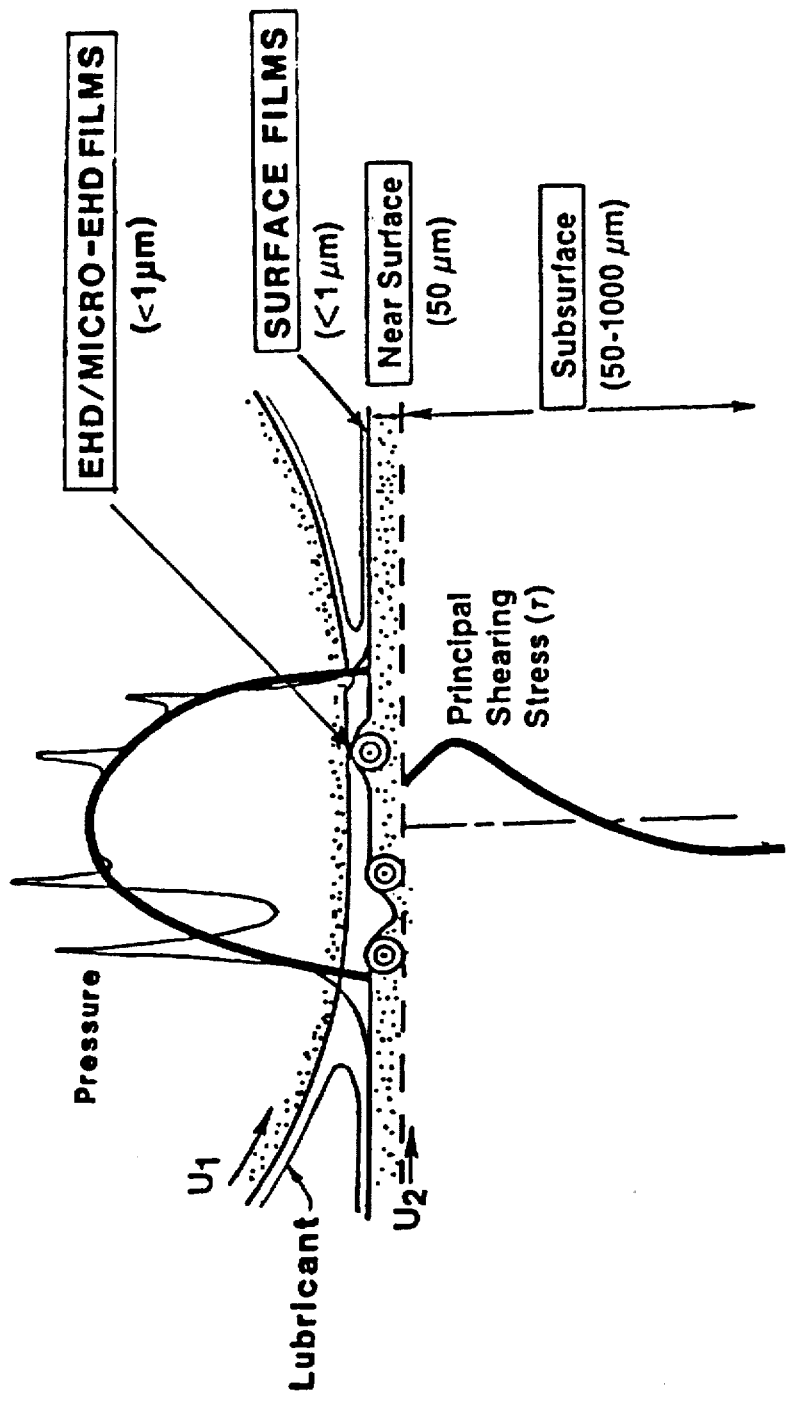
FIG. 2 shows schematically the structural elements of a lubricated contact that control performance.

The process of the invention is based on the identification of four structural elements of a tribo-contact which control its basic performance. The four structural elements for a concentrated contact are shown schematically in FIG. 2. The process of the invention evaluates the technology of these structural elements, all of which comprise a tribo-contact system. A comprehensive process and apparatus for the evaluation of tribological materials must assess the operation of the entire tribo-contact system. The performance is derived from the integrity of four structural elements. Each structural element, or region, performs certain functions in the lubrication and failure process. The success of the lubricant and contact materials depends upon how well the normal stress and tangential shear associated with a given loading are accommodated by these regions in the face of a wide range of operating conditions.

The ehd and micro-ehd lubricated region is created by the generation of an elastohydrodynamic (ehd) lubricant film.

On a global scale, the ehd film is derived from the hydrodynamic pressure generated in the inlet region of the contact. On a local scale, it is derived from the micro-ehd lubrication action associated with the local topography of the surfaces. The ehd/micro-ehd region is typically less than 1 μm thick. Ehd films serve to distribute the stress uniformly across the hydro-contact area and provide a thin film with low shear strength. The presence of ehd films is essential for extended life and the prevention of the initiation of failure modes.

The surface film region contains the thin outer layers of the contact surfaces. They consist of surface oxides, adsorbed films and chemical reaction films derived from the lubricant and its additives. These surface films are almost always less than 1 μm thick. One important function of surface films is to prevent local adhesive bonding between materials in intimate contact. Surface films with the best lubricating attributes have good bond strength to the contact surfaces, but low shear strength. These films are critical to wear resistance and scuff resistance.

The near surface region contains the inner layers of the surface. This region may include a finely structured and highly worked or mechanically mixed layer. It may also include compacted wear debris or transferred material from a mating surface. The deformed layers, which may be of a different micro-structure than the material below them, may arise from surface preparation techniques such as grinding and honing. They may also be induced during operation; for example, during running-in. Hardness and residual stress may vary significantly in this region. They may also be substantially different from the bulk material below. The near-surface region may be on the order of 50 μm below the surface. The thermal and mechanical properties of the near-surface region control wear, the onset of scuffing and surface initiated fatigue.

For concentrated contacts, a subsurface region can be defined, which may be 50 to 1000 μm below the surface. This region is not significantly affected by the mechanical processes that produce the surface or the asperity-induced changes that occur during operation. Its micro-structure and hardness may still be different from the bulk material below it, and significant residual stresses may still be present. These stresses and microstructures, however, are the result of macro processes such as heat treatment, surface hardening and forging. For typical Hertzian contact pressures, the maximum shear stress is located within the subsurface region (see FIG. 2). In other words, the detrimental global contact stresses are communicated to the subsurface region where subsurface-initiated fatigue commences.

One can also define a "quiescent zone" which is located between the near-surface region and the subsurface region. The "quiescent zone" resides at a depth below the surface in which the local asperity and surface defect stresses are not significant and the stress field from the macroscopic Hertzian contact stress is not yet appreciable. This zone is quiescent from the point of view of stress, the accumulation of plastic flow and fatigue damage. The existence of the quiescent zone is important with regard to rolling contact fatigue. It inhibits the propagation of cracks between the stress field in the near-surface region and the stress field in the subsurface region.

From the viewpoint of the structural elements of a tribo-contact system, and their function, it is clear that there are a multitude of lubrication and failure pathways that a given tribo-contact can take that will define its performance. It is understandable the test machines test machines that are available to evaluate tribological materials are limited in usefulness. Additional test machines and methods serve little to improve the state-of-the-m, unless the design and methodology are connected to a more rational process. Much of the difficulty in developing a rational process stems from the complex and unpredictable chemical and material interaction at the contact interface. The process of this invention removes some of the complexity by pulling out the hydrodynamic and ehd mechanistic processes which are on sound and predictable grounds. This allows a tractable approach to performance attributes of the complex tribo-chemical interactions within the contact region through testing and a meaningful connection to hardware performance prediction. The isolation of the hydrodynamic and ehd processes is obtained by the division of the tribo-contact into mechanistic operating regions.

The Mechanistic Operating Regions

Figure 3:
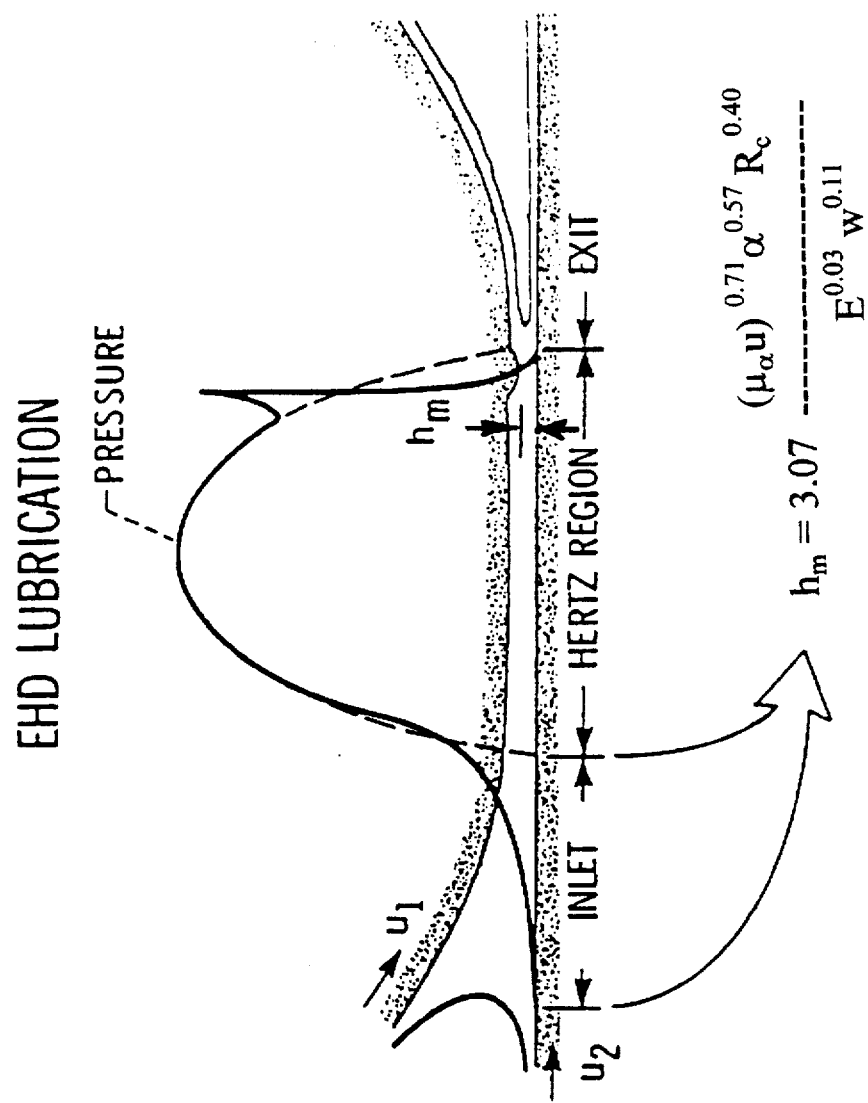
FIG. 3 shows how a tribo-contact can be divided into regions which are specifically connected with lubrication mechanisms or failure mechanisms. The inlet region is significant with regard to the generation of an elastohydrodynamic (ehd) oil film.

For a concentrated contact, like that shown in FIG. 3, the pressure and elastic deformation are very similar to the Hertzian contact condition for dry contact. A rational process for a comprehensive evaluation of tribological materials is developed by the assessment of the three mechanistic operating regions shown schematically in FIG. 3. The inlet region is the convergent portion of the contact as defined by the combined surface velocities which entrain the lubricating fluid into the contact. The inlet region is the "pump" that creates the separation between the surfaces in the Hertzian region. The generation of hydrodynamic and ehd pressure is primarily confined to this region. The Hertzian region is defined by the region of elastic (Hertzian) deformation where the "contacting" surfaces are parallel. The Hertzian region rides the ehd film that is generated in the inlet region. It also creates the surface films for boundary lubrication by way of tribo-chemical interactions between local areas of intimate contact. The last operating region is the exit region which discharges the lubricating fluid and "chemistry."

The process of this invention de-couples the ehd film generating mechanisms of the inlet region from the boundary film and failure mechanisms associated with the Hertzian region.

Evaluation Process

The complexity of evaluation and performance prediction of tribological materials can be reduced by the de-coupling of the inlet ehd film generating mechanisms from the chemical or boundary film generation in the Hertzian region. The rationale for the process developed in the invention is detailed for the inlet region and the Hertzian region.

Tribological Evaluation of Inlet Region

The formation of an ehd lubricant film is derived from the hydrodynamic pressure generated in the inlet region. Ehd lubrication is on excellent quantitative grounds. This allows the oil film thickness to be predicted from the viscous properties of the lubricant, the geometry of the contact system and their kinematic operating conditions. Ehd theory has proven to be a very useful design tool for predicting the lubrication regime for various applications. However, it is not sufficient to predict failure. This is partly because ehd lubrication is primarily an inlet phenomenon; that is, its major role occurs in a region removed from the Hertzian region where the more local events involved in failure initiation take place. The severity of these local events can be significantly influenced by the ehd lubrication process. The nominal thickness of an ehd film determines the degree of asperity interaction between the surfaces. Thus, the hydrodynamic or ehd lubrication mechanism is viewed as a quantitative foundation for performance prediction and evaluation. Boundary film lubrication and the destruction of the near-surface region is on much less quantifiable grounds and must be evaluated through appropriate testing.

For light loads and low contact pressures the generation of a hydrodynamic film follows the relation $$h_o = 4.896 \frac{U\mu_o R}{W}$$

where
$h_o$ film thickness on the line of centers
R equivalent radius of curvature
U one-half the sum of the surface speeds
$\mu_o$ viscosity
W load High loads or non-conforming geometry introduce elastic deformation into the hydrodynamic problem. A more important feature is the tremendous change in viscosity that results from the high pressures that are developed. The result is the rather remarkable load carrying mechanism of ehd lubrication. The lubricating film thickness formula derived from the Reynolds Equation for ehd conditions includes both elastic and viscosity-pressure parameters. The ehd film thickness has the following the equation:

$$h_m = 3.07 \frac{(\mu_o u)^{0.71} \alpha^{0.57} R_c^{0.40}}{E'^{0.03} w^{0.11}}$$

where
$h_m$ minimum film thickness
$R_c$ equivalent radius of curvature
u entraining velocity (symbol "R" also used)
$\mu_o$ atmospheric viscosity
$\alpha$ pressure-viscosity coefficient
E' equivalent elastic modulus
w load per unit width A significant feature for the ehd case, is that the film thickness generated is not very sensitive to the load (w) and the elastic modulus (E'). Yet, conventional test methods use a step loading protocol for evaluation. The effect of load on film thickness is usually an indirect cause. In the presence of sliding, the load increases the heat generation and temperature of the surface, which in turn reduces the viscous properties $\mu_o$ and $\alpha$.

The process of the invention focuses on the utilization of the entraining velocity, u, and the bulk temperature of the surfaces that control the viscous properties ($\mu_o$ and $\alpha$). The entraining velocity and surface temperature are the two parameters which have the greatest control of the ehd film thickness. The relationship between these two parameters and the film thickness that is pumped up between the surfaces is very precise and predictable. The phenomenon of the ehd pumping action occurs in the inlet region—upstream of the region where boundary films are formed and failure processes occur. As long as the surface geometry and temperature in the inlet region are reasonably maintained, the ehd film generation will continue to be operative.

To utilize the inlet ehd film generation mechanism for precise surface separation in the Hertzian region, the test apparatus is constructed to provide precise control and range of surface velocities and surface temperature.

Tribological Evaluation of Hertzian Region

There are but few applications which operate purely on hydrodynamic or ehd generated films. In most cases, hydrodynamic and ehd mechanisms operate along with boundary lubrication mechanisms. The former carries the chemistry for the latter to work, and the latter protects the surfaces so that the former can continue to operate. The joint action of the physical and chemical mechanisms seems to be a significant factor in performance. This is the reason for the lack of correlation between current test methods and field performance. Tribological material performance can only be evaluated appropriately when both types of mechanisms are allowed to operate.

Figure 4:
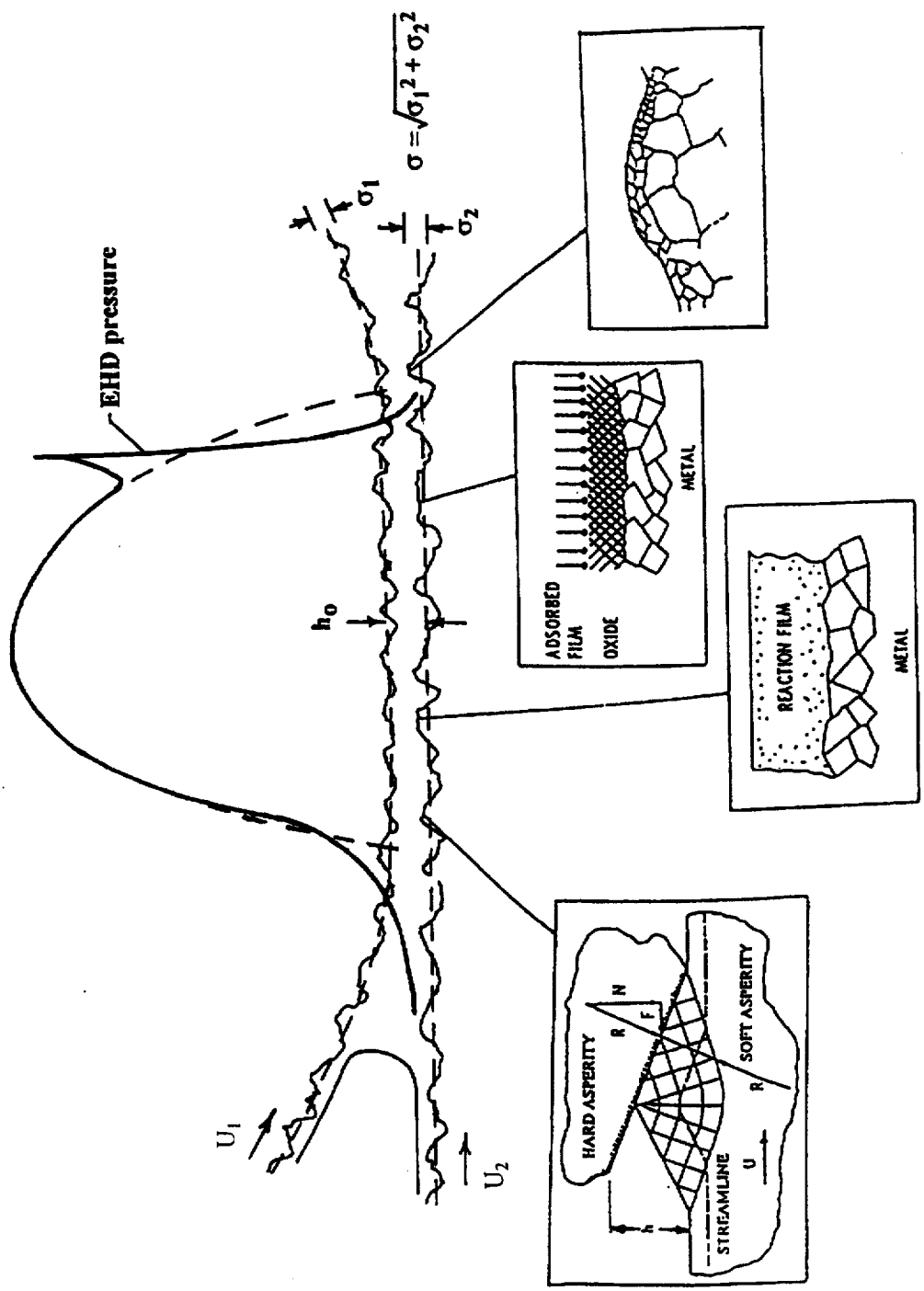
FIG. 4 shows schematically the complex material and lubricant interactions associated with boundary lubrication.

It is well known that surface films are important to boundary lubrication because in the absence of an ehd film they prevent adhesion and provide a surface film that is easy to shear. These films may be in the form of oxides, adsorbed films from surfactants and chemical reaction films from other additives or the bulk fluid. These surface films are schematically shown in FIG. 4.

The interactions of surface films are very complex. Most studies on the subject have focused on the chemical identification or phenomenological effect of surface films, but little is known about the mechanism of protection, the means of removal, or the rate of reformation. At high temperatures, the oxidation of the base fluid can contribute to surface film formation. There have been many studies on the catalytic effect of metals on the bulk oxidation of oils. Similar oxidative processes can occur under the thermal stress environment in the contact region where intermediate oxidation species can react with the surface or organo-metallic material that may be present. These reactions can influence boundary lubrication in several ways, such as corrosive wear, competition with other additives, or forming polymeric material—that is, a friction polymer.

The contribution of surface films in the prevention of wear is complex. The time and spatial distribution of the various surface films within the contact seems to be important, particularly with regard to the accumulation of material (including debris of all sorts) in surface depressions and the formation of films at asperity sites. In view of the complexity of surface films, one wonders what the real lubricating "juice" is in a real system. Its properties may be much different from the original lubricant applied.

Boundary lubrication with surface films occurs under conditions where there is significant surface interaction. The general characterization can be summarized by the following:

(1) The primary function of boundary lubrication is the formation of surface films to minimize wear and surface damage.

(2) The formation of surface films is controlled not only by oil chemistry, but also by interaction with the surfaces, wear debris and the environment.

(3) Boundary lubrication mechanisms are highly complex involving metallurgical effects, surface topography, physical and chemical adsorption, corrosion, catalysis and reaction kinetics.

(4) While the formation of surface films are very chemical in nature their performance is determined by mostly unknown physical properties such as shear strength, thickness, surface adhesion, film cohesion, melting point or decomposition temperature and solubility.

The fundamental physical and chemical properties of boundary lubricating films are really too complex to be of practical value to the user for design and performance prediction. In any case, they cannot even be measured. All that can be done is to utilize empirical boundary film properties that reflect their general performance for reducing wear and preventing catastrophic failure, i.e. anti-wear and EP (or load carrying) performance. Anti-wear and EP performance is evaluated by test methods which are difficult to relate to the user's hardware. The user is the ultimate judge of the performance attributes, which are presumed to be due to boundary film properties.

In almost all applications where boundary films are an essential contributor to lubrication performance they are accompanied by ehd generated films. That is, the load is shared between ehd films and boundary films. Operation under "mixed-film" lubrication conditions is common. The invention of a process and apparatus for a comprehensive evaluation provides precise control of surface separation for mixed-film lubrication. The lambda ratio, h/σ, which is the ratio of the hydrodynamic or ehd lubricant film thickness (h) to the average combined roughness height (σ) of the interacting surfaces. This is a simple way of describing the degree of asperity interaction. Thus, when lambda is >3, spalling fatigue life is much greater than for lower lambda, because local asperity stresses have been significantly reduced. Its connection with surface-initiated fatigue seems to be more obvious than failure modes associated with wear or scuffing. The latter failure modes generally appear at low lambda, less than 1, where the concept of lambda loses much of its meaning.

When σ is the same order of magnitude as h, the surface topography becomes intimately involved in the lubrication process itself in the form of micro-ehd lubrication. Local hydrodynamic or ehd pressures can be generated at asperity sites or topographical features associated with surface finishing processes or wear processes. Micro-ehd lubrication may be confused with boundary lubrication.

The focus of the present invention is to have the test method and apparatus control and measure the effects of boundary lubricating surface films in the presence of a partial ehd film with controlled thickness. The latter is controlled by the inlet ehd mechanism discussed above. The former is controlled by tribo-chemical processes due primarily to its temperature and the shear between the surfaces. The shear is controlled by the relative slip between the surfaces (sliding velocity).

Surface temperature is a key link between lubrication and failure. Temperature is a major driving force in the formation of chemical reaction films. It influences the rate of lubricant degradation. It influences the strength of surface films as well as the flow properties of the material in the near-surface region. Consequently, it is not surprising that the total temperature level is a frequently used criterion for failure, such as scuffing.

From a simplistic point of view the total temperature (T) is the sum of a bulk temperature ($T_b$) of each component and the "flash" temperature ($T_f$) associated with the instantaneous temperature rise derived from the friction within the lubricated contact. Flash temperature may arise from the traction of the lubricant film, as well as from the energy dissipated from the adhesion, plastic flow of surface films, and deformation of the material within the near-surface region. The magnitude of $T_f$ can be predicted if simplifying assumptions about the traction coefficient and convection heat transfer are made. Simulation of in-service performance with a test device is critically dependent upon the control of $T_b$ and $T_f$.

Because of the important role of the shear (sliding) and temperature within the Hertzian region regarding surface film formation and performance, the test apparatus provides precise control of the relative slip between the surfaces and the temperatures. The apparatus controls the bulk temperature ($T_b$) through heaters, shown as 230, 232 in FIG. 22. The flash temperature ($T_f$) is self-generated at the contact due to the sliding velocity and the traction coefficient. Continuous measurement of traction and slip allows real time prediction of $T_f$ as well as the total temperature, T. A comprehensive evaluation of the structural elements in the Hertzian region is performed by mapping performance over a large range of sliding velocities, temperatures with precise control of h/σ.

Process of Evaluation
Pressure-Viscosity Coefficient

The focus of a comprehensive process for tribological evaluation is on the empirically derived attributes which manifest themselves in the Hertzian region. To reduce the complexity of the lubrication and failure mechanisms in this region, the starting point of an evaluation process generally begins with the inlet region. The prediction and precise control of ehd film separation requires the pressure viscosity-coefficient (α). The effect of pressure on viscosity for lubricating fluids is not always known. The utilization of high-pressure capillary data is generally used. For precise ehd film thickness separation (h/σ), the apparatus of the invention derives the pressure-viscosity coefficient from the contact itself.

Figure 5:
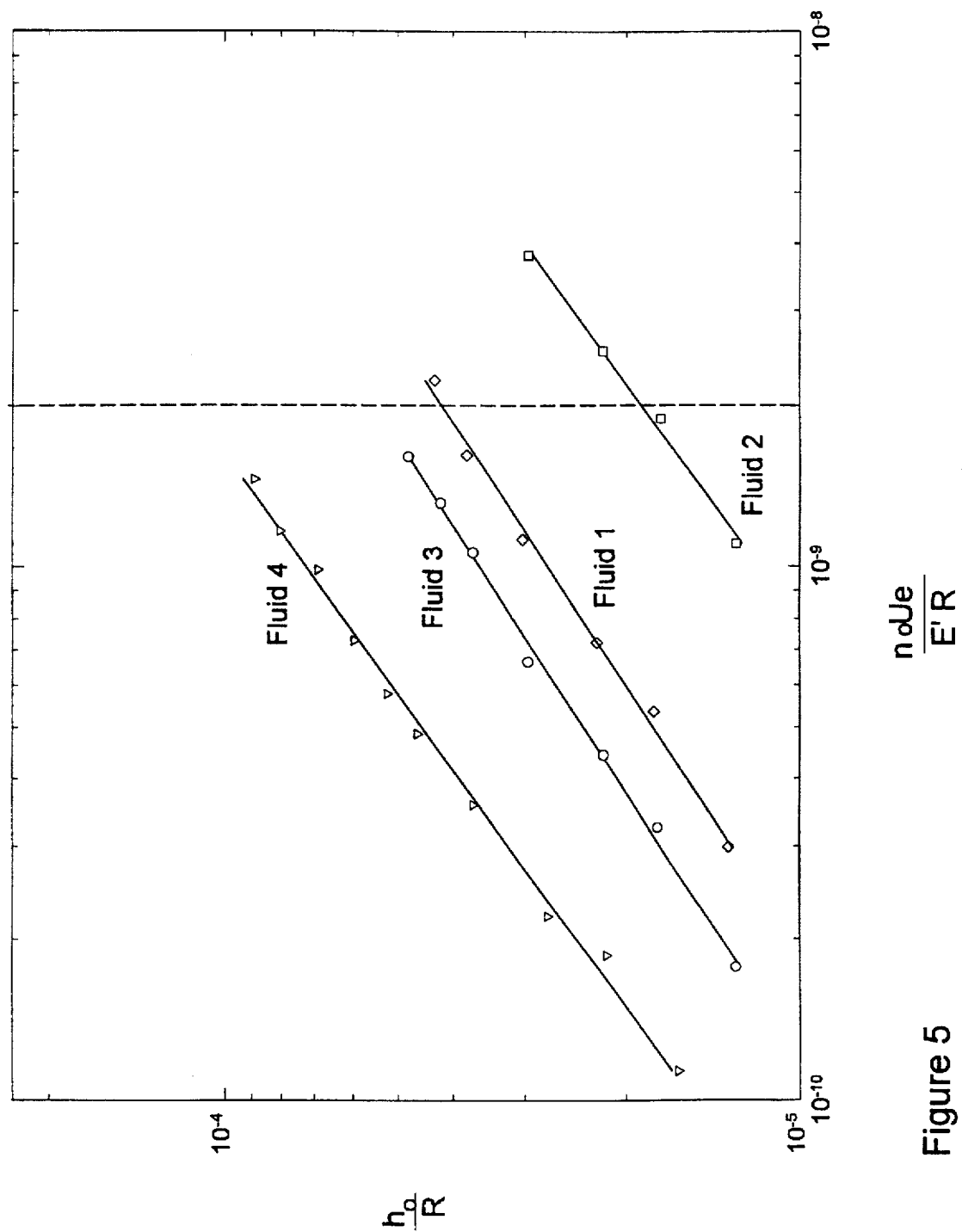
FIG. 5 shows optical interference data for ehd film thickness. The separation between lines reflect the pressure-viscosity coefficient of the fluid.

The pressure-viscosity coefficient of the lubricating fluid is determined by measuring the 3-dimensional shape of the ehd film with optical interferometry over a practical range of temperatures and entraining velocities. Typical optical film thickness measurements are plotted in FIG. 5 for several fluids. Since viscosity-temperature data is generally available, the effective pressure-viscosity can be derived from ehd theory or by using a reference fluid. For precision, the ehd theory is used with modified exponents with entraining velocity based on the actual measurements.

The optical interferometry method is also used to examine the shape of the ehd film in the Hertzian region with combined rolling and sliding, where the sliding velocity vector is not co-linear with the entraining velocity vector. The distortion of the shape reflects the rheological properties in the high pressure Hertzian region as a function of tangential shear.

The in situ-determination of pressure-viscosity coefficient allows ehd film thickness calculation for component hardware. It also serves to provide a precise surface separation calculation for a comprehensive evaluation to the lubricating attributes in the Hertzian region.

Process of Evaluation
Traction Coefficient

Figure 6:
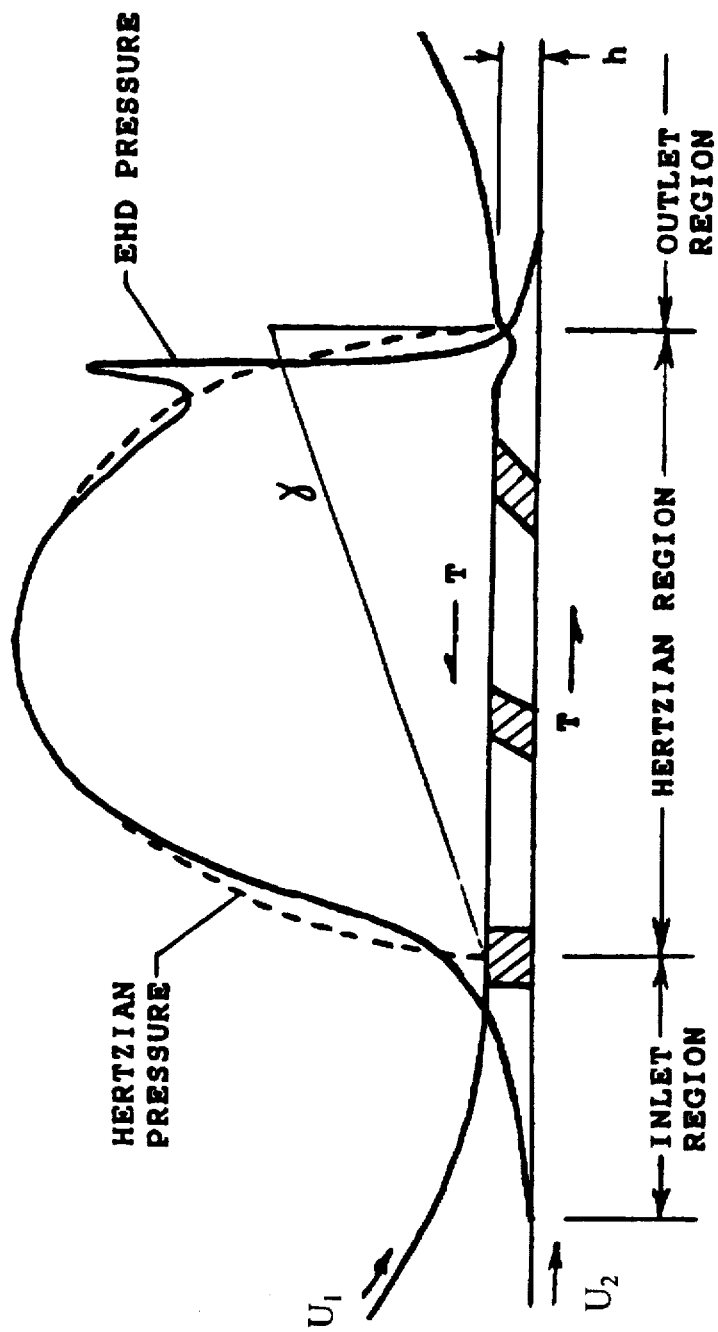
FIG. 6 shows schematically the buildup of oil film strain within the contact region with incipient sliding. The traction, or friction, between the surfaces is related to shear strength of the a pseudo-solid film caused by the high pressure in the Hertzian region.

Traction coefficient is defined as the tangential friction or traction force across the tribo-contact divided by the normal load. Traction is an important design and performance parameter because of its connection with heat generation in bearings and mechanical efficiency in gears. Under full ehd film conditions, the traction coefficient is determined by the limiting shear strength of the pseudo-solid oil within the Hertzian region under shear. Under incipient sliding conditions, typical for rolling element bearings, the shear of fluid within the Hertzian region builds up as the fluid transverses the contact region (see FIG. 6). The traction behavior of lubricating fluids under incipient sliding conditions is a function of the fluid molecular structure (see FIG. 7). Because of the pseudo-solid nature of the lubricating fluid, traction coefficient is a function of pressure and temperature.

The process and apparatus evaluates the traction coefficient over a practical range of pressures, temperatures and slip to provide heat generation, torque and efficiency predictions in component hardware. Traction is also measured as part of the comprehensive evaluation process. The measurement of traction coefficient as a function of temperature (see FIG. 8) under low slip conditions allows an indirect means to estimate the effective film temperature in the Hertzian region under self-generated frictional heating of the contact due to high sliding conditions. Also, the measurement of traction under ehd conditions with smooth surfaces provides a reference point for low h/σ operation, where the total traction is due to surface roughness and boundary films in addition to the shear of a partial ehd film. In this way, the contributions of surface finish and boundary film friction can be assessed.

Process of Evaluation

Use of Inlet Parameters to Enter Mixed-Film Region

Figure 9:
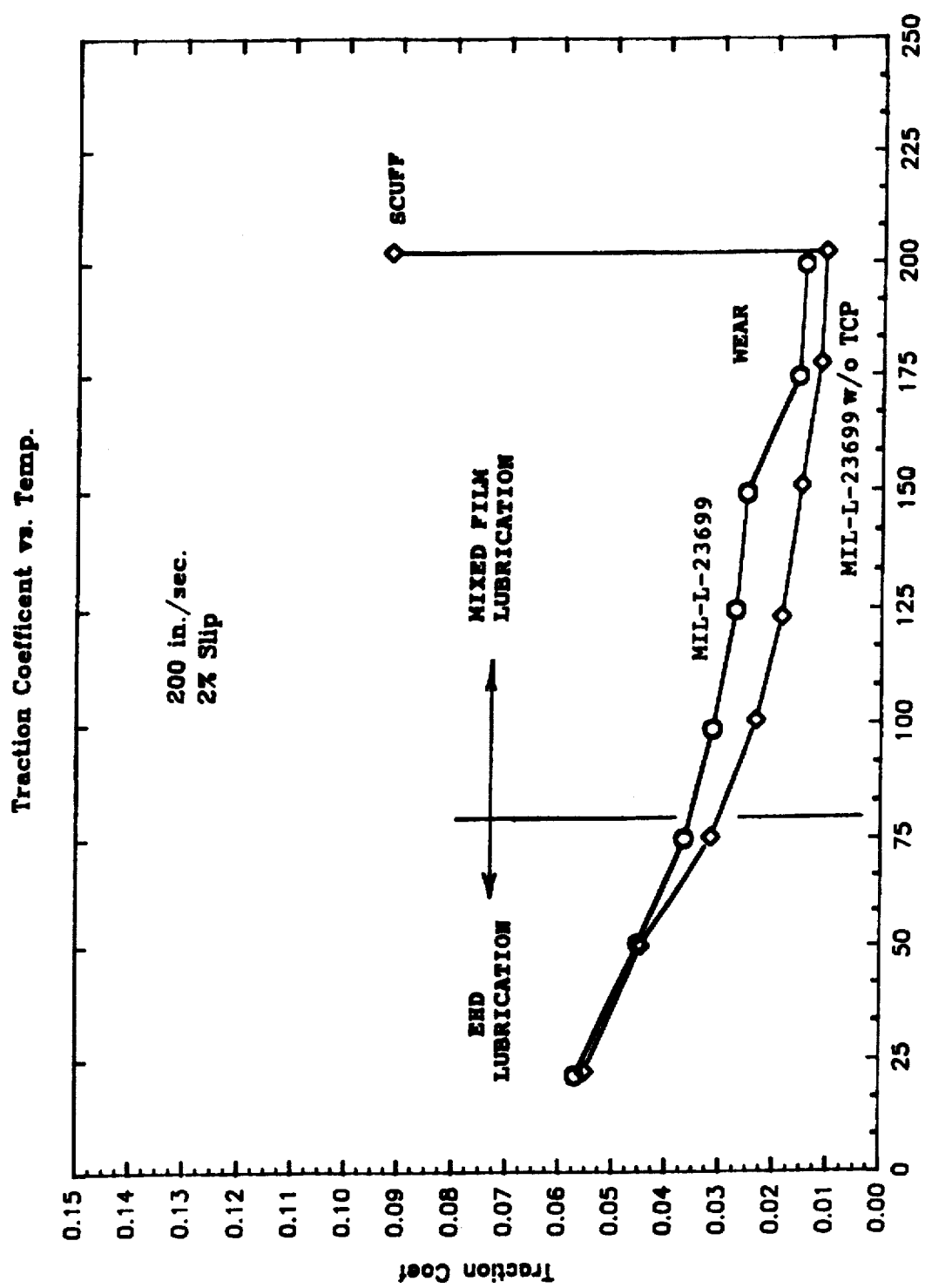
FIG. 9 shows the measured traction coefficient as a tribo-contact is driven into the mixed-film lubrication region by increasing the bulk temperature of the contacting specimens.

Several pathways from a full ehd film to mixed-film lubrication are used to conduct a comprehensive evaluation of tribological materials. The pathways selected may be based on hardware simulation or as a means to map the performance of the structural elements within the Hertzian region by the control of the ehd film generating parameters in the inlet region. The process and apparatus allow one or more of the following parameters to be used:

1. For a selected set of operating conditions, the bulk temperature of the test specimens is increased to reduce the ehd film thickness. The measurement of traction and wear determines the relative performance between test oil as shown in FIG. 9.
2. For a selected set of operating conditions, the entraining velocity is reduced to enter the mixed-film lubrication region.
3. For a selected set of operating conditions, the inlet region is starved of fluid to reduce the ehd film thickness and cause operation in the mixed-film region.

Process of Evaluation

Method to De-Couple Inlet and Hertzian Phenomenon

The process and apparatus of the invention provides a method to de-couple the generation of an ehd film in the inlet region from the shear within the Hertzian region.

The generation of an ehd film is an "inlet" phenomenon, controlled by the entraining velocity (u or R) and the viscous properties of the lubricant. The sliding component (S) generates heat (flash temperature) and introduces tangential strain. This strain must be accommodated by lubrication films and the near-surface material. The ability of the test apparatus to operate over a very large range of R and S, opens the opportunity to independently invoke lubrication mechanisms and failure mechanisms over an extended and continuous range. It allows the ability to simulate the kinematic conditions of a large number of tribological applications. It also allows the ability to assess the performance attributes of the structural elements within the Hertzian region with multiple pathways and continuous connections among failure modes of wear, scuffing and contact fatigue.

Figure 10:
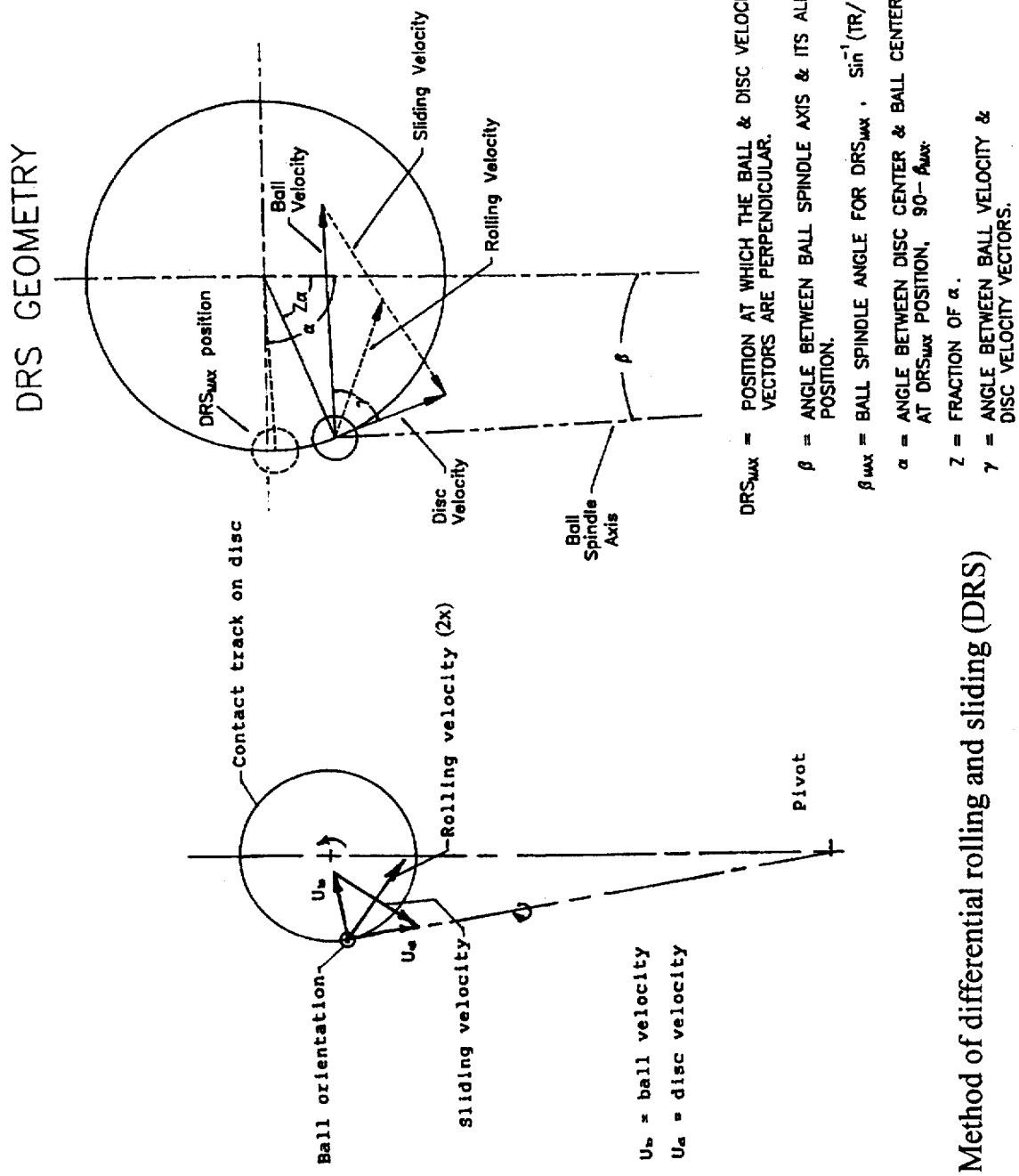
FIG. 10 shows schematically the surface velocity vectors of the test specimens, their angular relationship
Figure 11:
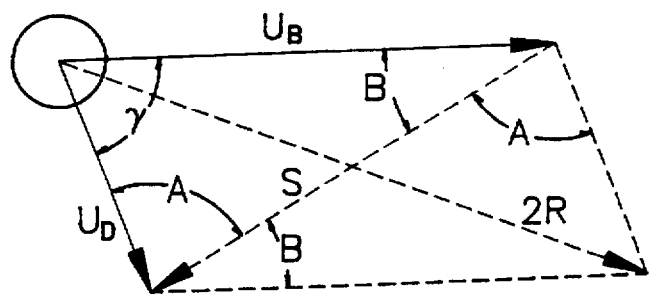
FIG. 11 shows schematically the surface velocity vectors of the test specimens and their angular relationship and their combination to form an entraining velocity vector (R) and a sliding velocity vector (S).

The preferred test configuration consists of a point contact generated between a sphere (ball) and plane (disc). An exceptionally large range of R and S values is obtained by controlling ball and disc surface velocities as well as their directions. This method of "differential rolling and sliding" (DRS) is illustrated in FIG. 10. The resultant entraining velocity (R) is the vector sum (divided by 2) of the ball and disc velocities. The resultant sliding velocity (S) is the vector difference between the ball and disc velocities. The angle between the ball and disc velocities is allowed to vary between 0 and 90 degrees. The relationship between ball velocity ($U_b$), disc velocity ($U_d$), R and S is shown in FIG. 11.

Process of Evaluation

Performance Maps

Figure 12:
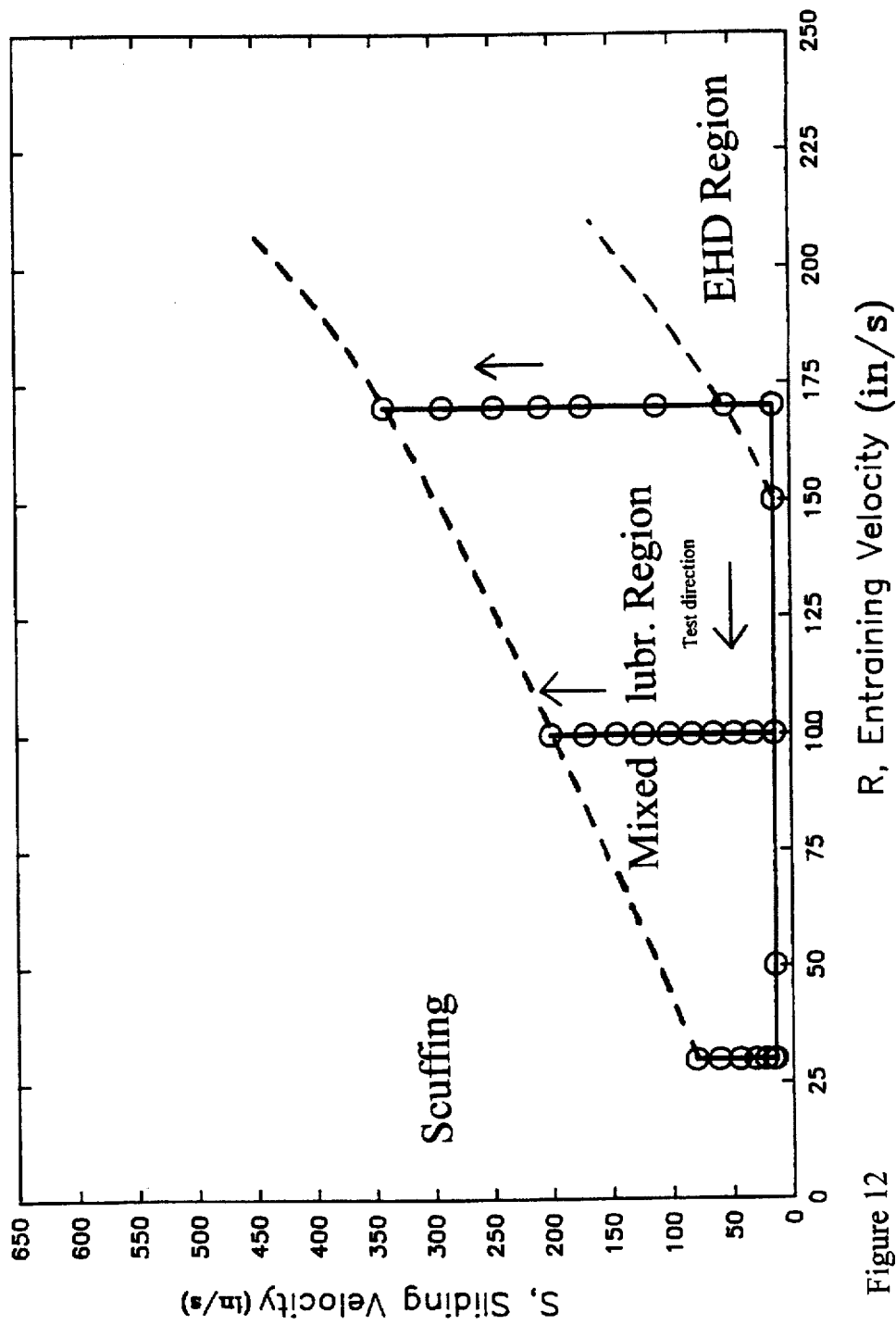
FIG. 12 is a plot of a series of tests which creates a performance map for an oil and material combination. The performance map identifies regions of lubrication and failure mechanisms.

A major feature of the present invention is the ability to develop a performance map for tribological materials. A performance map for a given lubricant and specimen materials can identify at least three major performance regions such as scuffing, mixed lubrication region and ehd region (see FIG. 12). A performance map can be created in two or more dimensions. The tribological performance of the oil, shown in FIG. 12, is given in terms of an entraining velocity (R) and a sliding velocity (S). Temperature, stress, calculated ehd film thickness and surface finish are additional dimensions that can be added to a performance map.

The entraining velocity, which is the vector sum (actually ½ the sum) of the test specimen surface velocities, is directly related to the generation of an ehd film. Ehd film generation as explained above is primarily an "inlet" phenomenon where the converging surfaces upstream of the actual contact generate the film forming pressure. Thus, the relevant oil properties for film thickness are those associated with the inlet region. Ehd theory provides a direct quantitative link between film thickness and the viscous properties of the oil (vis-temp, press-vis). The control of the entraining velocity thus provides a very precise control of surface separation.

The sliding velocity (S), which is the vector difference between the test specimen surfaces, is primarily felt within the contact (or Hertzian region). The Hertzian region must accommodate the tangential shear caused by the relative slip between the surfaces. If the entraining velocity generates a "full" film between the surfaces, the shear is accommodated by the bulk film, the traction behavior of which is totally characterized by the process described above. Under typical high pressure Hertzian contacts (bearings/gears) the oil becomes pseudo-solid and the shear stress (or traction) reflects the limiting shear stress of the solidified oil. The friction or traction increases surface temperature (flash temperature) in the contact as well as the bulk temperature of the test specimens. As the sliding velocity increases, the ehd mechanism will have to be supported by boundary lubrication mechanisms to prevent wear, contact fatigue or catastrophic failure (scuffing).

The present invention has the unique ability to independently control both the entraining velocity (R) and the sliding velocity (S). A "point" (or circular) contact allows the direction of the sliding velocity vectors to change without changing the total distance traveled through the contact. The independent control of the entraining velocity and the sliding velocity vectors allows the invention to de-couple the film generation in the inlet region (where viscous properties of the oil are important) from the shear accommodation within the Hertzian region (where traction and boundary film properties are important). Thus, the entraining velocity generates an ehd film for controlled surface separation, and the sliding velocity generates a thermal and shear environment that can follow carefully designed pathways for performance evaluation.

Tests conducted over a large range of R and S allow the development of a performance map which can identify at least three regions as shown in FIG. 12: (1) the ehd region, where ehd film generation is sufficient to separate the surfaces—no wear; (2) the mixed film region where ehd and boundary lubrication mechanisms control wear and prevent scuffing; and, (3) a scuffing or severe wear region which identifies operating conditions to be avoided for normal use.

Figure 13:
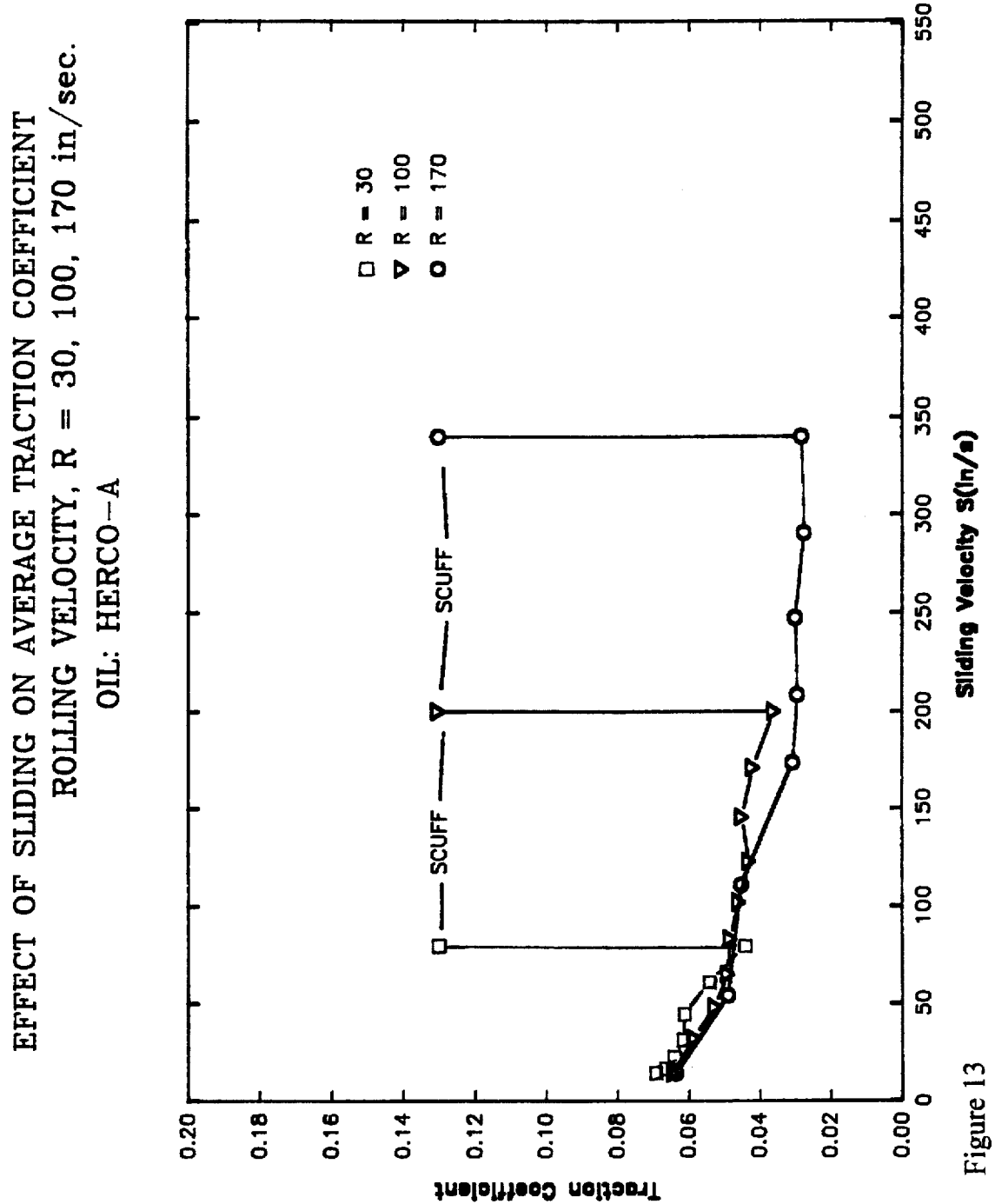
FIG. 13 shows plots of the traction coefficient for the series of tests that created the performance map.

The performance map identifies lubrication and failure regions characteristic of the particular lubricant and materials used. A performance map is created by running a series of tests that identify the transition boundaries between: (1) ehd and mixed film lubrication, and (2) mixed film lubrication and (3) scuffing. In this case, each data point is a 10 minute test, run at a constant stress (300 ksi) at selected values of R and S. The apparatus provides the traction coefficient for each test. The measurement of traction coefficient as plotted in FIG. 13 provides a means to predict hem generation and frictional loss calculation of the tribo-contact system. The decrease in traction and its departure from a linear relation with sliding velocity or measured specimen temperature provides a measure of the frictional contribution of boundary films and surface roughness.

The performance map is obtained, for example, by running four test series; one at constant S and varying R, and three at constant R and varying S. The ehd/mixed lubrication transition is determined by microscopic inspection of the ball and disc surfaces for an observable change in surface finish. The apparatus allows real-time visualization of surfaces to detect this transition. This transition can also be determined by the actual measurement of film thickness with optical interferometry down to less than one quarter wavelength of light. The mixed film/scuffing transition is determined by a sharp increase in traction along with a complete loss of surface integrity (scuffing). The locations of the two transitions reflect the physical and chemical performance properties of the lubricant.

The performance of a tribo-contact system can be mapped out with a series of performance maps that cover a range of conditions of practical interest. Detailed evaluations in terms of wear, traction and contact fatigue can be conducted within the operating regions defined by the performance map. The multi-dimensional character of performance maps and the additional evaluations that can be conducted within the various regions allows the impact of new technologies to be assessed with respect to operating conditions and competitive failure modes. An example of the invention for anti-wear performance is given.

Anti-wear Performance

Many practical applications operate in the mixed film lubrication regime where the surfaces encounter wear, especially during the initial stages of running. Wear is reduced by the formation of surface films. The performance of the lubricant, under mixed film lubrication, is a function of its "anti-wear" behavior.

Figure 14:
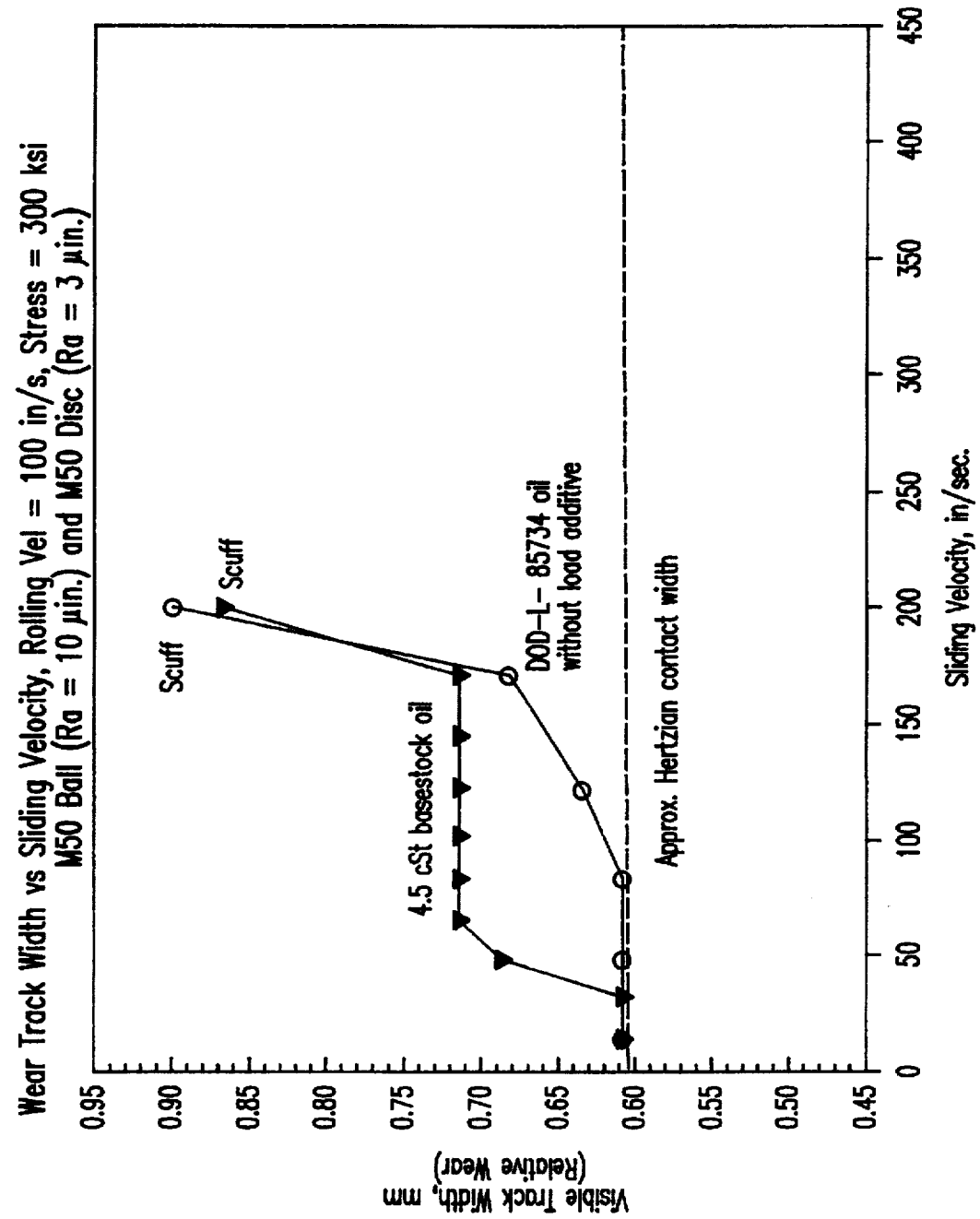
FIG. 14 shows the wear performance and scuff performance of two oils where the DODL 85734 oil has an anti-wear additive.
Figure 15:
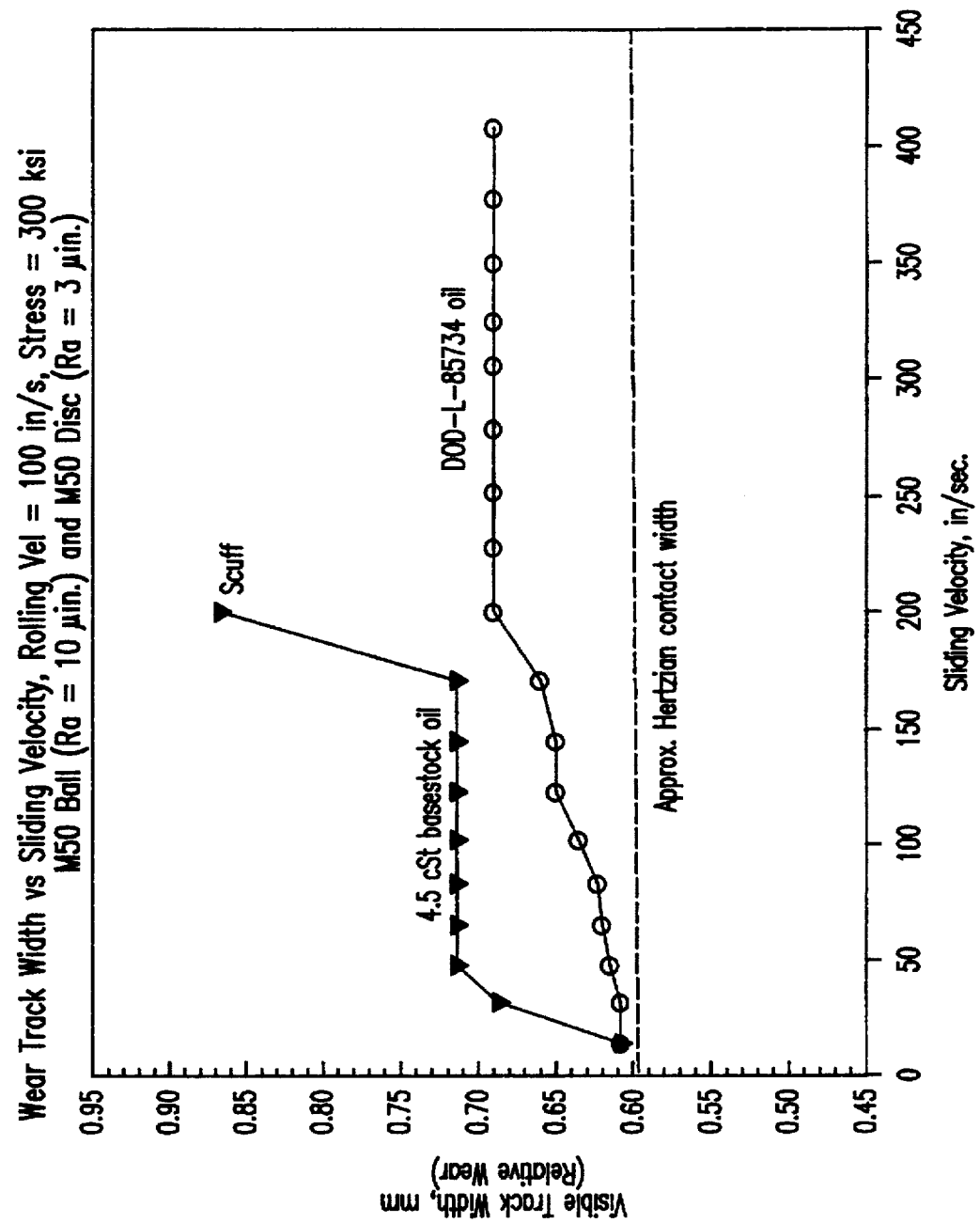
FIG. 15 shows the wear performance and scuff performance of two oils where the DODL 85734 oil has an anti-wear additive and a load carrying additive.

The process of creating a performance map also serves as a means to obtain the anti-wear performance of an oil. This is accomplished by precise measurement of the track width or profile trace on the ball or disc after each 10 minute test. The change in track width due to wear is shown in FIGS. 14–15. The track width is plotted as a function of sliding velocity for three ester base oils: (1) unformulated oil (Herco-A), (2) anti-wear additive only (DOD-L-85734 w/o LA) and (3) fully-formulated oil with both anti-wear additive and EP additive (DOD-L-85734). The process of the present invention characterizes the oils by showing that an anti-wear additive can reduce wear, but it does not increase the scuffing load capacity of the oil. The fully formulated oil (DOD-L-85734) reduces the amount of wear and also increases the load carrying capacity (scuffing boundary).

The optical measurement of film thickness using interferometry, along with the above test methodologies, provides opportunities to perform a comprehensive evaluation of oil performance. This includes the measurement of fundamental properties like pressure-viscosity coefficient which is needed for design and performance prediction.

The measurement of surface wear while conducting a series of tests through the mixed film region provides a means to obtain the anti-wear performance of an oil as shown above. Alternative methods, such as using bulk temperature or inlet starvation as a means to increase contact severity, can also be used to assess anti-wear performance, as discussed above. However, the creation of a performance map and the operation of a test series into and through the regions of the map have been found to be essential for the performance evaluation of an oil and how it relates to materials and operating conditions actually used in service.

In practice, the present invention should recognize two important considerations in the evaluation of tribological performance.

First, when evaluating the boundary performance of lubricants to reflect their anti-wear and scuffing attributes, the pathway and severity of conditions that are taken to measure performance has a very significant influence. A gentle and gradual transition into the mixed film lubrication regime, which allows ample time for "run-in" to occur, will result in much different performance than a test series where a more aggressive transition and pathway is taken. Performance can be very process dependent with regard to test methodology. In the same way, in-service performance is very component and user dependent. For this reason, the testing pathway and severity used in the methodology must be in line with typical service conditions. The wide range of operating parameters, particularly R and S, serve to simulate the operating conditions of component hardware.

Second, the present invention illustrates that the lambda ratio of film thickness to surface roughness frequently used is not always a common denominator. The absolute value of roughness and the topographical "lay" are very important. Smooth polished surfaces "scuff" more easily than surfaces with significant surface features. On the other hand, rough surfaces scuff more easily than surfaces that are less rough, so long as they are not polished. The invention illustrates that a contact which is operating with an appropriate degree of micro (asperity) lubrication along with a supporting macro (ehd) film can obtain a remarkable degree of durability. This combination can be achieved by "run-in," provided the initial surface finish is not too rough so that the regions between asperities can become pressurized by ehd (or micro-ehd) action. For this reason, the test apparatus of the present invention is designed to accommodate multiple materials and surface topographical features.

Direct Linkage to Hardware Application

The multi-dimensional characterization of tribological materials by way of performance maps, or other selected pathways, allows a direct link to hardware applications. The ability of the invention to accomplish this is significant in regard to a meaningful evaluation for the development of tribological materials and trouble shooting hardware problems. The ability to predict performance avoids the time and costly process required to build and test full-scale hardware.

Figure 16:
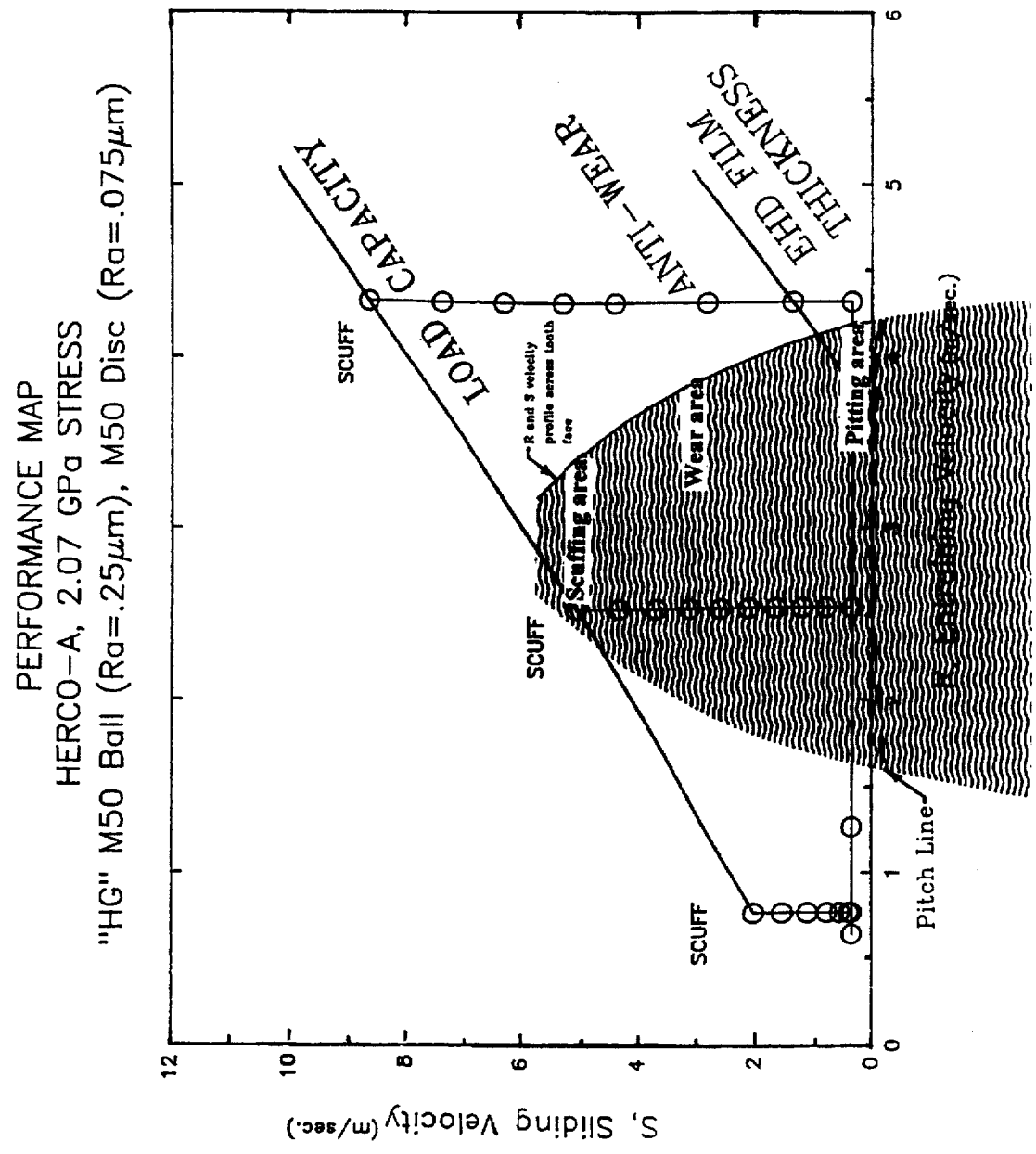
FIG. 16 shows how the generation of a performance map using entraining velocity and sliding velocity parameters can be connected to the operating conditions across a gear tooth face.

A preferred embodiment of a multi-dimensional performance map utilizes the tribologically significant parameters of entraining velocity and sliding velocity. Lubricated contacts of bearing and gears have specific kinematic relationships between entraining and sliding velocities which are derived from their design geometry and operation conditions. The contact between two gear teeth, for example, encounters a range of rolling and sliding velocities from the point of engagement to the point of disengagement. The absolute values of these velocity conditions can be translated onto a performance map shown schematically in FIG. 16. In this way, the lubrication or failure regime (ehd, mixed film or scuffing) across a tooth face can be identified along with the anticipated anti-wear, scuffing or ehd performance. For a spur gear contact, the sliding velocity is zero at the pitch line and maximum at the tip or root of the gear tooth. The lubrication and wear conditions across the tooth face are identified by the regions within the performance map. In this case, high sliding velocities and low entraining velocities are seen to be near the scuffing boundary at the gear tooth tip. With the use of a load carrying or "EP" additive, the scuffing boundary can be moved up. The process and apparatus quantifies the performance margin.

Figure 17:
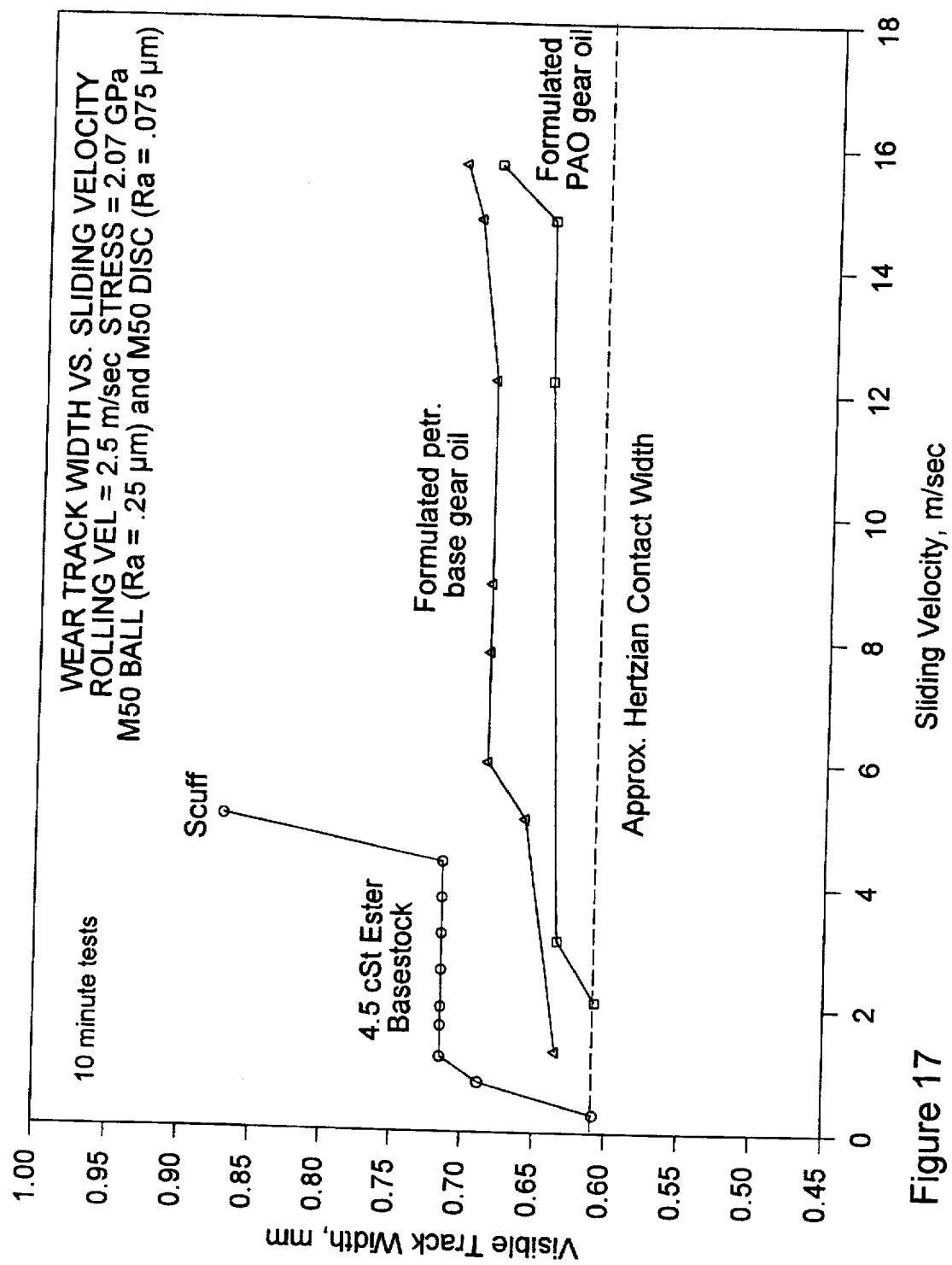
FIG. 17 shows the simulated wear expected across the face of a gear tooth for three oils.
Figure 18:
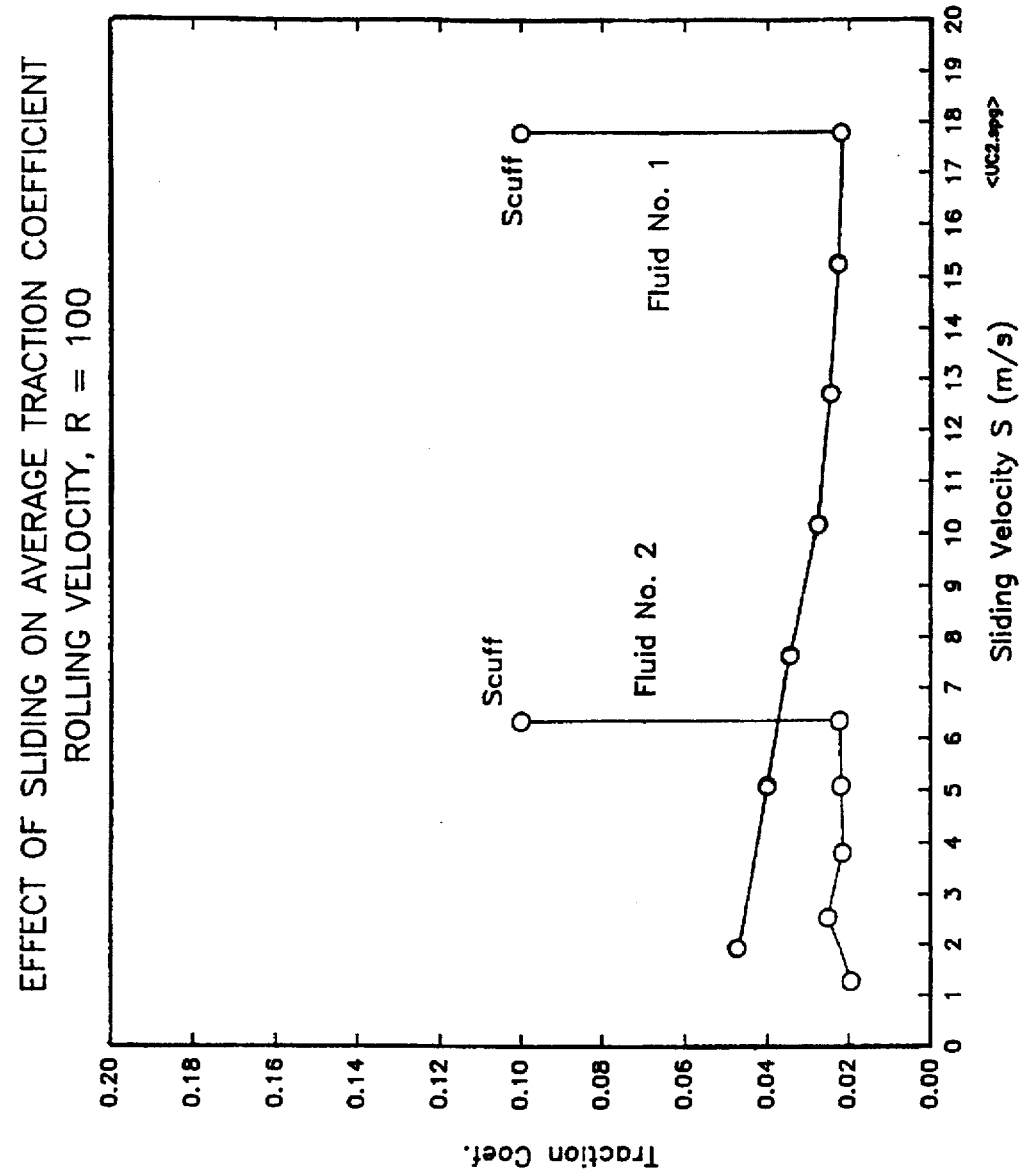
FIG. 18 shows the difference between the traction coefficients of two types of oils as a function of sliding velocity. The low friction oil has limited load capacity.

Wear and contact fatigue (pitting or frosting) can also be evaluated by long term operation within the specified regions of the performance map. The multiple operating conditions which can be simulated across the tooth face, maps out the performance covering scuff limited operation, wear and contact fatigue. An example of simulated tooth face wear for three oils is shown in FIG. 17. An example of simulated tooth face efficiency for two oils, as reflected in traction coefficient, is shown in FIG. 18. The performance across the tooth face, as simulated by the apparatus and process, differentiates the impact of boundary films from additive interactions that control anti-wear performance and the simultaneous and interactive process of surface initiated contact fatigue. The invention quantifies the tangential shear stress by way of the modifications in traction coefficient due to surface films. The surface traction in the tribo-contact translates to contact fatigue life. The invention simultaneously quantifies wear as a competitive and interactive process. The competition between these two processes are generally unknown, but critical to hardware performance.

Figure 19:
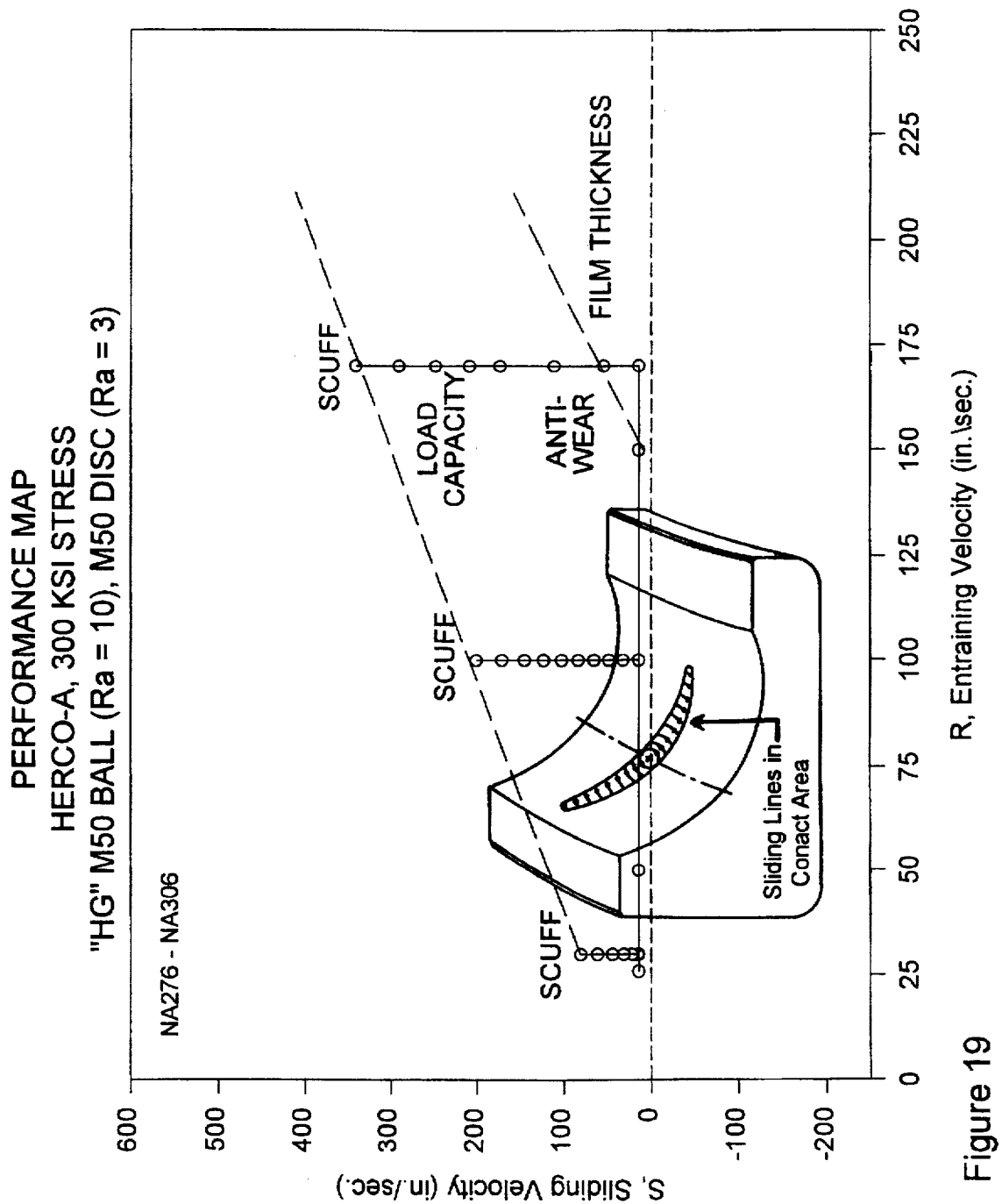
FIG. 19 shows schematically how a performance map generated in terms of entraining velocity and sliding velocity can be translated to the contact interface of bearing hardware for performance prediction.

In a similar fashion, the contact kinematics within a rolling element bearing can be translated on to a performance map and simulated over a practical range of operating conditions. This is shown schematically in FIG. 19.

Process of Evaluation

Determination of Activation Temperature

Figure 20:
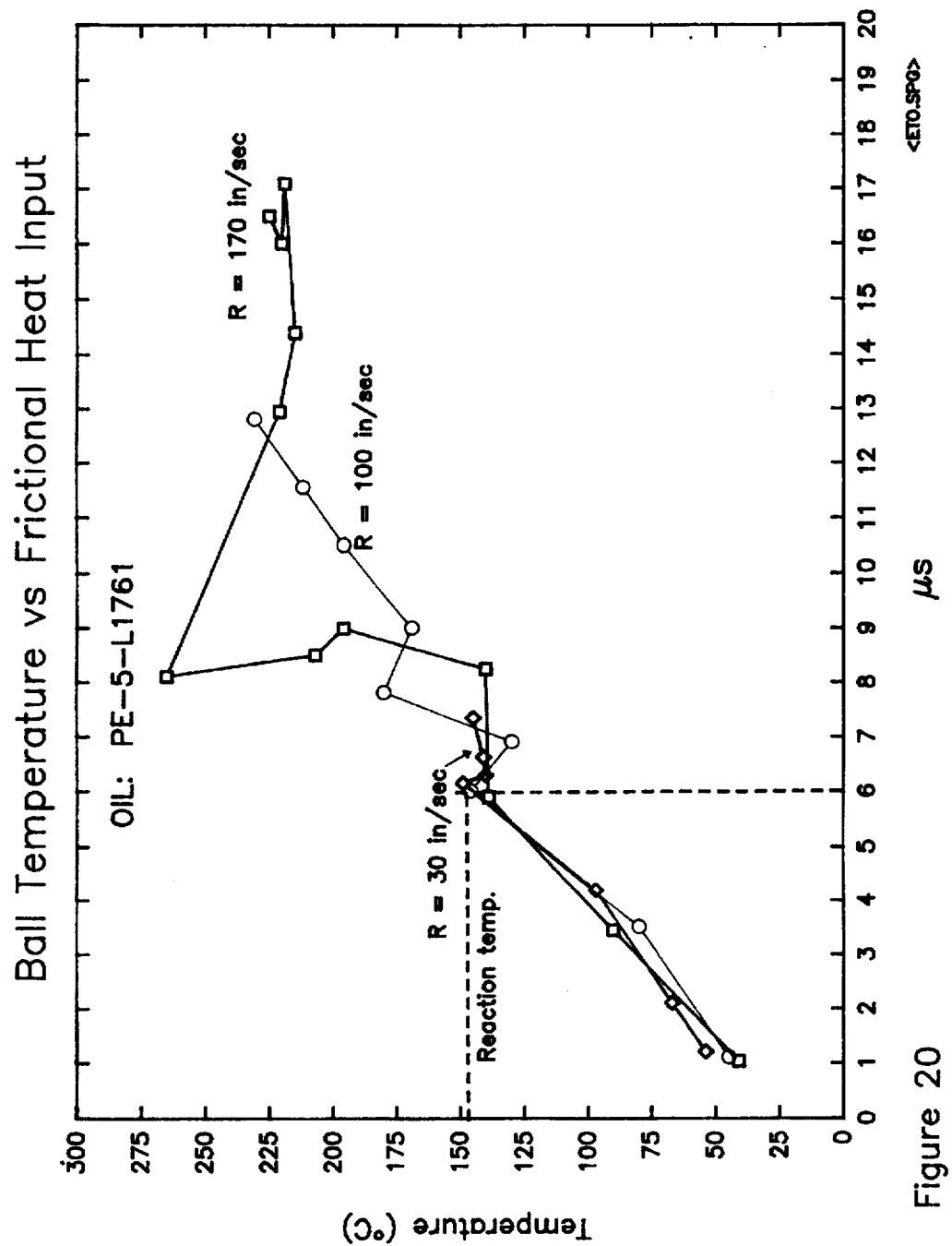
FIG. 20 shows a transition at 140° C. in the relationship between the frictional heat input into a tribo-contact and the measured specimen temperature. The transition is due to endothermic and exothermic chemical reactions of boundary film additives. The operating conditions and surface temperature for the additive reaction, as determined by the invention, provides an opportunity to connect the oil formulator's product to hardware performance.

The process of creating performance maps, or any hardware simulation where the testing pathway invokes chemical interactions, can be used to determine the reaction temperatures of oil chemistry. The apparatus provides a continual measurement or control of operating parameters, including traction coefficient, sliding velocity and specimen temperatures. These parameters can be used to determine the frictional heat input into the tribo-contact. The response to the frictional heat input is a rise in specimen temperature which is precisely measured. The relation between frictional heat input and specimen temperature is linear. A departure from this linear relation is due to endothermic or exothermic reaction within the tribo-contact. An example of this for three test series with the same oil is shown in FIG. 20. The operating conditions (particularly temperature) which produce these reactions are important for the oil formulator and the hardware user to design or utilize the proper additive chemistry. The example in FIG. 20 shows a reaction temperature of 140° C. The temperature so determined is the bulk temperature outside the tribo-contact. The temperature of importance is the total temperature within the tribo-contact that activates the chemical reaction. The apparatus, in real time, provides the calculation of this temperature as the sum of the bulk temperature ($T_b$) and the flash temperature ($T_f$). The flash temperature is determined from the measured traction coefficient, sliding velocity and the assumed or measured thermal properties of the tribo-contact materials.

Since the apparatus can provide real-time microscopic video monitoring and recording of the surfaces outside the tribo-contact, the formation and removal process of surface films can be monitored. The large operating range of the apparatus allows the mapping of the conditions between which the surface films are formed and removed. The mapping can also be accomplished along a pathway that simulates component hardware. The simulation is a mechanistic simulation, where the same lubrication and failure mechanisms found in component hardware are simulated, both in form as well as sequence.

Because of the flexibility and range of operating conditions of the apparatus and the ability to provide hardware simulation, the reaction temperatures so determined can be directly used to predict the onset of chemical boundary film formation in component hardware.

This data is critical for determining the appropriate additive reactivity from mild anti-wear behavior to highly reactive load carrying behavior.

PREFERRED EMBODIMENT OF APPARATUS

The purpose of the apparatus is to control and monitor a tribological contact. The apparatus is capable of controlling the sliding velocity, rolling velocity, contact stress and bulk temperature of the specimens independently while being able to measure the contact force in three directions. The bulk temperature of the specimens, the lubricant film thickness and the specimen wear are also controlled. The apparatus is unique in what it does and the manner in which it does it.

Figure 21:
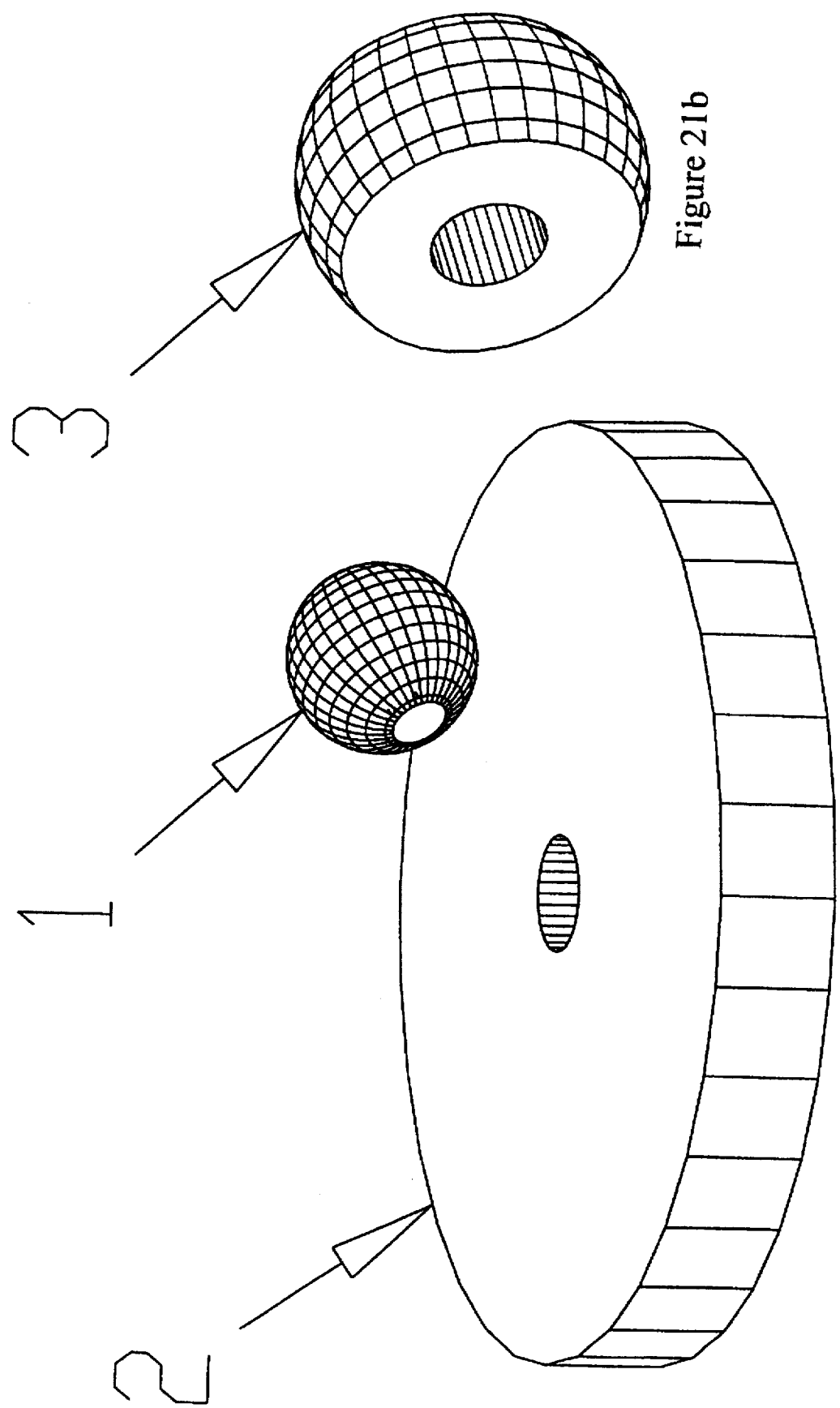
FIG. 21 shows the preferred geometry for the specimens used in the apparatus.

The preferred embodiment of the contact surfaces comprises a ball and a disc specimen, which are shown in FIG. 21. Both the ball specimen (item 1) and the disc specimen (item 2) have a hole that allows them to be mounted to spindles and rotated about the axis of the hole. The disc is normally fabricated from bar stock to the required size and finish from the desired material. The planar surface of the disc is the contacting surface for the tests, as opposed to the edges. The discs are normally ground with a carefully controlled surface finish such that the grinding lay leaves ridges concentric to the mounting hole. The discs can be mounted and run on either planar surface.

The ball is normally intended for use in a ball bearing. The ball is modified by adding the mounting hole. The ball can be a smooth finished ball like those used for ball bearings. A ball that has not been finished ground by a manufacturer is a rough ground ball. This rough ground ball, also referred to as a hard ground ball, can be used when a rougher surface finish is desired. The balls are normally available in commonly tested materials and can be plated or surface treated in several ways. As an alternative to the ball specimen, a crowned roller specimen is shown in FIG. 21 (item 3). The crowned roller can be used when ball specimens are unavailable. The crowned roller specimen allows freedom to choose any material or finish, which may be difficult to obtain from a ball manufacturer.

Figure 22:
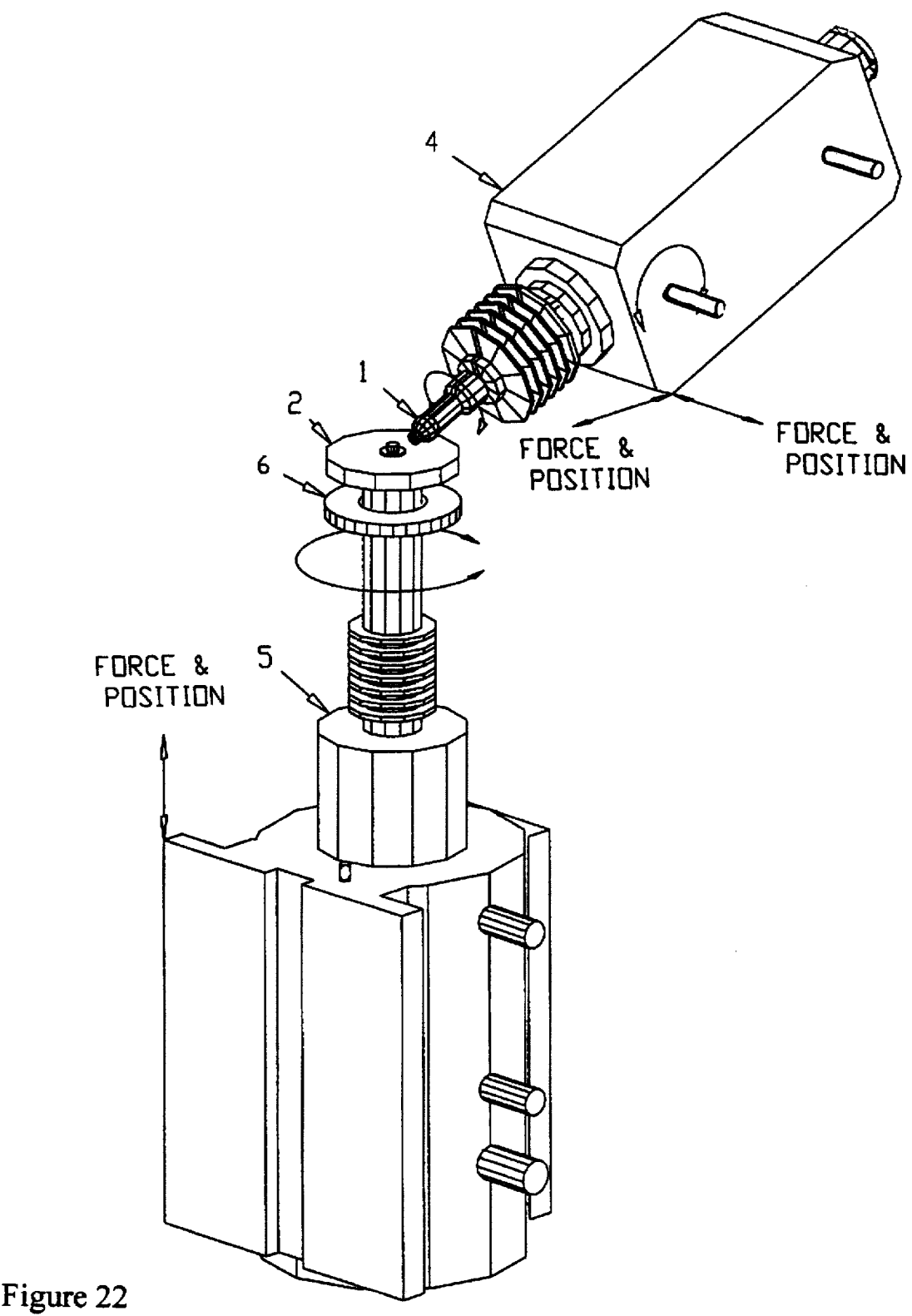
FIG. 22 depicts the major components of the apparatus.

While the fabrication of the specimens determines the materials and finishes of the contact, the specimens must be mounted in the apparatus to achieve the kinematics part of the simulation. FIG. 22 shows the specimens mounted on spindles, which are capable of rotating the specimens about their respective mounting hole axis. The ball specimen (item 1) is mounted in the ball spindle (item 4). The disc specimen (item 2) is mounted in the disc spindle (item 5). Both spindles have built-in electric motors. The motors are servo controlled using external electronics, which are standard off-the-shelf components. These electronics allow the spindles to be precisely controlled in regard to rotational position, angular velocity and angular acceleration, although the primary focus is on angular velocity. It is possible to tie one spindle to the other electrically so they are essentially geared together. Furthermore, the position of the specimens can be moved to change the orientation of the velocity vectors of the two specimens.

Figure 23A:
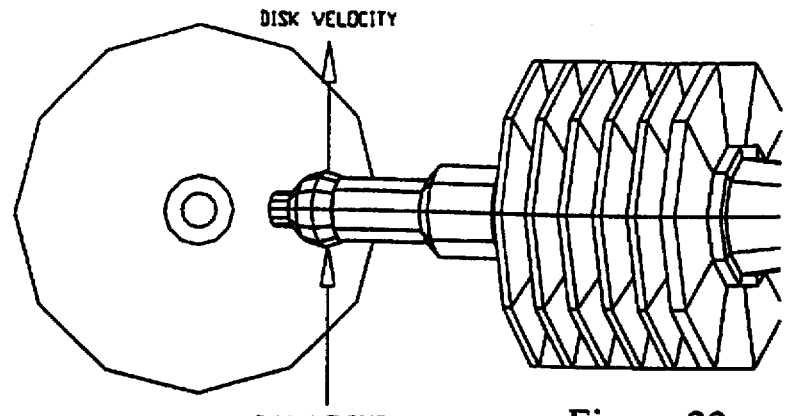
FIGS. 23A–23C illustrate how the velocity vectors are oriented in relation to the apparatus components.
Figure 23B:
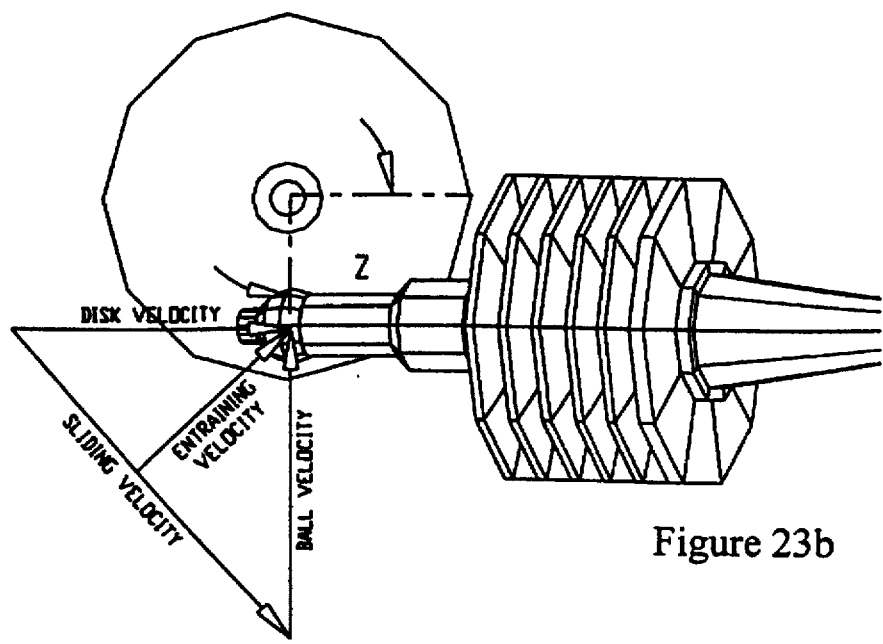
Figure 23C:
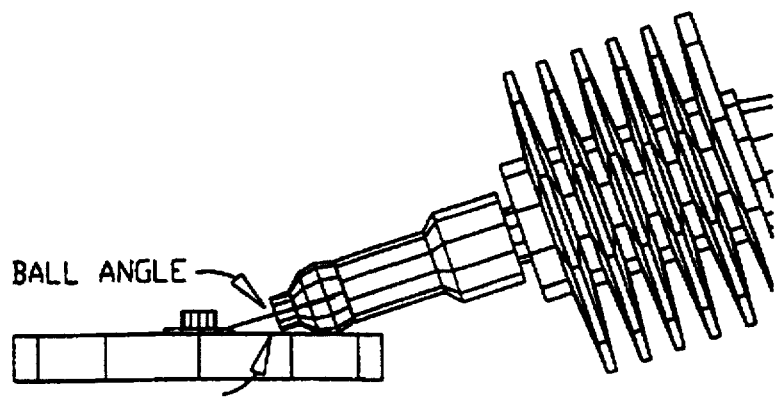
Figure 24A:
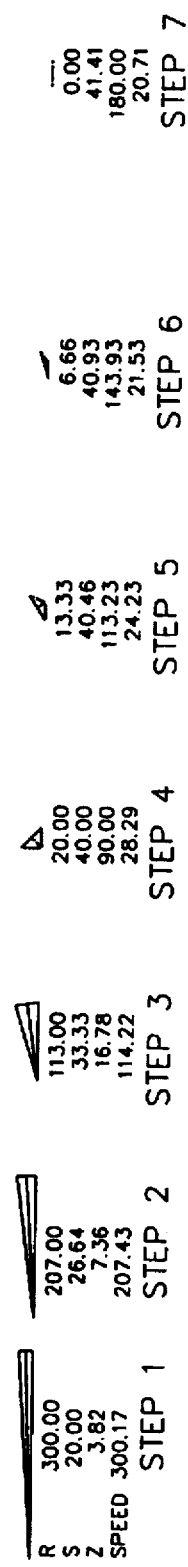
FIG. 24 shows various combinations of velocity vectors in terms of the kinematic parameters.
Figure 24B:
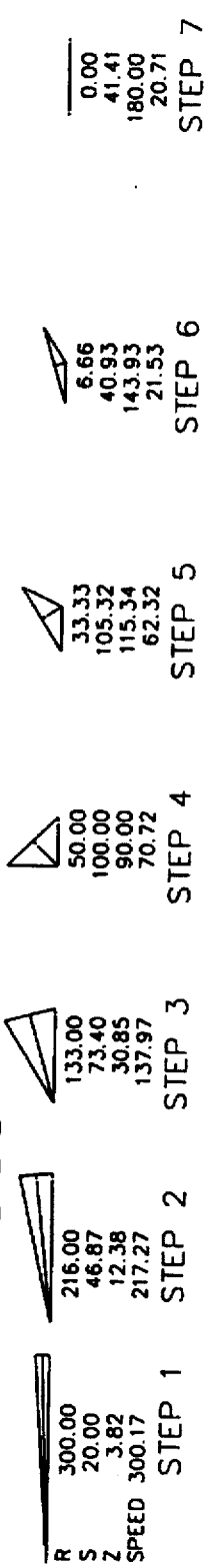
Figure 24C:
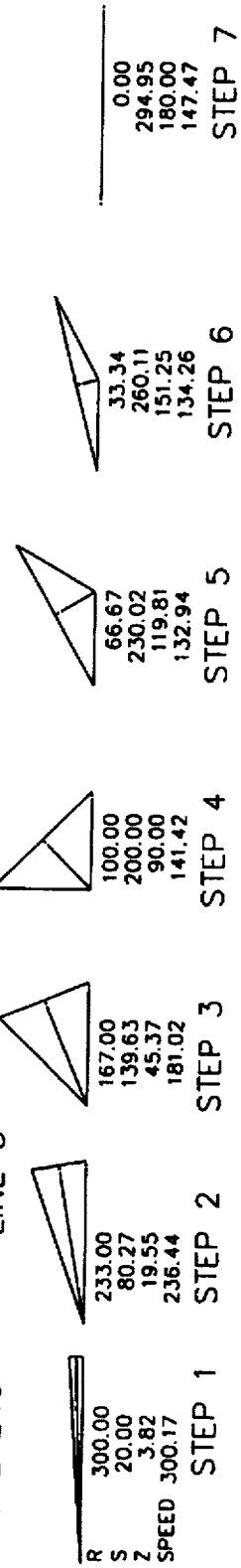
Figure 24D:
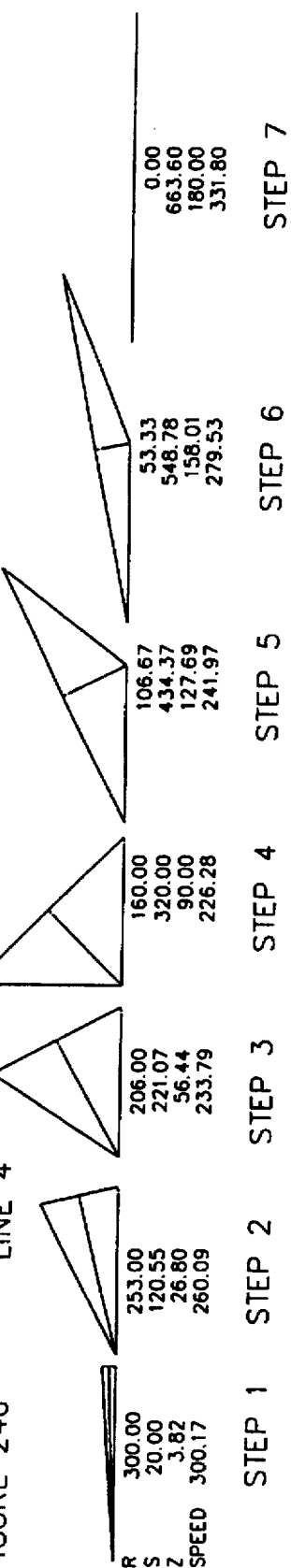

FIG. 23A shows the plan (top view) of the two specimens mounted in the spindles. The two spindles are aligned so that the velocity vector of the ball at the point of contact is collinear with the velocity vector of the disc at the point of contact. When the spindles are positioned as shown, they are said to be in the aligned position. The surface speed is defined as the rotational speed times the circumference of the specimen at the point where contact is being made. The circumference of the disc (disc track diameter) is picked arbitrarily by where the operator places the ball on the disc when the apparatus is setup. The circumference of the ball specimen at the point of contact is defined by the diameter of the ball and the angle at which it is tilted. A side view of the apparatus is shown in FIG. 23C. This illustrates the tilting of ball or the "ball angle." The ball angle is selected such that the ball axis of rotation, when in the aligned position, intersects the disc plane of contact and its axis of rotation. Mathematically:

ball angle=$TAN^{-1}$ (ball diameter/disc track diameter)

Aligning the ball in this manner allows the apparatus to wear the ball in the shape of a cone. This allows the "cone" to have the same ratio of diameters with respect to the disc at all points of contact. The ball tilted at such an angle requires the ball track diameter to be calculated as the basic ball diameter times the cosine of the ball angle.

When the apparatus is in the aligned position, the entraining velocity is the average of the ball surface speed at the contact and the disc surface speed at the contact. The sliding velocity is the difference between the two velocities. If the ball speed is the same as the disc speed, there is no sliding velocity and the contact is in pure rolling. The speeds of each spindle can be set at any speed from zero to the maximum of the respective spindle. The equation for the kinematics in the aligned position is as follows:

Entraining Velocity=(ball velocity+disc velocity)/2

Sliding Velocity=(disc velocity−ball velocity)

By using the two equations, it is possible to solve for the ball and disc velocities for a desired set of entraining and sliding velocities. Higher sliding velocities can be achieved by reversing one of the spindles to achieve a negative velocity.

Although a large range of speeds is theoretically possible in the aligned position, some combinations yield ball and disc speeds that may not be desirable. One example of this would be when one specimen is rotating at very high speed and the other specimen is either stationary or rotating at a very slow speed. To overcome this problem, the apparatus allows the angle of the velocity vectors to be changed by moving away from the aligned position. FIG. 23B shows the ball positioned over the disc such that its velocity vector is perpendicular to the disc's velocity vector. The figure also shows the disc velocity vector at the point of contact, the ball velocity vector at the point of contact, as well as the angle between them (Z). Also shown is the entraining velocity, which is one half the vector sum of the ball and disc velocities. The sliding velocity is shown as the vector difference between the disc velocity and the ball velocity. The ability to vary Z between 0° and 180° greatly increases the possible solutions to the values for the ball and disc velocities for a given set of entraining and sliding velocities.

Figure 25A:
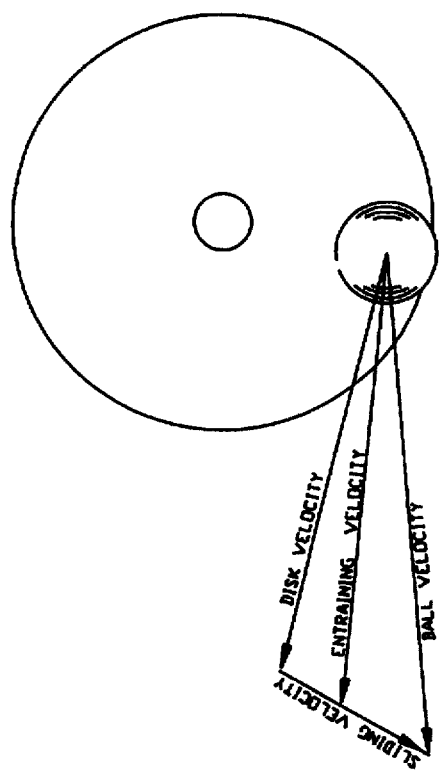
FIGS. 25A–25C show how the velocity vectors are changed to increase entraining velocity keeping sliding velocity constant. It also shows how the sliding velocity can be changed keeping entraining velocity constant.
Figure 25C:
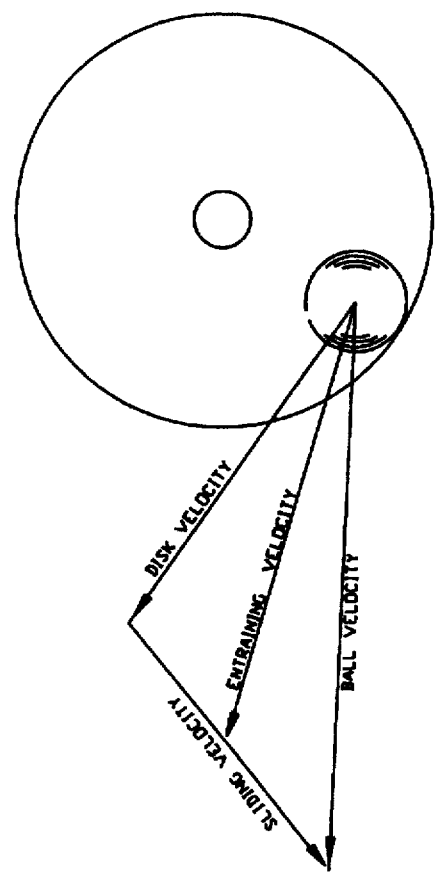
Figure 25B:
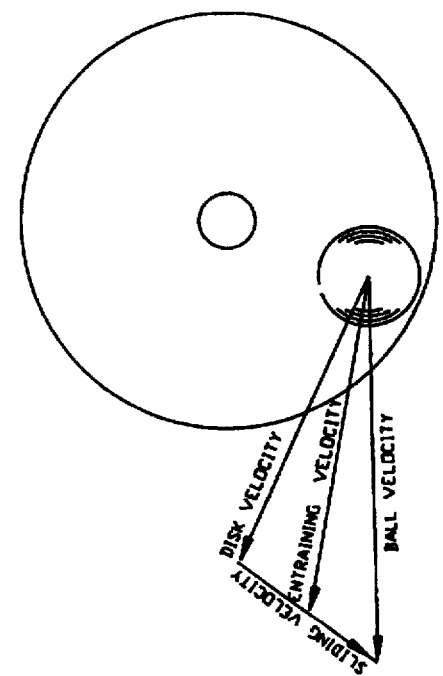

FIG. 23B shows a rather simple case where the ball velocity equals the disc velocity and they are at right angles to each other. FIG. 24 shows some of the possible variations. The figure also shows a table where the rows are labeled R (entraining velocity), S (sliding velocity), Z (angle between ball and disc velocity vectors) and the surface speed of the specimens. In this example the ball and disc speeds are equal. The seven columns show various combinations and the vectors shown graphically. FIG. 25 shows how it is possible to start at an arbitrary entraining and sliding velocity and change one with out changing the other or the angle between them. The progression from FIG. 25A to FIG. 25B shows how the ball and disc velocities can be changed to achieve a smaller entraining velocity with the same sliding velocity. Changing from FIG. 25A to FIG. 25C shows how the ball and disc velocities can be changed to increase the sliding velocity while maintaining the same entraining velocity.

Besides being able to control the kinematics of the specimens, the apparatus is capable of controlling the bulk temperature of the specimens using heaters. The preferred method of heating utilizes electric resistance heaters. One configuration uses a tubular heater under the disc shown as item 6 in FIG. 22. A second configuration utilizes cartridge heaters in blocks of metal to form a heated chamber. Either case, the preferred method of heat transfer is convection. The heaters are controlled using standard PID temperature controllers.

The lubricant between the contacting surfaces may be a liquid, solid or vapor that is introduced into the contact in a variety of methods. The normal configuration is for the lubricant to be dripped 224 into the contact using a peristaltic pump 222. The lubricant may be run through the contact once and disposed of or recirculated through with the use of a sump that catches the excess lubricant. The flow of the lubricant in the preferred embodiment is varied by changing the speed of the lubricant pump.

The disc spindle (item 5) and the disc specimen (item 2) are moved vertically, as indicated in FIG. 22, while the ball and ball spindle are held fixed in the vertical direction. In the configuration shown, the disc is moved up to come into contact with the ball. Once the contact is loaded, further movement of the disc in the upward direction causes increased contact force. In the preferred embodiment, the disc is moved by an electrical actuator driven by a stepper motor.

In addition to providing the proper kinematic conditions, bulk temperatures, contact load, specimens and lubricant, the apparatus can measure the contact forces. Forces are measured using load cells located in all three directions. The ball spindle (item 4), shown in FIG. 22, is mounted on low friction bearing so that it is free to move in the plane of the disc. The preferred method of achieving low friction is through the use of air bearings to support the ball spindle in the vertical direction. This results in load cells being the only force counteracting the frictional forces of the specimens. The load cells are aligned so that they are either parallel or perpendicular to the ball axis of rotation when it is projected into the plane of the disc. The load cell, which is parallel to this projected axis of rotation, measures axial forces on the ball. Two load cells in the perpendicular direction measure the side forces. By keeping the load cells so aligned, it is possible to distinguish between axial and side forces. Under each air bearing, which is supporting the ball spindle, is a load cell oriented vertically. These load cells are used to measure the vertical force on the contact. The vertical load is simply the sum of the vertical forces. The contact load is the loaded vertical force less the tare of the unloaded vertical force.

The specimens start with a defined geometry, which is relatively simple. Almost all changes to the geometry of the specimens during operation are attributable to wear. The specimens are normally run such that the points of contact on the specimens are concentric with the axis of rotation. When wear occurs, it is normally on a track that is concentric with the specimen's axis of rotation and the same width as the contact diameter. Since the contacts are nonconformal in nature, it is possible to judge the amount of wear by measuring the width of the wear tracks on the specimens.

This wear may be measured in various ways. One method is to measure the wear track width of the specimens optically. This can be done with the naked eye or aided by optical equipment. Optical magnification using a microscope or camera helps with both measuring the size of the wear track, as well as to make judgments on the condition of the surface. This can be done while the apparatus is operating, particularly, when stroboscopic light is used. The specimens can also be studied away from the apparatus when they are cleaned of lubricant, which may hinder optical observation. The specimen wear is also measured and qualified using stylus trace instruments.

The bulk temperature of the specimens is measured using small gage open wire thermocouples, such as 226, 228, in FIG. 22, which are allowed to ride lightly on the specimens near the contact area. Infrared measurement is also done, but the problem of lubricant getting on the instrument's optics makes this complicated to implement and operate.

Figure 26:
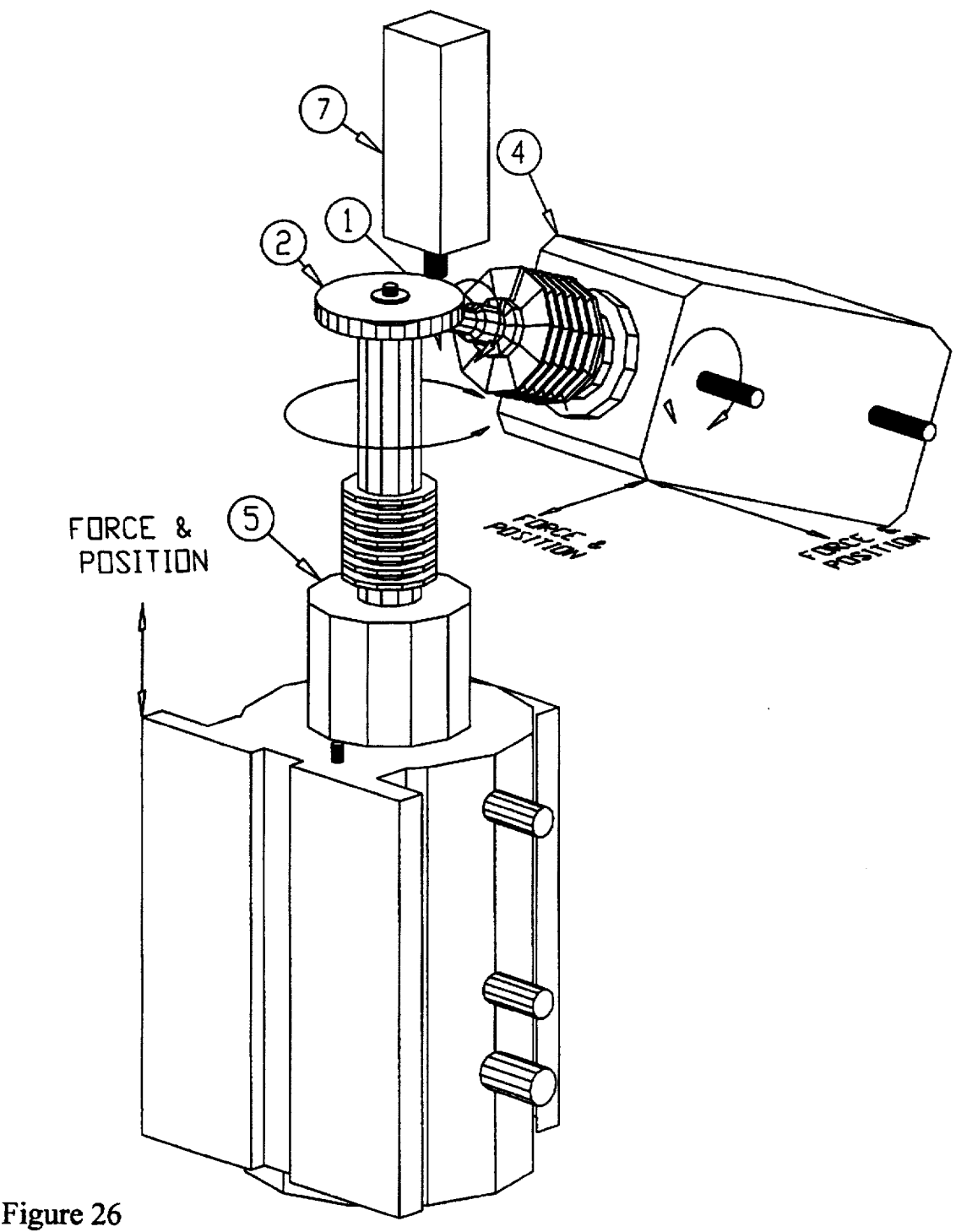
FIG. 26 pictures the major components configured for interferometry.

Lubricant film thickness is measured using interferometry. A disc made from an optically clear material such as glass or quartz is coated with a partially reflective material and mounted in the disc spindle. The machine is setup using the same configuration as previously described except that the ball is below the disc to allow the placement of a microscope above the disc to view the interference patterns. The configuration of the disc above the ball is shown in FIG. 26. With the disc above the ball a camera, microscope (item 7) or other optical device can be mounted above the disc and look through the disc and measure the film thickness between the specimens.

Figure 27:
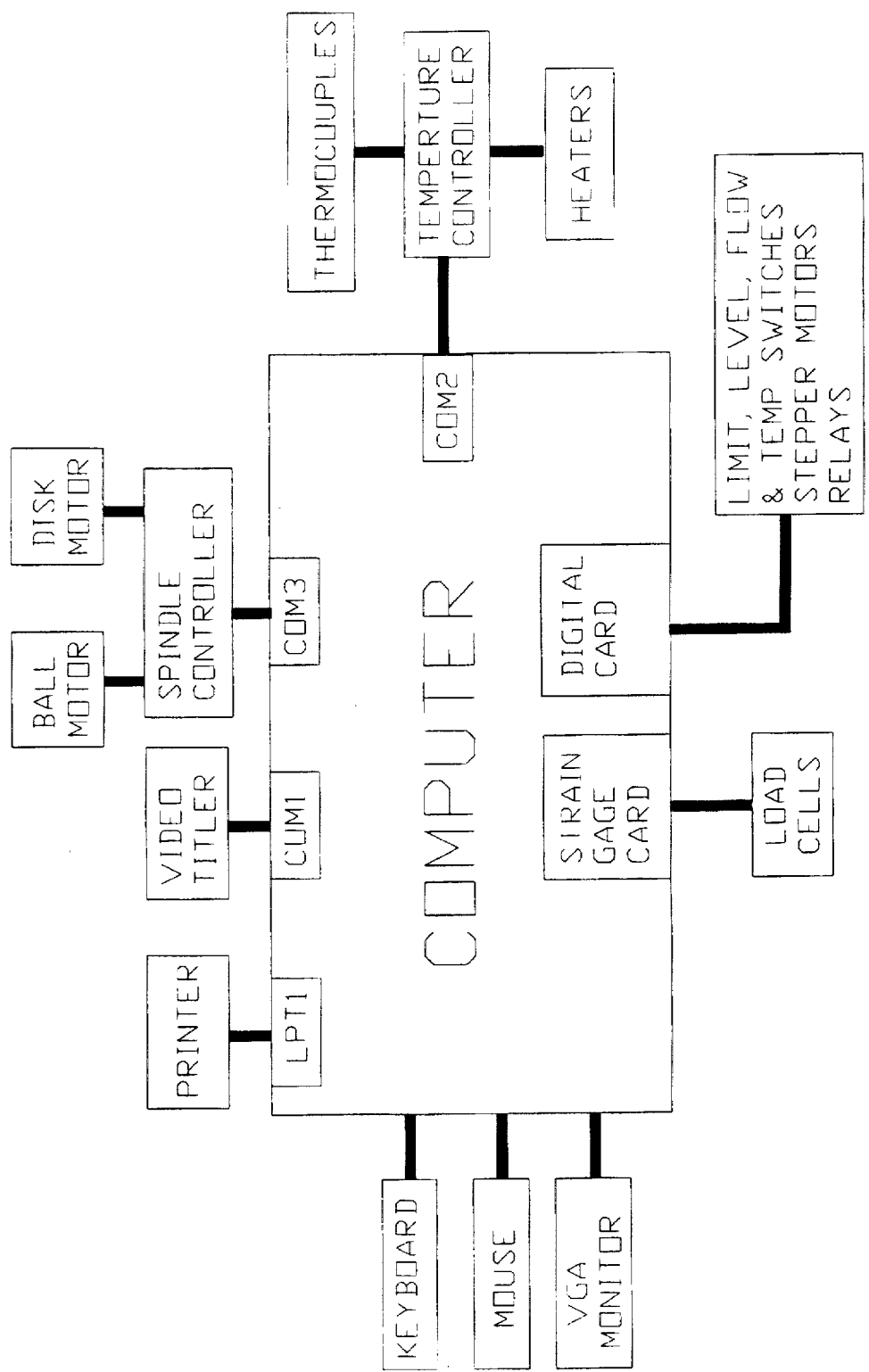
FIG. 27 diagrams the computer system which is part of the apparatus.

To operate the apparatus a fair number of mathematical calculations are needed to translate between the tribological parameters and the fundamental machine movements. One example is the relationship between the entraining velocity and the spindle speed in revolutions per minute. Almost all of these relationships can be mathematically defined and are calculated by a computer. The computer translates the user's commands to the basic machine functions. The raw data from the machine is translated into tribological data which is easily understood by the user. The computer can be any programmable computer with sufficient I/O to control the apparatus, a user display(s) and a user input device(s). A block diagram of the computer is shown in FIG. 27. The preferred embodiment of the computer system consists of standard IBM compatible computer utilizing a '486 processor. The computer has a 48 line digital I/O card, an eight channel stain gage card, four serial ports, a VGA display, a keyboard, hard and floppy drives and mouse. The computer code is written in the C language.

One function of the computer is to translate the desired entraining and sliding velocities into machine movements. The computer has control over the position of the ball in relation to the disc, as well as the rotational speeds of the two specimens. The computer can move the ball spindle in the plane of the disc using a set of stepper motors attached to lead screws. Using these motors, the computer can locate the ball in relation to the disc. One motor moves the ball spindle in the axial direction while the second moves it in the perpendicular direction. Position feedback is received from linear encoders mounted on both axes. The computer can move the ball concentric with the disc axis of rotation by doing circular interpolation. This allows the angle between the velocity vectors to be changed while still contacting the same part of the disc (staying on the same disc track). This movement can be done when the two specimens are loaded or out of contact. The computer also has control of the spindle rotational speeds. Having control of both the rotation speed of the spindles and the angle between the velocity vectors gives it complete kinematics control. The computer has been programmed with the necessary code to allow the operator to control the entraining velocity, sliding velocity and the angle between the vectors. The computer will position the spindles to the correct location and command them to the correct speed. The real power, however, is in changing the speeds in real time. Once an initial point is chosen the kinematics can be changed in several ways depending on the testing requirements. The following table shows the predominant kinematic parameters used by the apparatus.

| Term | Fundamental Parameter | Definition |
| --- | --- | --- |
| B | yes | ball surface speed at contact |
| D | yes | disc surface speed at contact |
| Z | yes | the angle between the ball and disc velocity vectors |
| R | no | entraining velocity |
| S | no | sliding velocity |
| % Slip | no | (S/R)*100 |
| Slope | yes | The ratio of change in S to the change in R. (delta S/delta R) |

All of the above kinematic parameters, except for slope, can either be changed by the operator directly or be automatically updated by the computer when a related parameter is changed. Slope can only be changed by the operator. The fundamental parameters can be changed in a deterministic way with only one possible pathway. A change to a fundamental parameter may change other secondary parameters. A change in the B will result in changes to R, S, and % Slip, assuming D and Z are held fixed. These changes are readily computed and done automatically by the computer.

The changes to the non-fundamental kinematic parameters are non-deterministic. Changes to the non-fundamental kinematic parameters can change the other parameters along different pathways depending on what conditions the operator decides. The conditions add additional constraints so that the solution to changing a non-fundamental kinematic parameter has a unique solution. One standard or commonly used condition is that the surface speed of the ball is to be as close to the surface speed of the disc. A second standard condition is that if the ball speed is not the same as the disc speed, each one should be as equally distant as possible from the average. The operator then may add addition constants such as keeping the sliding velocity (S) and the angle between the velocity vectors (Z) constant to define a unique solution. The constants can be overridden by changing one of the fundamental parameters. The table below shows some of the possible different ways to change the kinematics based on which parameters are changed, varied and held constant. The parameter to be changed is indicated by the box being marked CHANGE. If a parameter is held constant is marked "const" or "0." If the computer calculates the new value based on the other parameters it is marked "var."

| B | D | R | S | Z | % Slip | Slope |
|---|---|---|---|---|--------|-------|
| CHANGE | const | var | var | const | var | 0 |
| const | CHANGE | var | var | const | var | 0 |
| var | var | CHANGE | const | const | var | 0 |
| var | var | CHANGE | var | const | const | 0 |
| var | var | const | CHANGE | const | var | 0 |
| var | var | var | CHANGE | const | const | 0 |
| var | var | var | const | const | CHANGE | 0 |
| var | var | const | var | const | CHANGE | 0 |
| var | var | var | var | const | CHANGE | 0 |
| const | const | const | var | CHANGE | const | 0 |
| var | var | var | const | CHANGE | var | 0 |
| var | var | var | var | var | CHANGE | 0 |
| CHANGE | var | var | var | var | var | const |
| var | CHANGE | var | var | var | var | const |
| var | var | CHANGE | var | var | var | const |
| var | var | var | CHANGE | var | var | const |
| var | var | var | var | var | CHANGE | const |
| CHANGE | var | var | var | const | var | const |
| var | CHANGE | var | var | const | var | const |
| var | var | CHANGE | var | const | var | const |
| var | var | var | CHANGE | const | var | const |
| var | var | var | var | const | CHANGE | const |
| var | var | var | var | const | var | const |

One feature of this is that if the sliding velocity (S) is plotted vs. the entraining velocity (R), the operator can direct the apparatus anywhere desired. The apparatus can moce with changing R changing R and constant S or constant S and changing R. It can also move diagonally across at a constant slope.

The computer is further able to rotate the ball spindle to set the ball angle. The computer does this by controlling a stepper motor powered actuator tied in to a bell crank type mechanism. It receives feedback on the ball angle by way of an electronic inclinometer. This allows the computer to insure that the ball angle is set correctly and relieve the operator from this task.

The computer also reads the load cells. It reads the raw data from the vertical load cells, subtracts the tare and calculates the sum of the individual cells to determine the contact load. Based on the contact geometry and materials, it can calculate the contact stress from the tribological formulas. The load cell, which measures the force in the axial direction of the ball rotation, is read and the tare is subtracted to compute the rear load. The force in the perpendicular direction is similarly computed to determine the side force. The side force is added as a vector to the rear force to determine the resultant horizontal force. The horizontal force is divided by the vertical force to determine the traction force (coefficient of friction). The direction of the side force is used to add polarity to the traction force so that there is a positive and negative traction force depending on the direction of the traction force.

The vertical movement of the disc and its force against the ball is controlled by a stepper motor, which in turn is controlled by the computer. The operator can input the vertical load set-point to the computer and the computer will load the contact accordingly. The computer uses the vertical load cells to provide feedback to the vertical movement of the disc to determine the proper disc position for a given load. The setpoint can be changed at any point during the test with the computer responding accordingly. The operator can also cause the computer to load and unload the contact independently of the setpoint load.

The load cells are also used as feedback to the computer while it is moving either the disc in the vertical direction or the ball in the horizontal direction. If unexpectedly high loads are encountered, movement is stopped and the operator is queried since this may indicate a problem with horizontal air bearings or encountering some rigid object in the path of travel.

Bulk temperatures are measured and controlled using a multi-channel PID controller. The computer has supervisory control over the temperature controller. The computer can read parameters such as temperature, as well as change set-point and control parameters.

Because the computer controls the contact load and kinematics, and can compute the traction force, it is able to calculate the flash temperature of the contact from the tribological formulas if the operator inputs the specimen material properties.

The computer performs a multitude of functions some of which have been described. A list of the more significant ones are listed in the table below:

RUN TIME

This is normally a read only variable that shows the total time data has been collected. Time can be either displayed in seconds or in hours:minutes:seconds.

BAL RPM

The speed of the ball in RPM. This is updated whenever a variable affecting the ball speed is changed, such as R. Changing this value has effects on R, S, % SLIP, and BAL SPD. The BAL RPM is a set point or desired speed. It is up to the motor controller to maintain this speed. The software limits changes in BAL RPM to no more than 1000 RPM at a time except in a run file.

DSK RPM

The speed of the DISC in RPM. This is updated whenever a variable affecting the disc speed changes such as R. Changing this value has affects on R, S, % SLIP, and DISC SPD. The DSK RPM is a set point or desired speed. It is up to the motor controller to maintain this speed. The software limits changes in DSK RPM to no more than 1000 RPM at a time except in a run file.

BAL SPD

The speed of the ball in inches per sec (ips). This is updated whenever a variable affecting the ball speed changes such as R. Changing this value has effects on R, S, % SLIP, and BAL RPM. The BAL SPD is a set point or desired speed. It is up to the motor controller to maintain this speed. The software limits changes in BAL SPD to no more than 10 ips at a time except in a run file. Internally BAL SPD is convened to BAL RPM.

DSK SPD

The speed of the disc in ips. This is updated whenever a variable affecting the disc speed changes such as R. Changing this value has effects on R, S, % SLIP, and DSK RPM. The DSK SPD is a set point or desired speed. It is up to the motor controller to maintain this speed. The software limits changes in DSK SPD no more than 10 ips at a time except in a run file. Internally DSK SPD is converted to DSK RPM.

% SLIP

The ratio of the rolling velocity (R) divided by the sliding velocity (S) times 100. Changing this number changes S, BAL SPD, DSK SPD, BAL RPM and DSK RPM

R

The rolling velocity of the ball and the disc in inches per second. R can be changed by either keeping S constant or keeping % SLIP constant depending on the position of the CONST SLIP/CONST R-S button.

S

The sliding velocity of the ball and the disc in inches per second. S can be changed either keeping R constant or keeping % SLIP constant depending on the position of the CONST SLIP/CONST R-S button.

Z

The angle between the ball and disc velocity vectors in degrees. Changing this number moves the ball to the correct position. This will also affect the calculation of R, S and %SLIP, as well as if the RLOAD is active. It is possible to change Z during a test and under load since the ball will move along the track diameter.

TRACT

This is a read only variable indicting the traction force. This will always be 0.0 when the rig is unloaded as defined by the load/unload button. Traction is recalculated each period.

V LOAD

A read only variable which indicates the vertical load minus the tare in pounds. It is the sum of the vertical load cell, CELL1, CELL2 and CELL3. It is updated each period.

A LOAD

This is the desired vertical load in pounds applied by moving the disc against the ball. The actual load is indicated by V LOAD.

PUMPSPEED

The speed of the peristaltic pump that supplies the lubricant.

PERIOD

The time the load cell related data is updated in seconds. The bottom display is updated at the end of the period. If the test is running and saving, the data is logged to a file. The screen is also updated once per period.

TEMP 1 through TEMP 7

These are independent temperature channels. The channel names may be renamed to correspond to what is being measured. The temperature units are degrees C.

SP1 through SP7

The set-point for the corresponding temperature channel. The names may be changed in the same manner as the temperatures. If the temperature is equal to or above this temperature, the heaters will not turn on. If the temperature is below this temperature, the heaters will turn on if the PWR is not zero and the heater button is on.

PWR1 through PWR7

The maximum percentage of full output that the bottom heater will put out. A value of 100 will provide full power, 50 half power and 0 no power. Power is regulated on a time basis. Half power will have the heater on half the time. The frequency of on/off is 60 times a second. The names may be changed in the same way as the temperatures.

STRESS

The average contact stress based on the contact load, specimen materials and ball diameter. Units are PSI for English units and GPa for metric units.

WATTS

The number of watts of mechanical energy being put into the contact calculated from the load and the traction forces.

FLASHTEMP

Calculates the approximate theoretical flash temperature of the contact.

MaxTrac

A traction limit. If this limit is reached, the machine unloads, turns off the lub pumps, stops the spindles and turns off the spindle power. This may be set to a number such as 3 so that it is never reached.

STRESS

This is the V LOAD converted to stress using the Poison's ratio, modulus of elasticity input for both the ball and the disc along with the ball diameter. Reading is in PSI.

SLOAD

The side load in pounds minus the tare. This is the sum of CELL4 and CELL6. It is updated each period.

H LOAD

The horizontal load in pounds. In the aligned position, this is equal to the SLOAD since the rear load is zeroed out in software. In the non aligned position, this is the resultant of the SLOAD and R LOAD. It is updated each period.

R LOAD

The rearward load in pounds. In the aligned position this is set to zero. It can be read using a very small value of Z such as 0.001. It can also be seen reading load cell CELL5 that is the identical value. It is updated once each period.

CELL1

The reading of load cell 1 in pounds less the tare. Cell 1 is the rear most vertical load cell. The computer will take load cell readings when it is not doing anything else. It will sum all the readings divided by the number of readings each period. Extra tasks during the period such as screen scrolling, or moving slides may affect the load cell readings. The value is updated once each period.

CELL2

The reading load cell 2 in pounds, minus tare. See description of CELL1. Cell2 is the vertical load cell in the front on the side opposite of the door.

CELL3

The reading load cell 3 in pounds, minus tare. See description of CELL1. Cell2 is the vertical load cell in the front on the side same side as the door.

CELL4

The reading load cell 4 in pounds, minus tare. See description of CELL1. Cell4 is one of two load cells that measure side force. This is the one nearest the ball.

CELL5

The reading load cell 5 in pounds, minus tare. See description of CELL1. Cell5 is the rear load cell.

CELL6

The reading of load cell 6 in pounds, minus tare. See description of CELL1. Cell6 is the side force measuring load cell farthest from the ball.

Track Pos

This is where the track slide thinks it is. Changing Track Pos moves the motorized track slide. Track Pos is in inches and is not the same as Track Dia. Track Pos is mechanical position of the slide. Track Dia is a more far reaching variable. Changing Track Dia moves the slide by changing Track Pos. Changing Track Pos has no effect on Track Dia. The Track Pos has no effect on the DSK SPD while Track Dia does. The dynamic track adjust changes Track Pos and not Track Dia. Track Pos is also changed when Z is changed.
Side Pos This is where the side slide thinks it is and changing its value moves the motorized side slide. Assuming that it was correctly zeroed, it indicates were the side slide is. Side Pos is in inches. The dynamic side adjust, changing Z or track diameter in the non aligned position all change Side Pos.
Angle Pos The angle of the ball spindle vertical tilt. This a read only value in degrees and can only be read in the setup screen.
Lub Speed The speed of the stepper motor lubrication pump. The number ranges from a top speed of about 98 to a low of below 0.01.
RS Slope If this is not zero, changes to R and S will be linked. The ratio between the change in R to the Change in S will be by this ratio.
Track Dia The track diameter in inches. This is used to calculate DSK SPD. Changing this value will cause the rig to change track diameter if the slides are energized.

Figure 28:
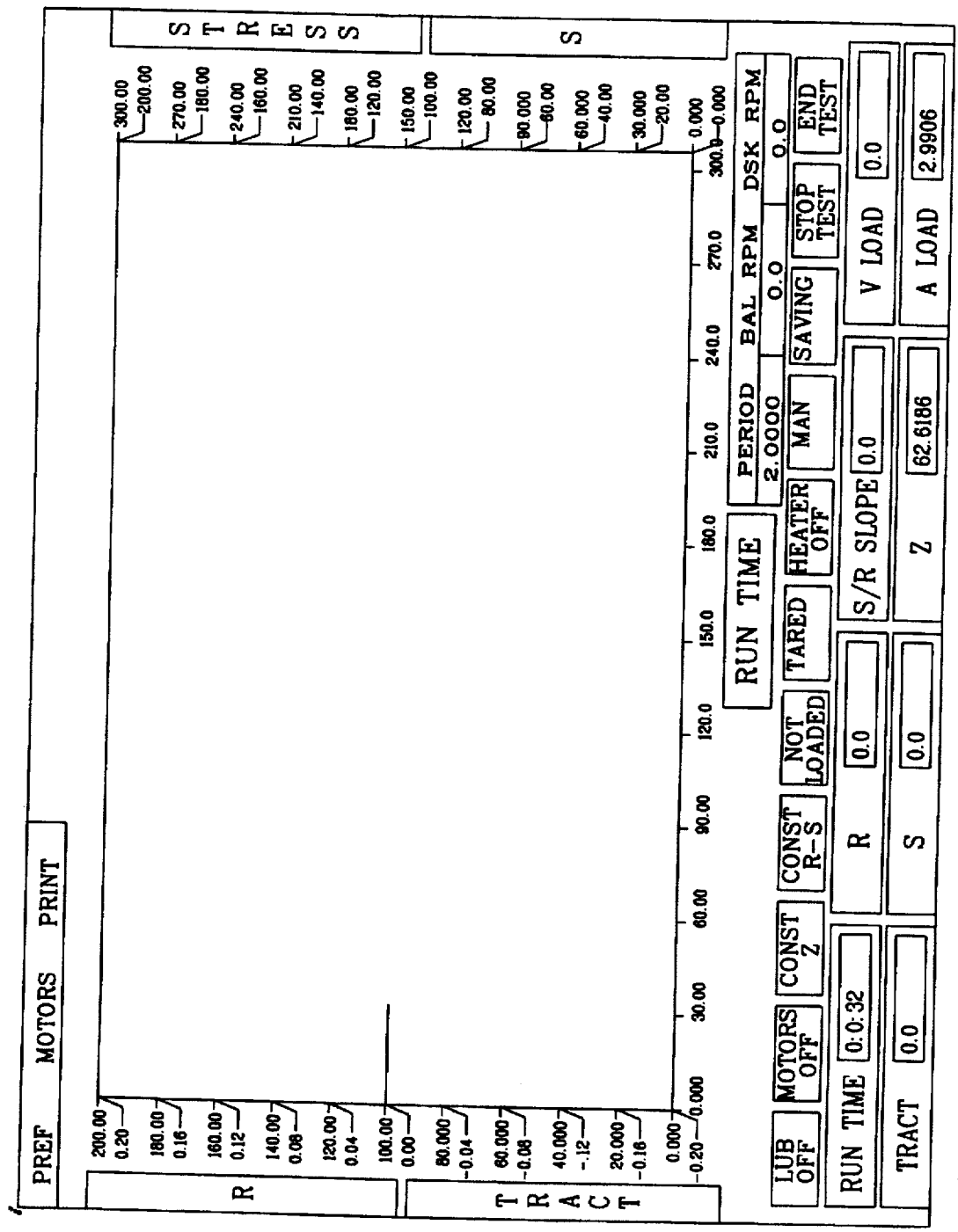
FIG. 28 is an image of the screen when the invention is collecting data.

The computer allows a flexible operator interface. The basic screen is shown in FIG. 28. At the bottom of the screen are eight boxes, which display a variable name and value. The operator may select any variable in any or all boxes. The boxes may be changed at any time as to which variable is displayed and its value. The display configuration may be saved to run a similar test. The value is updated at least once a period. The operator my click the value to change it if it is a value that can be changed such as the speed of the ball. A click with the left mouse button in the units place of the value will increase the value by one. Clicking the ten's place increases the value by ten. Clicking other places has similar effects. Clicking the right button is similar, but causes the value to decrease. These eight boxes are one of the primary ways the operator communicates with the computer with numerical data.

Above the eight boxes is a set of 11 screen buttons that may be changed as to function and state by the operator. The table below explains some of the available buttons and their function.
Mmode determines if a change in R will keep S or % Slip constant and if a change in S will keep R or % Slip constant
constz determines if Z is to remain fixed or constant
loaded load and unloads the contact
program runs a program linked to the main program which can be written in any computer language.
taring tares the load cells
lub turns on and off the lubrication pump
heater turns all heater power on or off
motoroff stops the spindles or restarts them from where they were running before being stopped.
pwroff turns all power to spindles off.
prttest prints a test sheet
prtscr prints a graph of the data displayed;
autoed when activated will run the machine from a file rather than the keyboard and mouse.
save when activated during a test saves the declared data to permanent storage
start starts test, graphical display of data and permanent storage of data.
aborted ends test.

Above the buttons is space for a graphical plot of variables as the test progresses. In the box above the buttons in the center is the dependent variable, in this case Run Time. To the left and right are the dependent variables. Any variable(s) may be used as dependent and independent variables. There can be between one and four dependent variables plotted. The axis scales for the dependent and independent variables can be any values. The independent and dependent variables and the axis scales can be changed at any time prior or during the test. The colors of the resulting traces can likewise be selected and changed at any time. The horizontal axis will scroll to the right and left if the value becomes out of range. Like the numerical boxes at the bottom, the axis scales and the variable identities can be saved to a file for running similar tests. A plot of the independent variables selected vs. the dependent variable is updated in the selected colors once each period while the test is running.

To the right of the dependent axis label above the buttons is a second grouping of the apparatus variables, which can likewise be changed to any which the operator wishes. This set is likewise updated once a period and may be changed by the operator using the keyboard function keys.

At the top left of the screen is a set of pop-up menus to change various configurations and do miscellaneous house keeping functions.

Figure 29:
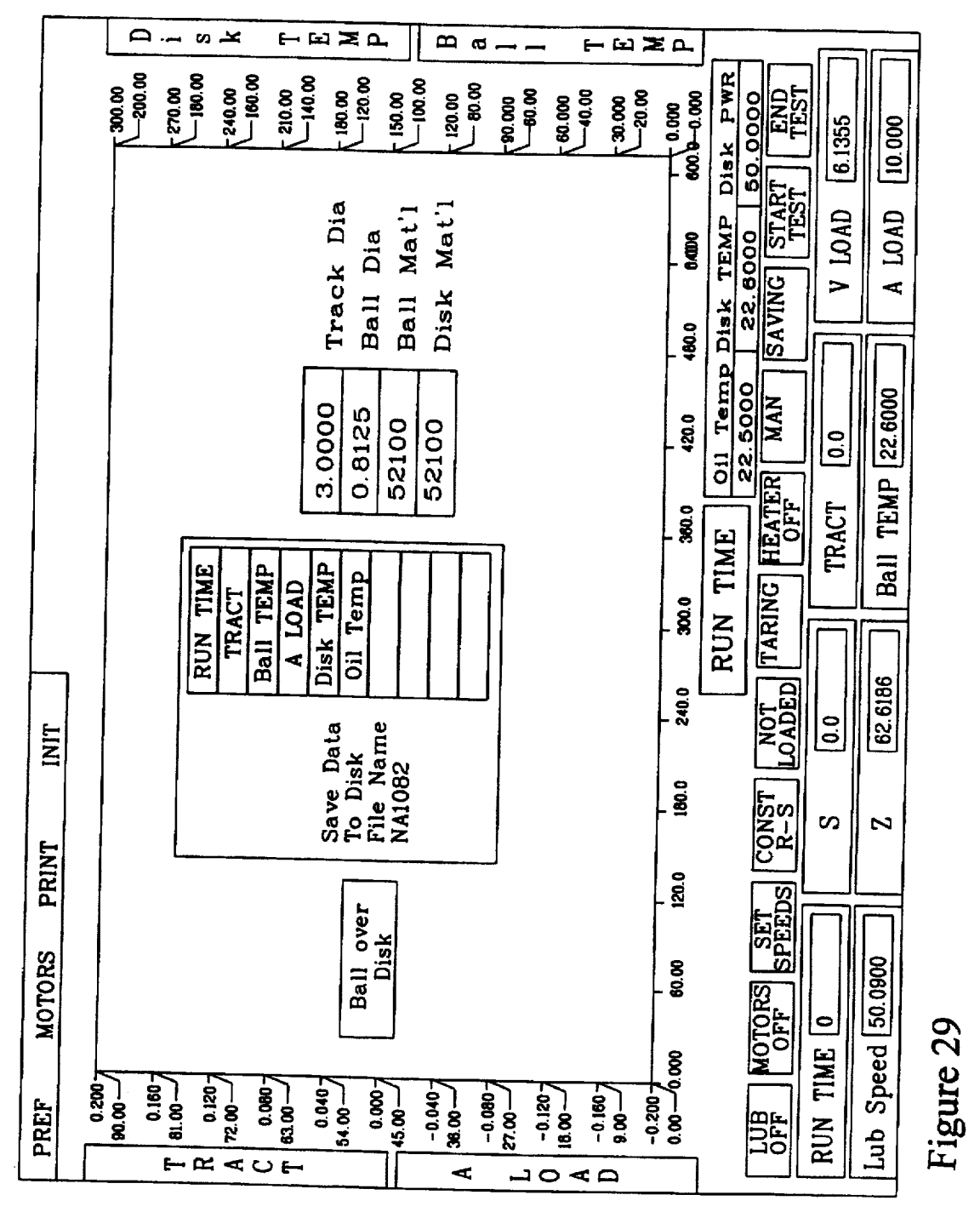

FIG. 29 shows the computer screen before the test is started. In the center of the screen are places where the user may select the name of the data file where data will be saved to a permanent storage device. There is also a set of ten boxes where the operator can indicate which variable to save. The operator may save up to any ten variables in any order. To the right are boxes where the user indicated variables can be displayed as specimen information.

FIG. 30 shows the type of data recorded to the permanent storage device. The first line contains the name of the file, the date and time the test started. The second line lists the lubricant name. The third line shows the ball diameter and specimen number. The next line lists the disc track diameter and specimen number. The fifth line shows the units the measurements are in and the value for Z at the start of the test. The next line of text names the columns of data. These names will depend on which variables the operator selected and in which order. The rest of the file contains the data in columnar form. The data is normally plotted after the test using a commercially available software package for plotting (Sigma Plot by Jandel Scientific or equivalent).

The apparatus is normally operated from the keyboard and mouse in real time while watching the effects to the variables. It is possible to program the apparatus to make the same changes to the variables at predetermined times. This is done by recording the commands on a permanent storage device and then instructing the apparatus to operate from this file. Some of the commands are listed below followed by a brief explanation of their function.

| | |
|---|---|
| SLIP = X | Changes the % SLIP to the value indicated by X. |
| R = X | Changes R to the value indicated by X. |
| BALLSPD = X | Changes BAL SPD to the value indicated by X. |
| DISCSPD = X | Changes DSK SPD to the value indicated by X. |
| BALLRPM = X | Changes BAL RPM to the value indicated by X. |
| DISCRPM = X | Changes DSK RPM to the value indicated by X. |
| Z = X | Changes Z to the value indicated by X. |
| TIME = X | Tell the program to wait until ELASTIME = X before proceeding |
| ALOAD = X | Changes ALOAD to the value indicated by X. |
| STOP | Turns on STOP TEST button. Button must be manually reset. |
| SAVEON | Turns on the SAVE button |
| SAVEOFF | Turns off the SAVE button. |
| MANUAL | Return to manual mode. |
| END | Ends the test, same as ABORT button. |
| LOAD | Turns on load button and loads |
| UNLOAD | Turns off load button and unloads. |
| PERIOD = X | Changes PERIOD to X |
| SP1 = X | Changes temperature controller channel 1 set-point to X |
| SP2 = X | Changes temperature controller channel 2 set-point to X |
| SP3 = X | Changes temperature controller channel 3 set-point to X |
| SP4 = X | Changes temperature controller channel 4 set-point to X |
| PWR1 = X | Changes temperature controller channel 1 percent output to X |
| PWR2 = X | Changes temperature controller channel 2 percent output to X |
| PWR3 = X | Changes temperature controller channel 3 percent output to X |
| MINLOAD | Puts rig in micro unload mode |
| NORLOAD | Puts rig in normal unload mode |
| SETUP = X | Changes screen to that of the .int file named X |
| CONSTR | Turns on the CONST R-S button |
| CSTSLIP | Turns on the CONST SLIP button |
| TRACCLR = X | Changes main trace to color detailed in table 1 |
| LUBON | Turns on lubrication pump and indicates with lub button. |
| LUBOFF | Turns off lubrication pump and indicates with lub button. |
| CONSTZ | Turns on CONST Z button |
| VARZ | Turns button to VAR Z |
| SETTIME = X | Changes ELASTIME to X |
| SHOWBOX = X Y | Changes the display box on bottom of screen to display variable as decoded in Table II |
| TARE | Turns on button and tares |
| PLOT | Updates display independent of period |
| LOGDATA | Logs data independent of period |
| DISCPOS = X | Changes Disc Pos to X |
| SIDEPOS = X | Changes Side Pos to X |
| TRACPOS | Sets Traction Positive button to on |
| S = X | Changes S to X |
| LOOPEND = X | The termination value of the loop |
| LOOPINC = X | The increment LOOPVAR will be increased, may be negative. |
| LOOPVAR = X | Sets which variable will be incremented per table 2 |
| LOOPTIME = X | Sets the period in seconds between loop increments |
| LOOP | Starts looping |
| PWROFF | Turns off the motor contactor |
| PRTSCRN | Prints the current screen plot |
| PRTTEST | Prints a plot of the entire test |
| PRTSHT | Prints test sheet |
| LUBSPED = X | Changes the lubrication speed to X |
| HEATON | Turns on heater relay |
| HEATOFF | Turns off heater relay |
| RSsSLOPE = X | Changes R/S slope to X |
| CONSTZ | Turns on the Constant Z button |
| VARZ | Turns on Varying Z button |
| Z = X | Changes Z to X |

Process for Comprehensive Evaluation of the Structural Elements of a Lubricated Contact One skilled in the art would recognize that the process of the present invention has the capabilities summarized below.

A process to systematically evaluate the performance and durability of individual elements of a lubricated contact system comprising the general structural elements of: (1) a viscous generated film between the surfaces, (2) boundary films attached to the surfaces of the contacting bodies, (3) near-surface region of the contacting bodies, including their topographical features, and (4) a sub-surface region within the two bodies. The systematic evaluation is made possible by utilizing tribologically specific velocity vectors representing an entraining velocity, defined as ½ the vector sum of the surface velocities of the contacting surfaces, and a sliding velocity, defined as the vector difference between the surface velocities. The velocity vectors are varied independently, in magnitude and direction, to de-couple the viscous lubricating film-forming functions of the inlet region, upstream of the contact, from the load bearing functions within the Hertzian contact region. The entraining velocity vector provides precise control of surface separation and load sharing among surface features due to ehd film formation—a mechanistic process controlled by viscous pressure generation of a fluid in a convergent space (inlet region). The sliding velocity vector provides precise control of tangential shear of the bulk lubricant film, surface films and the near-surface material within the Hertzian contact region. The de-coupling of the functions with the inlet region from the functions with the Hertzian region by way of the independent variation of the entraining velocity and sliding velocity, along with conventional lubrication parameters of contact stress, temperature, materials, surface features and surrounding environment, provides an added degree of freedom to a testing process. The added degree of freedom allows the control of normal stress, tangential strain and the location of strain accommodation between the contacting surfaces. The independent control of normal stress (and its distribution among the topographical surface features, tangential strain and its location within the contact allows the performance and durability of a tribological contact system to be evaluated as individual elements of a contact system, along with the associated technologies that comprise that system.

It is recognized that the structural elements of a contact system are dynamic. The existence of the lubricating film between the surfaces is due to the dynamic motion of the surfaces. The topographical features and mechanical properties of the near-surface region change due to operation with less than full-film ehd lubrication, where the surfaces are not completely separated. Boundary lubricating surface films may form and be removed. The dynamic nature of the structural elements creates an inherent difficulty for performance prediction, even with extensive testing. Yet, there are some fundamental properties of these structural elements that can be derived from the contact system. These fundamental properties include the pressure-viscosity coefficient, $\alpha$, and the traction coefficient of the test fluid. These properties allow a first tier predictive performance. A rational testing process, together with these fundamental properties, enables a comprehensive evaluation of the structural elements of a contact system and the performance of the structural element within the context of a contact system that simulates the conditions of field hardware.

The process of the present invention is described by following all or some the following steps:

Step 1

Fluid Film Forming Properties

The generation of an ehd film is a primarily a function of two physical properties of the fluid. The viscosity $\mu_o$ at the operation temperature within the inlet region and the pressure-viscosity coefficient, $\alpha$. Viscosity-temperature characteristics of fluids are readily available and easily determined. Pressure-viscosity characteristics are generally not known but can be determined from the contact itself by the direct measurement of film thickness with optical interferometry.

Figure 31:
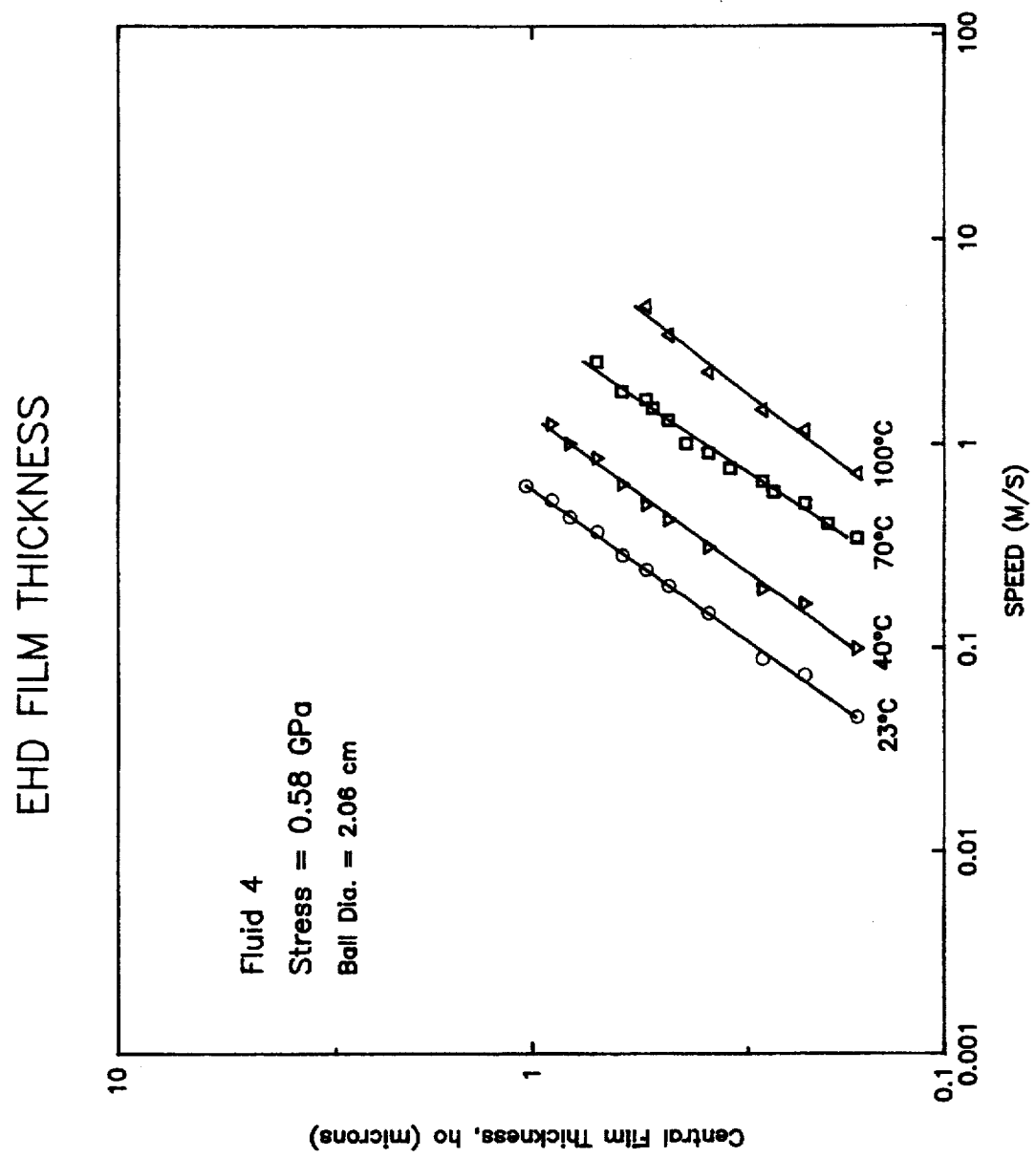
FIG. 31 shows the measured ehd film thickness vs. entraining velocity of a fluid for four temperatures.

To obtain the pressure-viscosity coefficient of the fluid, the ehd film thickness is measured by recording the optical fringe color in the center of the contact as a function of rolling velocity. The optical film thickness data is converted the refractive index of the making corrections for the refractive index of the test fluid, including the effect of pressure on density under the Hertzian contact Film thickness data is generated by determining the entraining velocity (rolling velocity) corresponding to each fringe color. Film thickness tests are conducted over a range of temperatures. Typical data is shown in FIG. 31.

Figure 32:
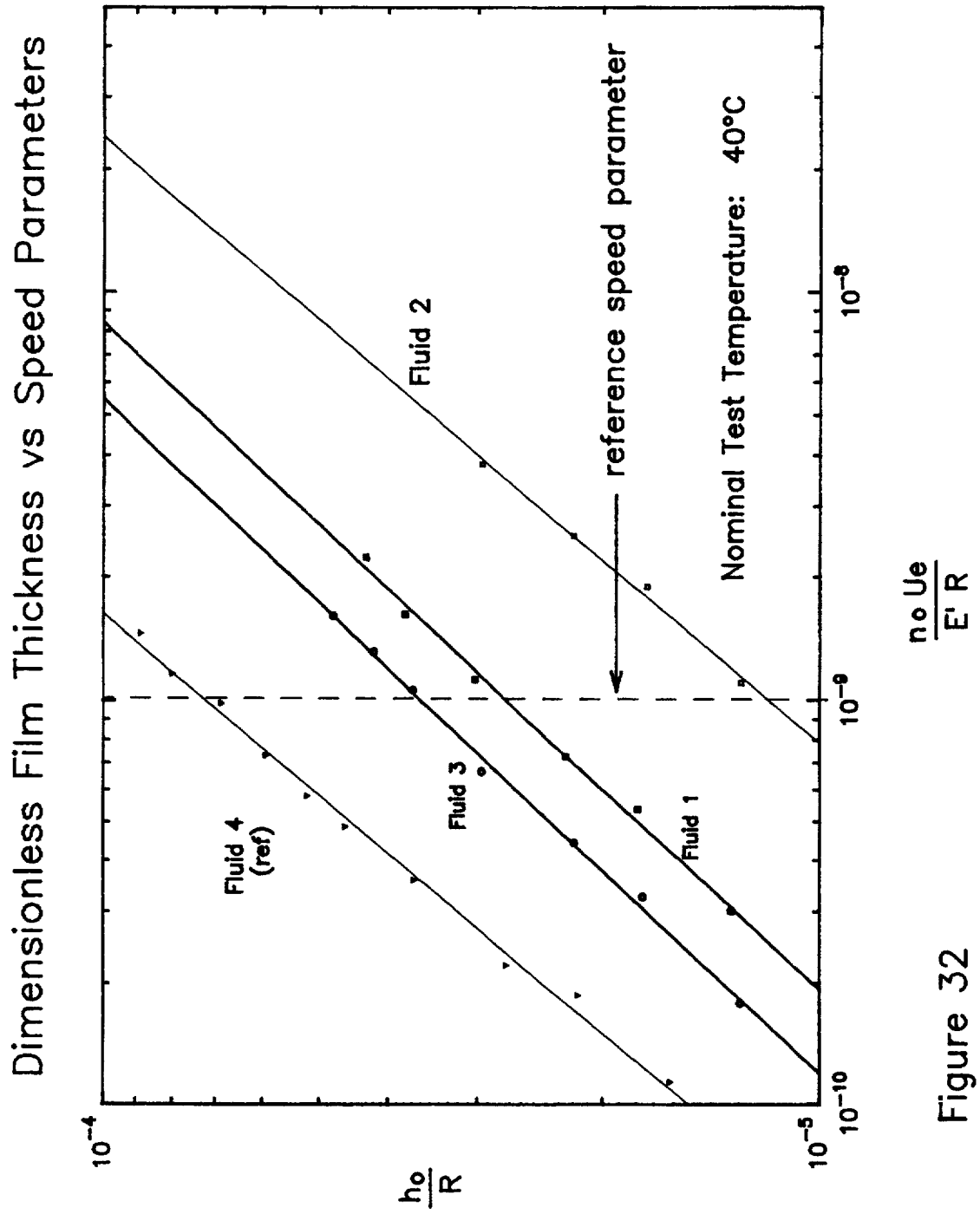
FIG. 32 shows a dimensionless film thickness parameter vs. dimensionless speed parameter for four test fluids. The relative position of the test data reflect the pressure-viscosity coefficient of the each fluid.

To determine the pressure-viscosity coefficient for test fluids, the film thickness data is plotted in dimensionless form using a dimensionless film thickness parameter ($h_o/R_c$) where:

$h_o$=film thickness in the center of the contact, $R_c$=combined radius of curvature and a dimensionless speed parameter which is defined as:

$\mu_o R/E'R_c$ where:

$\mu_o$=viscosity at atmospheric pressure and test temperature,

R=entraining velocity, $R=\frac{1}{2}(U_1+U_2)$,

E'=combined elastic modulus of specimen materials, $R_c$=combined radius of curvature For example, test fluids are plotted in dimensionless form and nominal test temperature of 40° C. in FIG. 32. The only ehd lubricant characteristic missing from the two dimensionless parameters is the pressure-viscosity coefficient ($\alpha$) and load (w). The film thickness measurements can be conducted under the same load. If the $\alpha$-value for each fluid measured was the same, the film thickness data would all fall on a single line. Higher values of ($h_o/R$) for the same ($\mu_o R/E'R_c$) reflect higher pressure-viscosity coefficients.

If a reference fluid of known pressure-viscosity is used, it is possible to calculate the "relative" pressure-viscosity coefficient from the equation below.

$$a = a_{ref\,oil} \left| \frac{ho/R}{(ho/R)_{ref\,oil}} \right|^{1.887}$$

Figure 33:
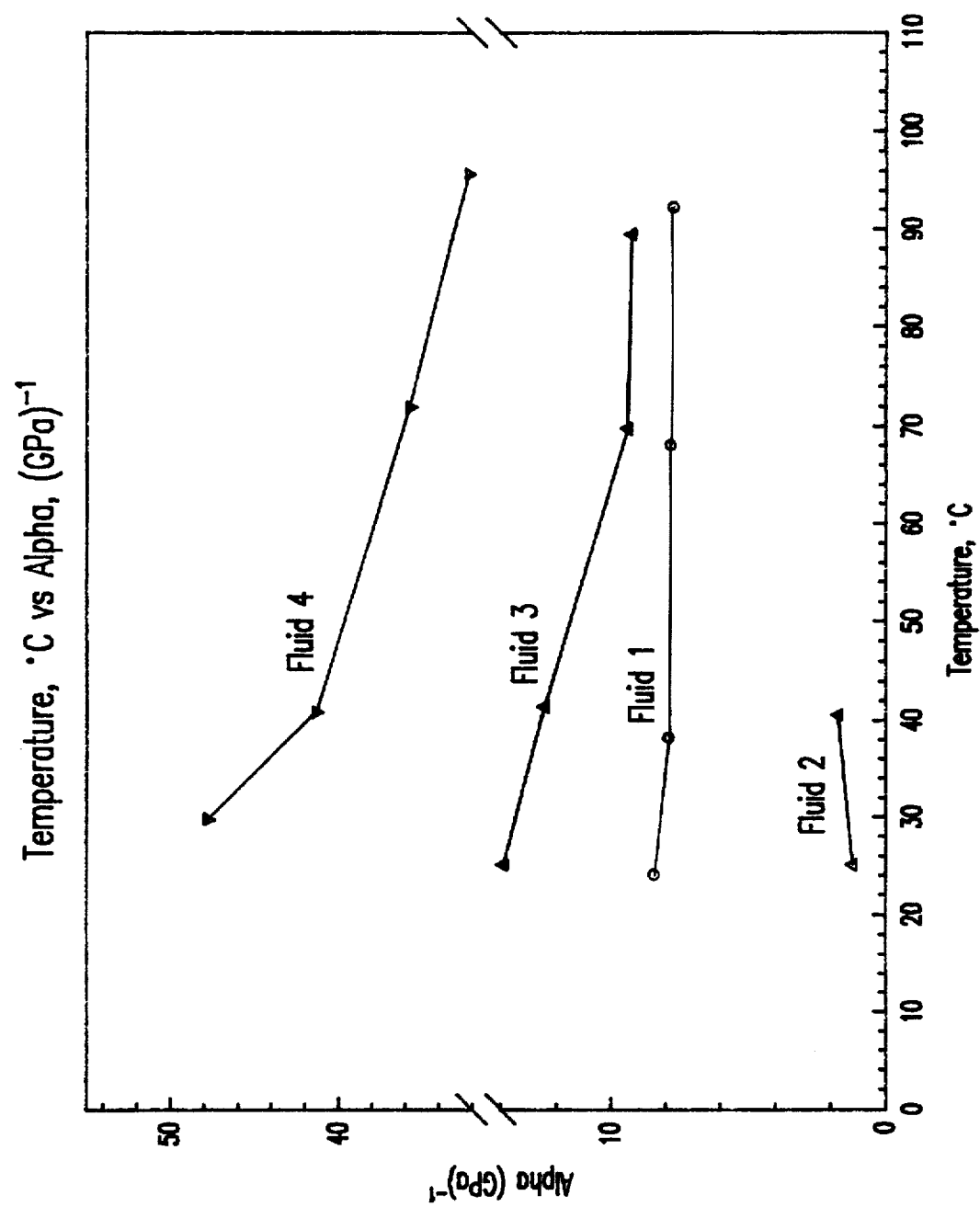
FIG. 33 shows the variation of $\alpha$-value with temperature for four fluids

The above equation assumes that $h_o$ is proportional to $\alpha^{0.53}$ according to ehd theory. The calculated $\alpha$-values for four test fluids are shown in FIG. 33.

The $\alpha$-values, along with viscosity ($\mu_o$) data, are fundamental property data, which can be used to predict ehd film thickness. In connection with the present invention, they are used to select operating conditions for further characterization of the structural elements of a contact system.

Step 1a

Micro-Ehd Film Forming Properties

The viscous film-forming properties ($\alpha$ and $\mu_o$) are fundamental properties that allow calculation of the ehd fluid film separation between surfaces. With non-smooth surfaces, topographical features, along with fluid properties, can invoke a phenomena of micro-ehd film formation associated with the interaction of individual surface features.

Figure 34:
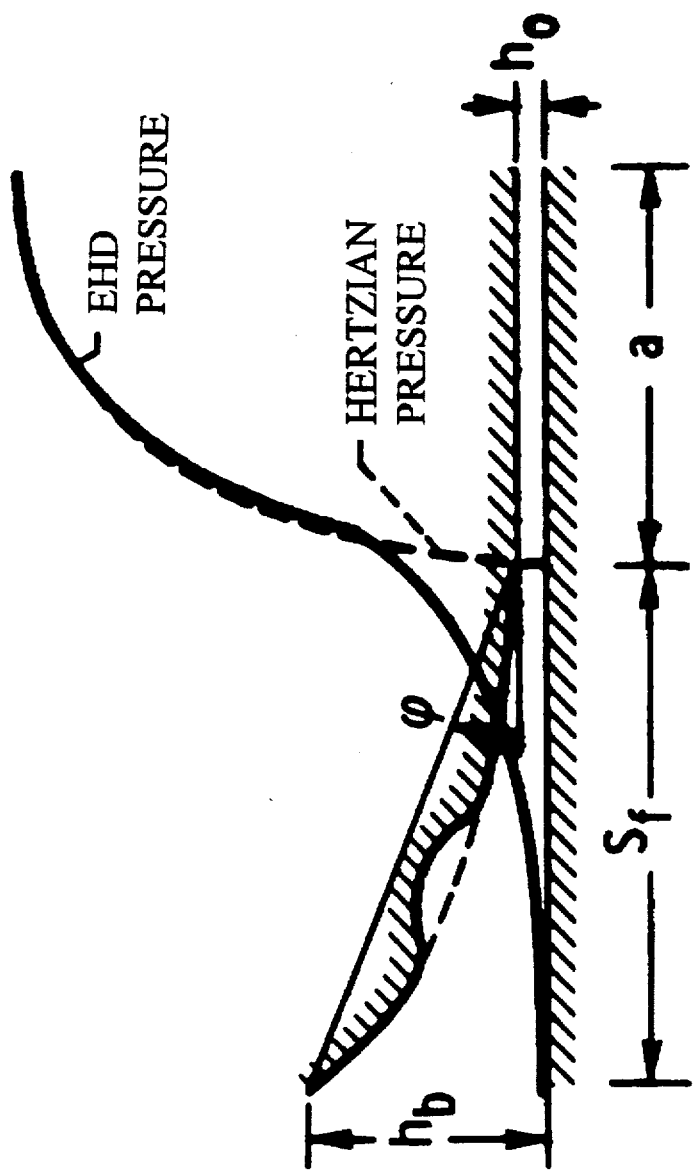
FIG. 34 shows a schematic representation of the characteristic inlet dimensions in relation to a surface feature.

If surface features modify the shape of the inlet region as they pass through the inlet region, they can influence the ehd pressure generation and the local film thickness in and around the surface features. One determines the degree of influence a surface feature has by judging the size of the surface feature, relative to the size of the inlet region, as shown schematically in FIG. 34. The size (height and length) of the surface feature can be judged relative to the size of the inlet region with a characteristic height $h_b$ and characteristic length $S_f$ defined as:

$h_b = 9h_o$ $S_f = 3.52(R_c h_o)^{2/3}/a^{1/3}$ where $h_o$=ehd film thickness in center of Hertzian contact $h_b$=thickness of gap in inlet region where ehd pressure initiates.

$R_c$=combined radius of curvature of contacting specimens $S_f$=distance from upstream edge of Hertzian contact to location where the ehd pressure initiates.

$a=\frac{1}{2}$ the Hertzian contact width in direction of the entraining velocity If the size of the surface feature is small, relative to the characteristic dimensions of the inlet region, the passage of the surface feature through the contact will occur with little perturbation. If the size of the surface feature is on the same order of magnitude as the inlet dimensions, local ehd generated pressures will distort the film thickness in and around the surface feature. If the surface feature passes though the contact region under pure-rolling conditions, the distorted shape of the surface feature is "frozen in." If the surface feature encounters the Hertzian region under combined rolling and sliding, the sliding component causes local ehd pressures to be generated at locations where there is a converging geometry. This action can cause the topographical features to flatten out due to elastic deformation at local areas of micro-ehd action. A secondary film-forming property of the fluid is associated with micro-ehd pressure generation. The secondary film-forming property is associated with its ehd pressure generating power within a high pressure environment of the Hertzian contact region.

The invention, with its ability to independently control surface separation with the entraining velocity and the tangential shear with the sliding velocity, allows a complete characterization of micro-ehd fluid performance. One observes topographical features, either natural or artificially produced, with optical interferometry having the light source synchronized with the passing of selected features through the contact. The micro-ehd deformation associated with surface features is characterized by precise control and variation of surface separation $h_o$ and the accurate measure of the local film thickness in and around the surface feature with interferometry as it passes through the Hertzian region with varying sliding velocity in both magnitude and direction.

The total film-forming properties of a fluid are characterized by its viscosity-temperature behavior, pressure-viscosity coefficient and propensity for micro-ehd film generation.

Step 1b

Traction

Traction or friction reflects the "heartbeat" of a lubricated contact. Traction of a bulk fluid film within the contact is a fundamental property of the fluid, which is measured by the apparatus and inherent in the process of evaluating the structural elements of a contact system.

Figure 7:
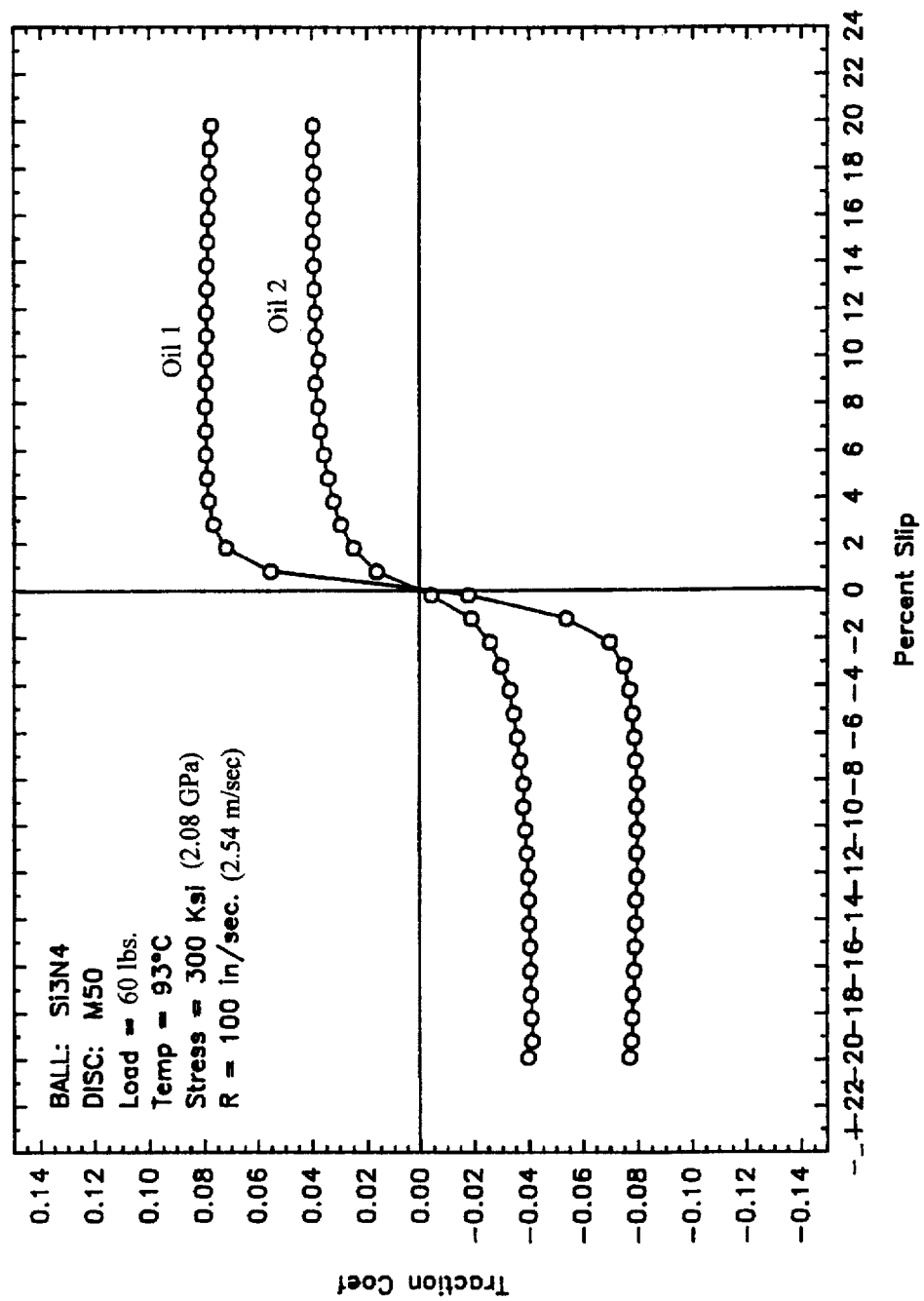
FIG. 7 is a plot of the measured traction coefficient over positive and negative slip conditions for two oils. The invention extracts this data from the contact and uses it as part of a comprehensive evaluation.
Figure 8:
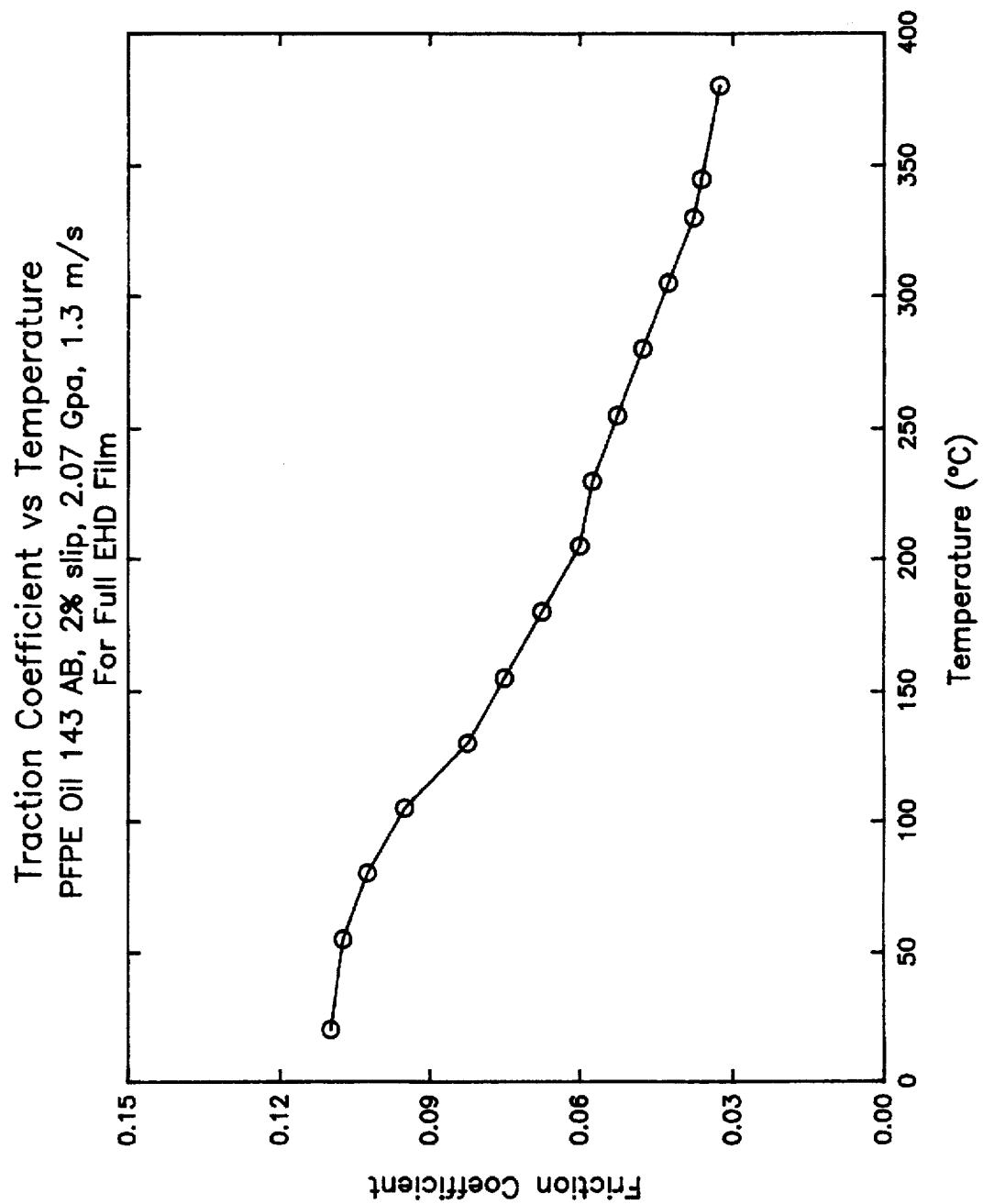
FIG. 8 is a plot of the measured traction coefficient vs. temperature taken under low slip (2%) conditions where the heat generation within the contact is small. The measured traction coefficient is used as an indirect measure of the oil film temperature under high slip conditions. The data is used for prediction of heat generation and mechanical efficiency.

The traction derived from an ehd fluid film is a function of the limiting shear strength of the pseudo-solid fluid in the Hertzian contact region for highly loaded contacts. The limiting shear strength is a function of the molecular structure and is easily recognized by the level traction coefficient, as shown in FIG. 7. The traction coefficient decreases with increasing temperature, as shown in FIG. 8. The decrease in traction is usually a linear function with respect to temperature—a feature which allows the estimation of fluid film temperature within the contact. The traction coefficient increases with contact pressure, up to a limit. The traction properties of a fluid are characterized by operating under full-film lubrication conditions over a range of temperatures, pressures and sliding velocities from incipient sliding to pure sliding. The fundamental traction behavior of a fluid is directly translated to heat generation and the energy efficiency associated with power transmitted across the contact. Full-film traction behavior establishes a reference for further evaluation of the structural elements of a contact.

Figure 35:
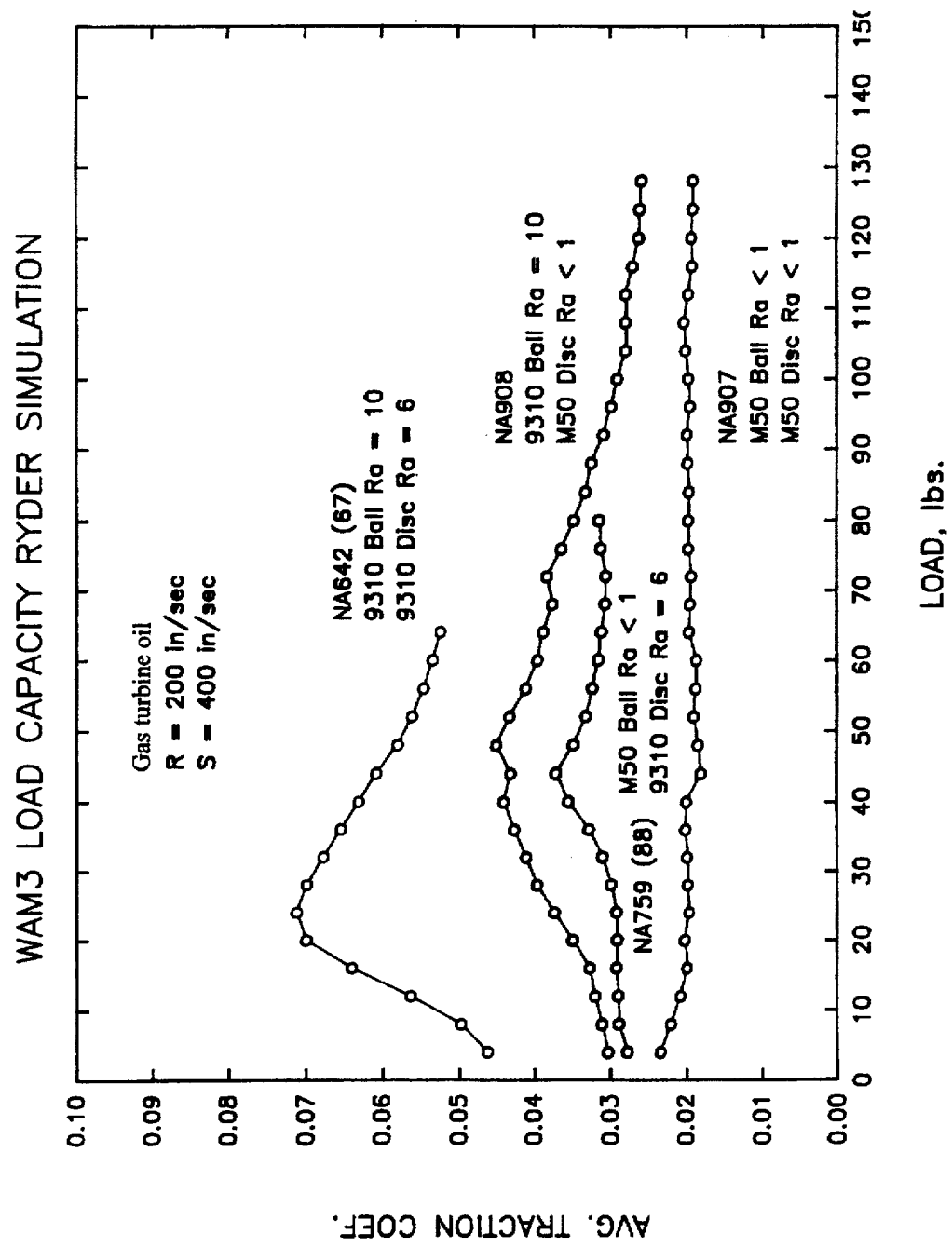
FIG. 35 shows the variation of average traction coefficient vs. load for four surface roughness'.
Figure 36:
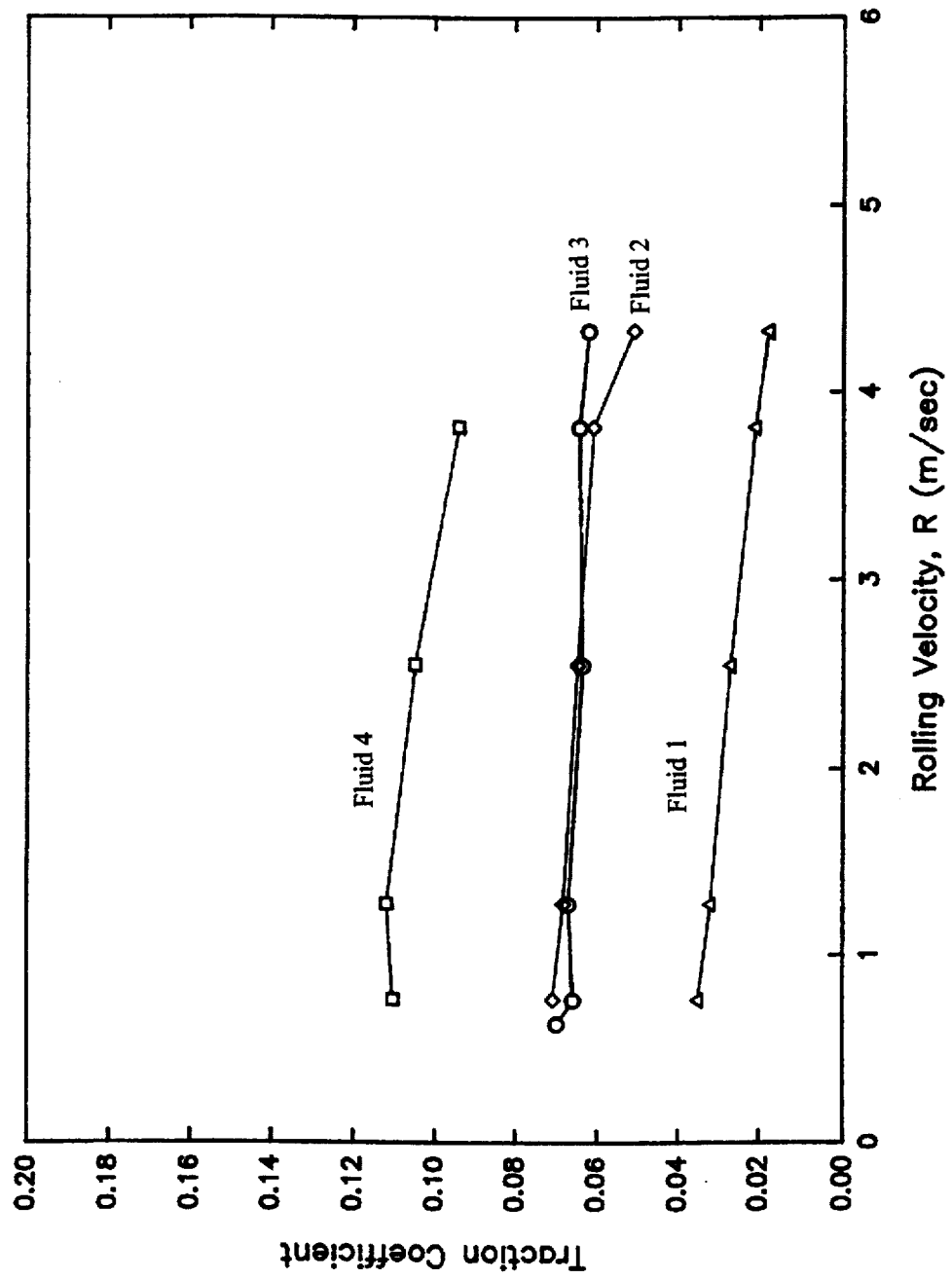
FIG. 36 shows the traction coefficient vs. rolling velocity at constant sliding velocity for four fluids

The bulk traction properties of the fluid are modified by the proximity of interacting surface features. The traction coefficient is sensitive to surface roughness, especially with high sliding velocities. The effect of roughness is shown in FIG. 35 for a contact run with a selected rolling velocity, sliding velocity and varying load. Since the invention allows a gradual reduction in surface separation, the effect of traction on surface separation, as controlled by the entraining velocity R, can be characterized for test fluids. This is shown in FIG. 36.

The invention, and its ability to control the rolling and sliding velocity vectors and other contact conditions, such as contact stress and temperature, allows a point by point evaluation of the operating conditions across the contact footprint of mechanical contacts. Once this action is taken, the traction across a gear tooth contact can be examined for prediction of heat generation and energy efficiency.

The process for a comprehensive evaluation of the structural elements to this point has focused on the characterization of the fluid properties, since they are used to select the operating conditions for further evaluation.

Step 2

Characterization Sub-Surface Performance

The characterization of the sub-surface region is accomplished by controlled normal stress and numbers of operating contact cycles to cause failure initiation in a region below the surface, where the material encounters shear stress cycles. This is accomplished by operating with a sufficient entraining velocity to cause limited stress within the near-surface region so that the controlling failure mode is focused in the sub-surface region. The failure mode of interest is generally sub-surface initiated fatigue, due to repeated cycles of stress in the region below the surface, where the principal shearing stress is maximum. Surface traction influences the magnitude and location of the stress within the sub-surface region. The invention allows the control of the level of tangential stress by way of the traction coefficient and the degree of surface interaction. The degree of surface interaction is controlled to provide tangential stress at the surface without the onset of near-surface failure.

Step 3

Characterization of Surface films

The performance evaluation of the structural elements representing surface films and the near-surface region are the most difficult to accomplish because of their intimate association. This is an almost impossible task without the independent and precise control of surface separation and tangential shear to provide a controlled degree of load sharing and interaction between the topographical features. Boundary lubricating surface films are invoked by thermal, chemical and physical interactions (sometimes called tribochemical interaction). Tribochemical interactions are strongly associated with topographical features. The precise control of this interaction is essential for surface film formation and its performance evaluation.

Figure 37:
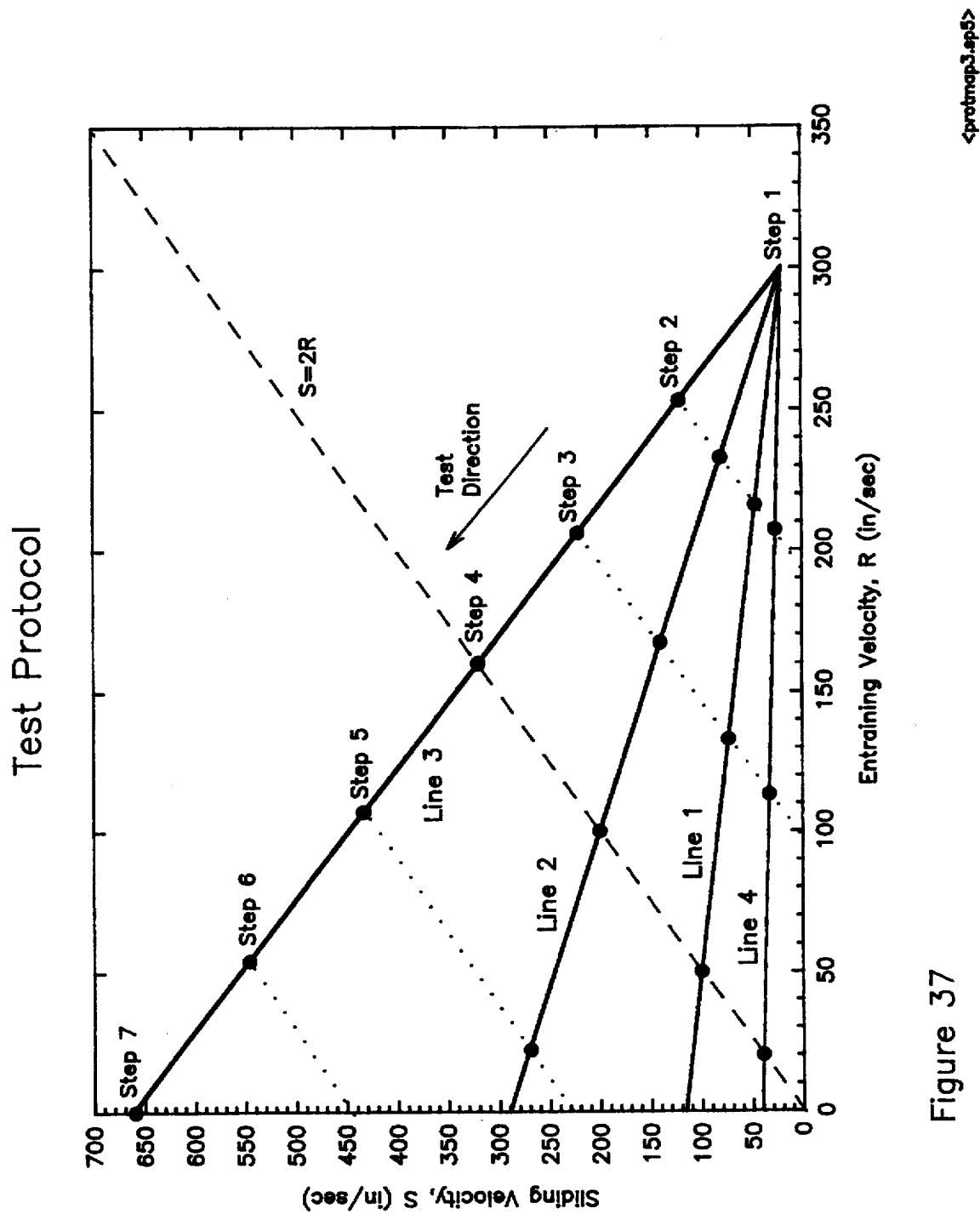
FIG. 37 shows testing pathways in terms of entraining velocity and sliding velocity.

The apparatus of the invention provides real-time observation of the surface with sufficient magnification and a stroboscopic light source to monitor surface features and the formation of surface films. The formation and durability of surface films are accomplished by operating along testing pathways, which control the degree of intimate contact between the surfaces. The degree of contact is in terms of the average separation between the surfaces, which is controlled by the entraining velocity, and the tangential shear, which is controlled by the sliding velocity. Typical testing pathways are shown in FIG. 37. Surface film characterization can be performed along testing lines (or any arbitrary pathway), where the velocity vectors for the contact are varied along with thermal, stress and other tribological parameters. The contact thermal management is controlled in the testing process by externally supplied heat or cooling, as well as, frictional heat generation (flash temperature). The testing protocol can be stopped at selected steps for detailed surface analysis of boundary lubricating films. The durability of surface films is judged by the wear or removal of surface features.

The process of the present invention invokes boundary films and allows the calculation of the contact temperature $T_c$. The contact temperature is the sum of the bulk temperature $T_b$, which is measured for each contacting body and the instantaneous flash temperature $T_f$, which is calculated in real time from the measured traction coefficient, contact load, sliding velocity and material thermal properties. The contact temperature $T_c$ is used to estimate the reactivity of the oil for boundary film formation. If the tests are conducted under conditions that simulate a selected contact system representing field hardware the reaction temperature can be directly connected with field hardware performance.

The process of the present invention allows the determination of in-situ endothermic or exothermic reactions. The entraining velocity can be used to diminish surface separation in a continuous manner to cause the formation of surface films. The entraining and sliding velocity vectors (or other suitable parameters) are varied according to hardware conditions, if desired, and the specimen temperatures are continuously measured along with the traction coefficient and the real-time calculation of flash temperature. The test data is displayed in terms of frictional heat input vs. the measured specimen temperatures, which is normally a linear function. With sufficient tribo-chemical reaction and temperature measurement sensitivity, a departure from a linear relationship can be measured (as shown in FIG. 20). The departure from a linear relation between the power input to the contact and the measured temperature is attributed to endothermic or exothermic reactions of boundary film formation. The point of departure or transition from linear behavior provides the operating conditions and temperatures which activate the "chemistry" of the lubricant. The activation temperature and contact system operating conditions are particularly useful for oil formulation to assess the activity of oil chemistry for the tribo-contact. It is also useful for component design and its field operation to determine operating conditions, which invoke the oil "chemistry."

Step 4

Characterization of Near-Surface Region

The performance of the structural elements representing the lubricating film and surface films are usually judged by their ability to preserve the structural integrity of the near-surface region. The criteria for structural integrity limits of the near-surface region is a user determination based on the function requirements of the component. The user has many descriptive terms which characterize the structural integrity of the near-surface region. These terms include: polishing wear, abrasive wear, ridging, rippling, dull burnishing, scuffing, micro-scuffing, pitting, micro-pitting, frosting and spalling. There are mechanistic processes such as adhesion, fatigue, plastic flow and chemical reaction that occur within the near-surface region that produce the visual features described by the user. The failure processes within the near-surface region are complex because more than one failure mechanism is usually controlling the progression of failure events. The controlling mechanisms that are invoked depend on the normal stress and tangential strain (and their local distribution) within the near-surface region.

Figure 38:
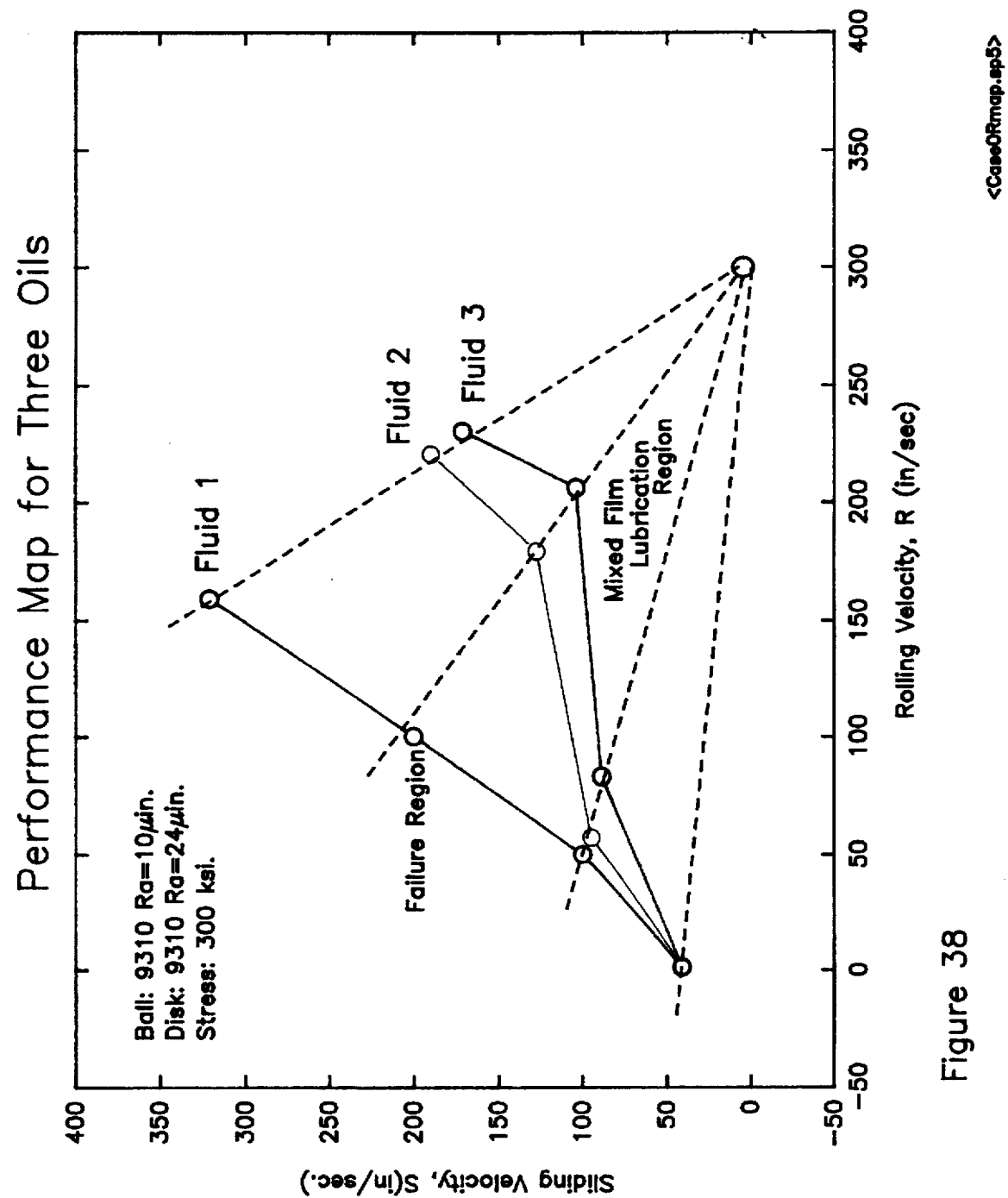
FIG. 38 shows the scuffing failure boundary for three fluids evaluated along four testing pathways.
Figure 39:
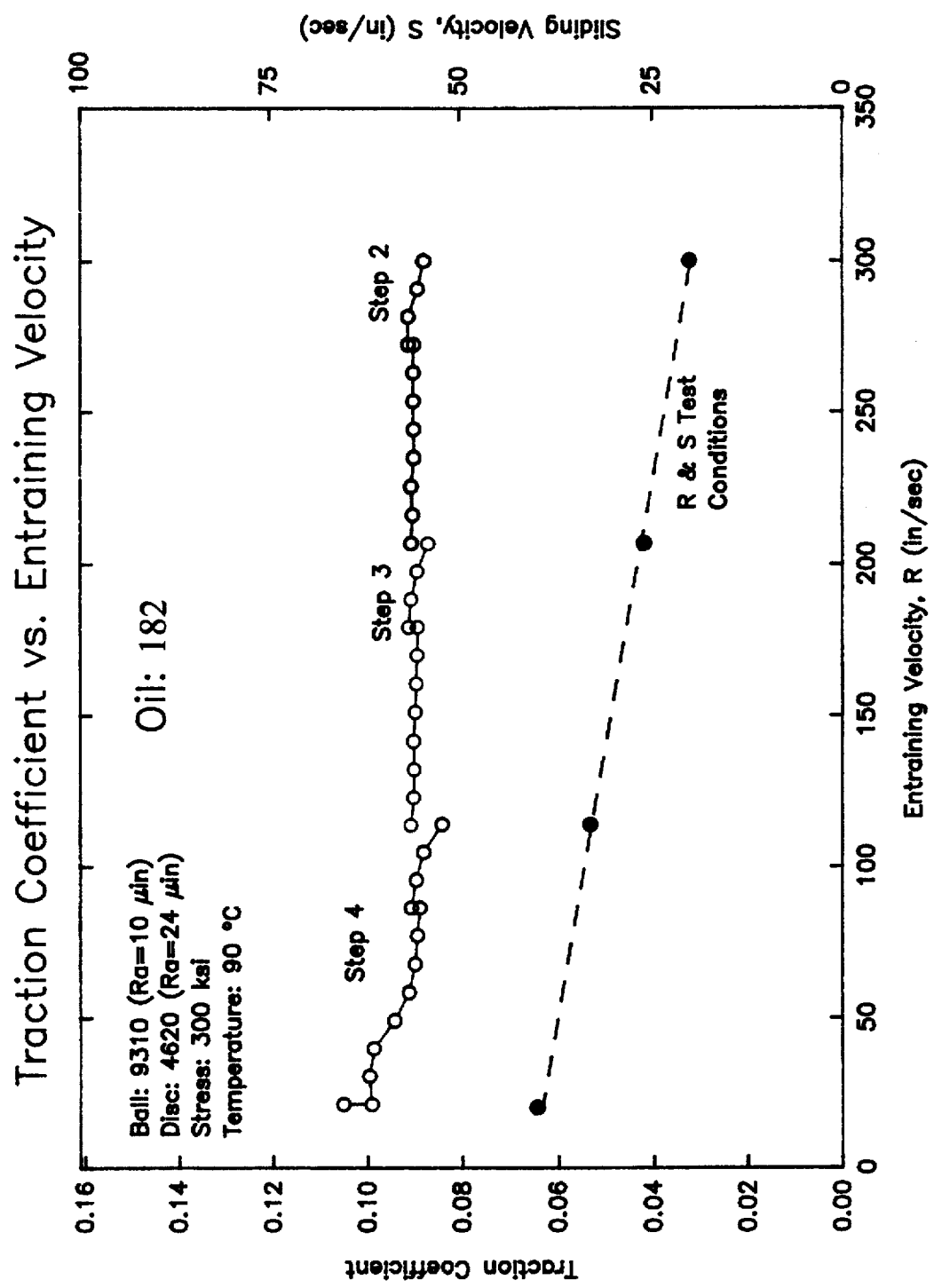
FIG. 39 shows the traction coefficient as a function of reduced entraining velocity for a test oil.

The present invention allows control of the normal stress and tangential strain within the near-surface region. One accomplishes this by the independent control of the entraining velocity and sliding velocity, along with other contact parameters. Testing pathways can be conducted, which invoke specific surface deterioration features in a sequence of events, which may ultimately conclude with catastrophic scuffing. Examples of testing pathways, which illustrate a scuffing event, are shown in FIG. 38. Multiple testing pathways can identify a scuffing boundary, which maps the scuffing performance of a selected oil and the near-surface region. The present invention provides traction information during the course of a testing pathway as shown in FIG. 39. The traction that is measured reflects the bulk fluid traction (evaluated separately, as discussed above), along with the components of traction associated with surface film friction and topographical features (which can be measured separately, as discussed above).

Figure 40:
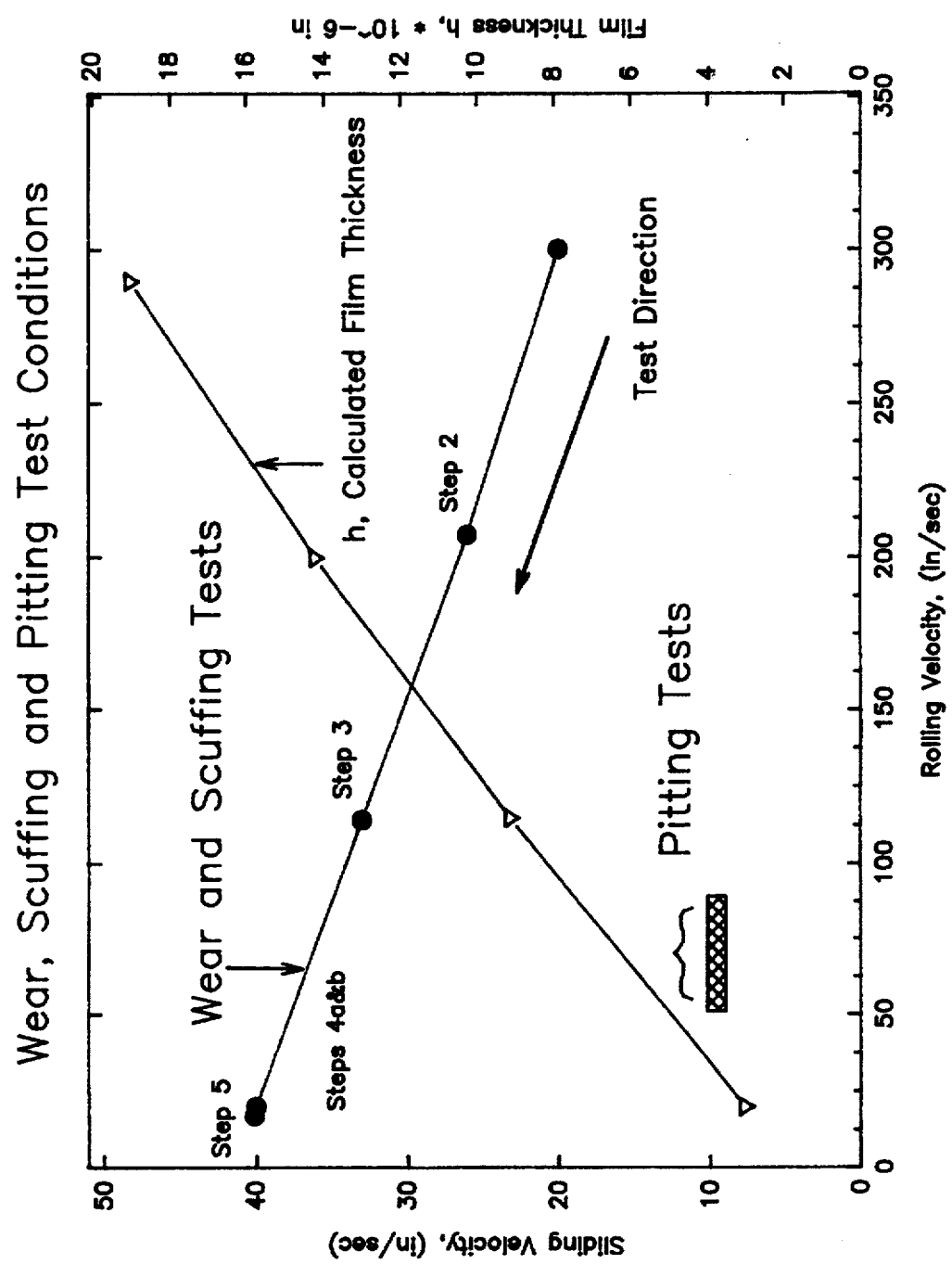
FIG. 40 shows the testing pathways representing a simulated operational excursion followed by extended operation at normal conditions.

The present invention, with its ability to precisely control surface separation and tangential shear, enables a continuous linkage between multiple failure modes. For example, high sliding velocities favor wear, rippling and scuffing fail phenomena. Low sliding tend to allow velocities tend to allow fatigue modes of failure such The independent control of the entraining velocity and sliding velocity, along with other tribological parameters, allow the selection of failure pathways that provides a comprehensive evaluation of the structural elements of a contact system. In addition, the contact system can be driven through lubrication and failure modes that are known to be operative in field hardware. An example is illustrated in FIG. 40, where the simulation of excursions in field operation may lead with wear and possibly scuffing, while most of its normal operation is in a region that will ultimately lead to pitting. The excursions into a region that represents the onset of scuffing accumulates near-surface damage that accelerates the micro-pitting failure mode. The micro-pitting damage at local sites of previous micro-scuffing is illustrated in FIG. 41.

Since the present invention allows real-time observation of surface features, the pathway of the testing process can be immediately changed following the initiation of damage caused by a selected mode of failure. An example is micro-pitting, which is confined to the near-surface region, which can be made to propagate with sufficient normal and tangential stress. If micro-pitting fatigue cracks are made to propagate through the quiescent zone, the principal shearing stresses below the contact may rapidly propagate the fatigue crack into a more serious spalling failure mode.

Performance Map

One skilled in the art would recognize that the process and apparatus of the present invention has the capabilities to map performance of a contact system. The contact system may represent the structural elements of a generic contact system or a simulated contact system comprising the structural elements and operating conditions of specific hardware.

The performance map produces an outline of specific regions where lubrication and failure mechanisms are operative. The process of developing a performance map comprises a series of tests along selected testing pathways. These pathways may be along generic protocols or they may be represented by actual hardware lubriction and failure operating conditions. A performance map is plotted with tribological parameters that control the lubrication of failure mechanisms. The entraining velocity and sliding velocity are preferred candidates for the primary axis of a performance map. Other performance map parameters representing thermal, stress and other tribological variables are added as the mapping exercise is completed.

The performance map is used to identify performance boundaries. The location of the boundaries representing the failure criteria of component hardware, along with the operating conditions of the hardware, is used to quantify performance margin.

Description of Hardware Simulation Process

Figure 42:
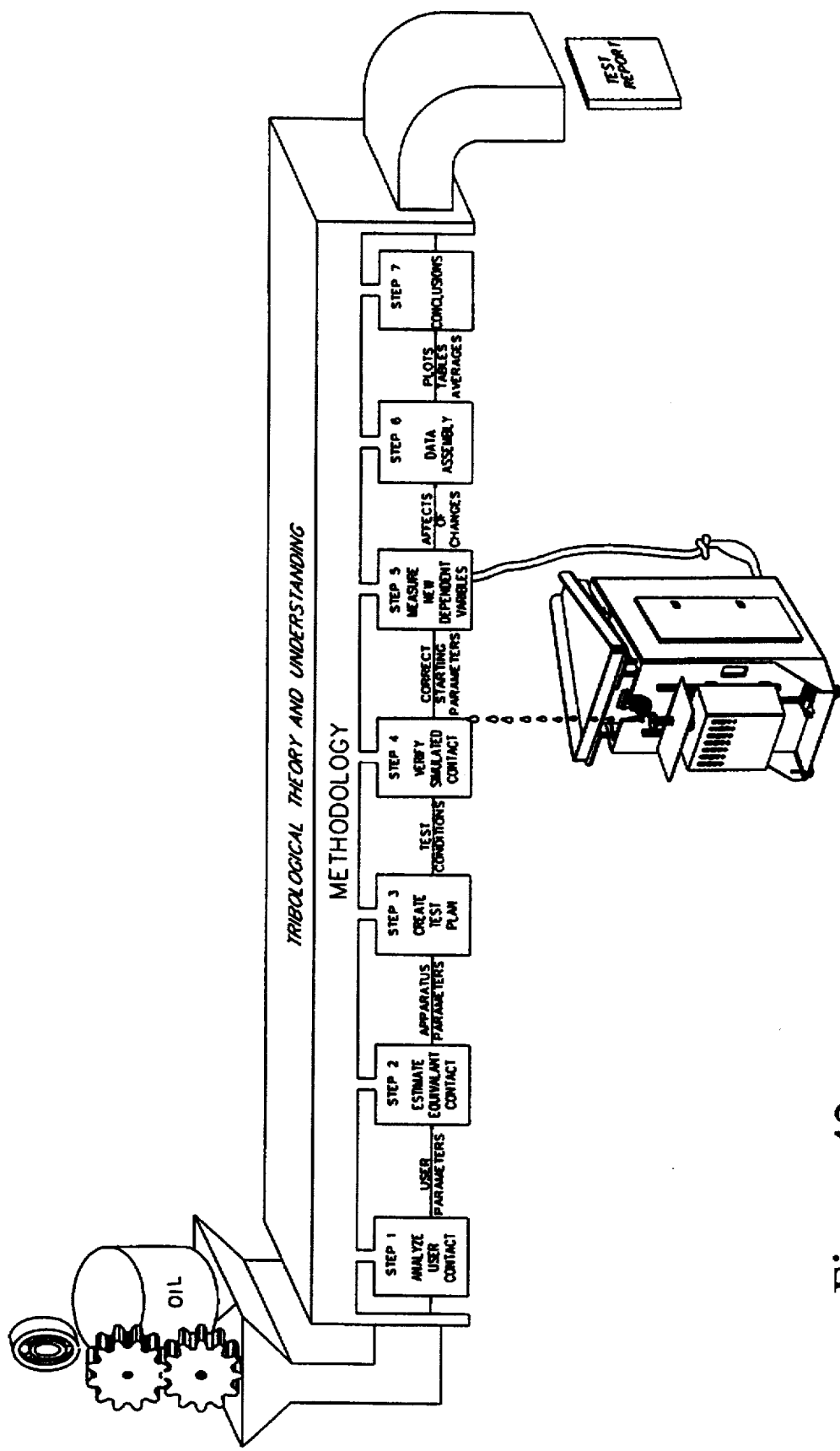
FIG. 42 is a flow chart of a process to use the apparatus to simulate tribological contacts.

The apparatus is capable of operating a tribological contact under infinite combinations of values for kinematic, loading, specimen material, environmental and lubricant. Not only are the number of possible combination of parameters infinite, but they can also be changed in an infinite number of ways over time. The apparatus is also capable of measuring a large number of variables, some of which are more significant than others. One useful function of the apparatus is the simulation of actual tribological contacts encountered in machine components. The simulation provides insight into the contact and allows affects of changes to be tested without having to impact actual hardware. The simulation process is flowcharted in FIG. 42.

The process to simulate tribological machine components starts by examining the contact of the actual hardware. The lubricant, hardware and operating conditions are studied. This is illustrated on the very left side of FIG. 42. Before the process is explained, it should be noted that the process is iterative. At any step, the user can loop back through previous steps to correct problems which were found at a particular step. Not only can the process loop back through previous steps, but the results of the simulation can influence the design, use and configuration of the hardware being tested. This changed hardware might then be simulated through the entire process again.

The process is based on the concept similar to finite element modeling. The process assumes that every machine component can be meshed into a series of small areas. Each area is considered to have a single set of lubrication parameters in terms of kinematic, environmental and lubricant conditions, as well as specimen material, for a given period of time. The conditions may remain constant over time or change. Quite often the conditions are cyclical over time. A gear tooth, for example, comes in and out of contact as the gear revolves. Quite often there is a weak area of operation, where the component is likely to fail. On a ball beating, this might be wear on the cage pockets. Failure on a gear is often at the root of the teeth. Under a specific set of operating conditions, the gear tooth loading is cyclical, but the conditions at a small area point on the gear can be singularly defined when that area of the tooth is engaged. The idea is to simulate kinematic and loading conditions using the same contact materials and lubricants under the same environmental conditions continuously rather than intermittently. Simulating the conditions continuously rather than intermittently allow the study of that particular area of interest rather than the entire component or machine. The continuous operation of the contact under a single set of contact parameters compared to intermittently allows the same amount of contact time in a shorter elapsed time.

The first step of the process is to understand the contact simulation and the goals of the simulation. In the case of a gear, the step would begin with an analysis of the gear pair and a determination of what part of the gear to study. The kinematic conditions are determined for the component under a particular operating point. The analysis includes determination of contact materials and finishes, as well as, the environmental conditions. The contact stress or ranges of stress are determined for the specific lubricant. If the device being simulated exists and is experiencing failures, these failures are studied to determine the type and features of the failure.

The second step is to take the kinematic, loading, specimen material, environmental and lubricant conditions of the simulated machine component and translate these into an equivalent contact on the apparatus. The idea is to have an equivalent, as oppose to identical, tribological contact. Using tribological theory, tradeoffs can be made to provide different macroscopic conditions, while still providing an equivalent tribological contact. This allows a gear, for example, to be simulated using a ball and disc. No substitutions or translations are done for the lubricant or the contact materials. The simulation, however, often attempts to replicate the same environmental conditions at the contact using different conditions. The goal of the simulation is to obtain the same total temperature of the contact, as well as, any special conditions such as low humidity or low vacuum. The total temperature in the simulation may be a different combination of flash and bulk temperature compared the component being simulated. Another goal is to achieve the same contact roughness to lubricant film thickness ratio (lambda ratio). The surface roughness of the specimens and their kinematics may be a different combination from the components being simulated. The contact stress may be similar, yet the contact loads very different due to the differences in the contact geometry between the contact being simulated and the specimens used. The reason for these changes is often limits on the apparatus or specimens. Sometimes the translation is entirely one-to-one for the environment, contact materials, contact stress and kinematics.

Step number 3 is to develop a test plan for the simulation. The component being simulated is already understood and the equivalent contact has been determined. This step seeks to look at which of the kinematic, loading, specimen material, environmental, lubricant and elapsed time parameters are to be changed. The plan also determines how the changes will be made in relation to the other parameters and over what range of values the changes will be made. It also determines which variables are to be monitored and saved. Many of the decisions made in this step are made from studying the operating ranges of the hardware simulated and the goal of the simulation.

Step 4 verifies that the previous steps were done correctly. If the user is totally confident that the apparatus parameters are correct, this step can be skipped. Since most real world simulations are usually based on assumptions concerning the operating conditions of the actual hardware, this step is almost always necessary. The step involves operation of the apparatus under the conditions defined in Step 2. The contact is examined for signs that the contact conditions are similar to the contact being simulated. Indicators include chemical or physical changes to the lubricant and specimens. The step is looking for similarities in wear, formation of chemical films or the oil forming smoke. If similar results are not found, conditions may be changed dynamically in an attempt to find the correct conditions. If correct conditions are not found it may be necessary to go back to previous steps. It should be noted that the order of Step 3 and 4 can be reversed and the order may depend on individual preference and the type of simulation being done.

Once the correct starting point has been verified, the power of the apparatus can be utilized in Step 5. Parameters are changed and monitored, as predetermined in Step 3. It is possible at this step to measure parameters that may not be measurable in the hardware being simulated. Examples of this would be traction coefficient and lubricant film thickness. It is also possible to study the effects of changes to single or multiple parameters and the effects of the changes on the contact. Different lubricants can be tested under identical conditions, for example, to study the effect of wear. This might be done to determine if one lubricant would be better than another for a particular application. Different materials and finishes can also be examined. The possibilities are unlimited. The result of this step is the test data. The data includes the numerical data saved by the apparatus, as well as, the specimens and observations made during the test. The specimen observation can include progressive wear measurements made either during the test or at defined points during the testing. Also included can be data relating to smoke, noise, or other detectable phenomena.

The goal of Step 6 is to organize the data from Step 5. Data in Step 5 is often taken in real time. This often does not allow sufficient time to allow complete understanding of what is occurring in the contact and possible relationships between the variables. This step allows plots to be made of data including summaries of multiple tests. An example of this would be traction of various oils plotted for a defined set of conditions. This step also allows the combining of data, which may not be directly connected together. A plot of contact noise can be combined with a plot of traction both versus elapsed test time.

Step 7 compares the data produced in Steps 5 and 6 to the actual component being simulated. Based on the data and the test data gathered in step one, correlations and conclusion are made.

Other features, advantages, and specific embodiments of this invention will become readily apparent to those exercising ordinary skill in the art after reading the foregoing disclosures. These specific embodiments are within the scope of the claimed subject matter unless otherwise expressly indicated to the contrary.

Moreover, while specific embodiments of this invention have been described in considerable detail, variations and modifications of these embodiments can be effected without departing from the spirit and scope of this invention as disclosed and claimed.

What is claimed is:

1. A lubricated contact system test apparatus for systemic evaluation of tribological performance and durability of individual materials as tribological elements of a lubricated contact system comprising a plurality of contacting bodies meeting together at a uniform point of contact upon their lubricated contacting surfaces, said tribological elements comprising:

1) any film between said contacting surfaces;
2) any boundary film adhered to a contacting surface of a contacting body;
3) a near-surface region of each contacting body; and,
4) a sub-surface region within each contacting body, said lubricated contact system test apparatus comprising:
   a. a first contact assembly comprising:
      i. a first contacting body member having a first contacting surface, said first contacting body member being comprised of test material and symmetric about at least one central axis;
      ii. means to support said first contacting body member through said at least one symmetric central axis defining a support axis; and,
      iii. means for rotation of said first contacting body member about said support axis, defining an axis of rotation for said first contacting body, which rotation may be varied in both rotational speed and direction;
   b. a second contact assembly operatively engaging said first contact assembly, said second contact assembly comprising:
      i. a second contacting body member having a second contacting surface engaging said first contact surface in a contact of uniform area independent of the relative motion of said first and second contacting bodies, said second contacting body member being comprised of test material and symmetric about at least one central axis;
      ii. means to support said second contacting body member through said at least one symmetric central axis defining a support axis; and,
      iii. means for rotation of said second contacting body member about said support axis, defining an axis of rotation for said second contacting body, which rotation may be varied in both rotational speed and direction;
   c. lubrication means to provide a test lubricating material comprising at least one lubricating substance in the form of a solid, liquid or gas to the contact point of said first contact surface and said second contact surface;
   d. orientation means to locate said uniform point of contact of said first contact surface and said second contact surface with respect to the axis of rotation of said first contacting body member and the axis of rotation of said second contacting body member;
   e. means to measure the rotational speed and direction of said first contacting body to obtain a first velocity vector for said first contacting body in relation to the contact;
   f. means to measure the rotational speed and direction of said second contacting body to obtain a second velocity vector for said second contacting body in relation to the contact;

wherein an entraining velocity of the lubricated contact system, representative of hydrodynamic and elastohydrodynamic (EHD) lubrication of the contact, is one-half of the vector sum of said first velocity vector and said second velocity vector, and a sliding velocity of the lubricated contact system, representative of lubrication mechanisms within the contact, is the vector difference of said first velocity vector and said second velocity vector; and, wherein said entraining velocity is controlled independently of said sliding velocity through selective placement of said uniform point of contact of said first and second contact surfaces, by selective location of said uniform point of contact with respect to the axis of rotation of said first contacting body member and the axis of rotation of said second contacting body member and rotational speed of said first and second contact body members, and, said sliding velocity is controlled independently of said entraining velocity through the selective placement of said uniform point of contact of said first and second contact surfaces, by selective location of said uniform point of contact with respect to the axis of rotation of said first contacting body member and the axis of rotation of said second contacting body member and rotational speed of said first and second contact body members.

2. The apparatus of claim 1, further comprising loading means to apply a selective load to the contact through said first and second contacting body members.

3. The apparatus of claim 1, further comprising means to measure the temperature of the lubricated contact test system at a point chosen from the group consisting of:
   points on or within said first contacting body;
   points on or within said second contacting body;
   points on said first contacting surface;
   points on said second contacting surface;
   points within or proximate to said contact; and,
   points within said lubricating material.

4. The apparatus of claim 1, further comprising means to control the temperature of the lubricated contact test system at a point chosen from the group consisting of:
   points on or within said first contacting body;
   points on or within said second contacting body;
   points on said first contacting surface;
   points on said second contacting surface;
   points within or proximate to said contact; and,
   points within said lubricating material.

5. The apparatus of claim 1, further comprising means to measure the lubricant film thickness at the contact between said first and second contacting body members.

6. The apparatus of claim 5 wherein at least one of said contacting body members is optically transparent and said means to measure the lubricant film thickness at the contact is an optical interferometer.

7. The apparatus of claim 1 wherein one of said contacting body members is a disc.

8. The apparatus of claim 1 wherein one of said contacting body members is a spherical ball.

9. The apparatus of claim 1 wherein one of said contacting body members is a crowned roller.

10. The apparatus of claim 8 wherein the contact between said first contact surface and said second contact surface is circular and remains constant in size independent of orientation of said first and second contacting surfaces.

11. A process for systemic evaluation of tribological performance and durability of individual materials as tribological elements of a lubricated contact system comprising a plurality of contacting bodies meeting together at a uniform point of contact upon their lubricated contacting surfaces, said tribological elements comprising:
   1) any film between said contacting surfaces;
   2) any boundary film adhered to a contacting surface of a contacting body;
   3) a near-surface region of each contacting body; and,
   4) a sub-surface region within each contacting body, said process comprising the steps of:

a. providing a first contact assembly comprising:
  i. a first contacting body member having a first contacting surface, said first contacting body member being comprised of test material and symmetric about at least one central axis;
  ii. means to support said first contacting body member through said at least one symmetric central axis defining a support axis; and,
  iii. means for rotation of said first contacting body member about said support axis, defining an axis of rotation for said first contacting body, which rotation may be varied in both rotational speed and direction;
b. providing a second contact assembly operatively engaging said first contact assembly, said second contact assembly comprising:
  i. a second contacting body member having a second contacting surface engaging said first contact surface in a contact of uniform area independent of the relative motion of said first and second contacting bodies, said second contacting body member being comprised of test material and symmetric about at least one central axis;
  ii. means to support said second contacting body member through said at least one symmetric central axis defining a support axis; and,
  iii. means for rotation of said second contacting body member about said support axis, defining an axis of rotation for said second contacting body, which rotation may be varied in both rotational speed and direction;
c. providing a test lubricating material comprising at least one lubricating substance in the form of a solid, liquid or gas to the contact point of said first contact surface and said second contact surface;
d. providing orientation means to locate said uniform point of contact of said first contact surface and said second contact surface with respect to the axis of rotation of said first contacting body member and the axis of rotation of said second contacting body member;
e. providing a first measurement means to measure the rotational speed and direction of said first contacting body to obtain a first velocity vector for said first contacting body in relation to the contact;
f. providing a second measurement means to measure the rotational speed and direction of said second contacting body to obtain a second velocity vector for said second contacting body in relation to the contact;
wherein an entraining velocity of the lubricated contact system, representative of hydrodynamic and elastohydrodynamic (EHD) lubrication of the contact, is one-half of the vector sum of said first velocity vector and said second velocity vector, and a sliding velocity of the lubricated contact system, representative of lubrication mechanisms within the contact, is the vector difference of said first velocity vector and said second velocity vector; and,
wherein said entraining velocity is controlled independently of said sliding velocity through selective placement of said uniform point of contact of said first and second contact surfaces, by the selective location of said uniform point of contact with respect to the axis of rotation of said first contacting body member and rotational speed of said first and second contact body members, and said sliding velocity is controlled independently of said entraining velocity through the selective placement of said uniform point of contact of said first and second contact surfaces, by the selective location of said uniform point of contact with respect to the axis of rotation of said first contacting body member and rotational speed of said first and second contact body members;
g. selectively varying the orientation of said contact relative to said first and second contact surfaces and the speed of rotation of said first and second contacting body members to obtain an entraining velocity for the lubricated contact system selected independently of said sliding velocity and a sliding velocity for the lubricated contact system selected independently of said entraining velocity;
h. measuring at least one performance parameter of the lubricated contact system for said selected entraining velocity and said selected sliding velocity.

12. The process of claim 11 wherein the systemic evaluation results in a performance map of the contact system, outlining specific regions where lubrication and failure mechanisms are operative.

13. A process for the simulation of an actual tribological contact encountered in machine components using a lubricated contact system test apparatus for systemic evaluation of tribological performance and durability of individual materials as tribological elements of a lubricated contact system comprising a plurality of contacting bodies meeting together at a uniform point of contact upon their lubricated contacting surfaces, said tribological elements comprising:
  1) any film between said contacting surfaces;
  2) any boundary film adhered to a contacting surface of a contacting body;
  3) a near-surface region of each contacting body; and,
  4) a sub-surface region within each contacting body, said lubricated contact system test apparatus comprising:
    a. a first contact assembly comprising:
      i. a first contacting body member having a first contacting surface, said first contacting body member being comprised of test material and symmetric about at least one central axis;
      ii. means to support said first contacting body member through said at least one symmetric central axis defining a support axis; and,
      iii. means for rotation of said first contacting body member about said support axis, defining an axis of rotation for said first contacting body, which rotation may be varied in both rotational speed and direction;
    b. a second contact assembly operatively engaging said first contact assembly, said second contact assembly comprising:
      i. a second contacting body member having a second contacting surface engaging said first contact surface in a contact of uniform area independent of the relative motion of said first and second contacting bodies, said second contacting body member being comprised of test material and symmetric about at least one central axis;
      ii. means to support said second contacting body member through said at least one symmetric central axis defining a support axis; and,
      iii. means for rotation of said second contacting body member about said support axis, defining an axis of rotation for said second contacting body, which rotation may be varied in both rotational speed and direction;

c. lubrication means to provide a test lubricating material comprising at least one lubricating substance in the form of a solid, liquid or gas to the contact point of said first contact surface and said second contact surface;

d. orientation means to locate said uniform point of contact of said first contact surface and said second contact surface with respect to the axis of rotation of said first contacting body member and the axis of rotation of said second contacting body member;

e. means to measure the rotational speed and direction of said first contacting body to obtain a first velocity vector for said first contacting body in relation to the contact;

f. means to measure the rotational speed and direction of said second contacting body to obtain a second velocity vector for said second contacting body in relation to the contact;

wherein an entraining velocity of the lubricated contact system, representative of hydrodynamic and elastohydrodynamic (EHD) lubrication of the contact, is one-half of the vector sum of said first velocity vector and said second velocity vector, and a sliding velocity of the lubricated contact system, representative of lubrication mechanisms within the contact, is the vector difference of said first velocity vector and said second velocity vector; and, wherein said entraining velocity is controlled independently of said sliding velocity through selective placement of said uniform point of contact of said first and second contact surfaces, by the selective location of said uniform point of contact with respect to the axis of rotation of said first contacting body member and the axis of rotation of said second contacting body member and rotational speed of said first and second contact body members, and, said sliding velocity is controlled independently of said entraining velocity through the selective placement of said uniform point of contact of said first and second contact surfaces, by the selective location of said uniform point of contact with respect to the axis of rotation of said first contacting body member and the axis of rotation of said second contacting body member and rotational speed of said first and second contact body members; which process comprises:

a. analysis of actual contact to determine parameters encountered in the machine component contact;

b. estimation of equivalent parameters for a simulated contact on a test apparatus contact;

c. creation of a test plan to evaluate the equivalent parameters of the test apparatus throughout a range of operating conditions;

d. verification of the operation of the simulated contact and correction to equivalent parameters as necessary;

e. implementation of test plan and measurement of dependent variables;

f. assembly of data with notation of affects of changes in dependent variables;

g. preparation of accumulated data as tables, plots or averages for the purpose of evaluation; and, h. evaluation of results and determination of conclusions with respect to operational parameters of actual contact from data accumulated from simulated contact.

* * * * *